(12) United States Patent
Jung et al.

(10) Patent No.: US 9,882,141 B2
(45) Date of Patent: Jan. 30, 2018

(54) PYRENE-BASED COMPOUND AND ORGANIC LIGHT-EMITTING DIODE INCLUDING THE SAME

(71) Applicant: SAMSUNG DISPLAY CO., LTD., Yongin, Gyeonggi-Do (KR)

(72) Inventors: Hye-Jin Jung, Yongin (KR); Seok-Hwan Hwang, Yongin (KR); Young-Kook Kim, Yongin (KR); Jin-O Lim, Yongin (KR); Sang-Hyun Han, Yongin (KR); Eun-Jae Jeong, Yongin (KR); Soo-Yon Kim, Yongin (KR); Jun-Ha Park, Yongin (KR); Eun-Young Lee, Yongin (KR); Chang-Ho Lee, Yongin (KR); Jong-Hyuk Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 694 days.

(21) Appl. No.: 14/049,090

(22) Filed: Oct. 8, 2013

(65) Prior Publication Data
US 2014/0167007 A1    Jun. 19, 2014

(30) Foreign Application Priority Data

Dec. 17, 2012  (KR) .......................... 10-2012-0147721

(51) Int. Cl.
*H01L 51/00* (2006.01)
*C07D 403/12* (2006.01)
(Continued)

(52) U.S. Cl.
CPC .......... *H01L 51/006* (2013.01); *C07D 209/86* (2013.01); *C07D 209/88* (2013.01); *C07D 213/38* (2013.01); *C07D 213/74* (2013.01); *C07D 215/12* (2013.01); *C07D 233/64* (2013.01); *C07D 251/24* (2013.01); *C07D 263/32* (2013.01); *C07D 277/28* (2013.01); *C07D 401/04* (2013.01); *C07D 401/12* (2013.01); *C07D 403/10* (2013.01); *C07D 403/12* (2013.01); *C07D 405/04* (2013.01); *C07D 405/12* (2013.01); *C07D 409/04* (2013.01); *C07D 409/12* (2013.01); *C07D 471/04* (2013.01); *H01L 51/0054* (2013.01); *H01L 51/0058* (2013.01);
(Continued)

(58) Field of Classification Search
CPC .......... H01L 51/0054; H01L 51/006–51/0061; H01L 51/0067
See application file for complete search history.

(56) References Cited

U.S. PATENT DOCUMENTS 7,053,255 B2   5/2006   Ikeda et al.
7,233,019 B2   6/2007   Ionkin et al.
(Continued)

FOREIGN PATENT DOCUMENTS

JP       5-21161         1/1993
JP       2002-294957     10/2002
(Continued)

*Primary Examiner* — Alex A Rolland
(74) *Attorney, Agent, or Firm* — Lewis Roca Rothgerber Christie LLP

(57) ABSTRACT

A pyrene-based compound and an organic light-emitting diode including the pyrene-based compound are provided.

19 Claims, 1 Drawing Sheet

(51) Int. Cl.

| | | |
|---|---|---|
| *C07D 213/74* | (2006.01) | |
| *C07D 215/12* | (2006.01) | |
| *C07D 233/64* | (2006.01) | |
| *C07D 401/04* | (2006.01) | |
| *C07D 401/12* | (2006.01) | |
| *C07D 403/10* | (2006.01) | |
| *C07D 405/04* | (2006.01) | |
| *C07D 405/12* | (2006.01) | |
| *C07D 409/04* | (2006.01) | |
| *C07D 409/12* | (2006.01) | |
| *C07D 251/24* | (2006.01) | |
| *C07D 471/04* | (2006.01) | |
| *C07D 263/32* | (2006.01) | |
| *C07D 277/28* | (2006.01) | |
| *C07D 209/86* | (2006.01) | |
| *C07D 209/88* | (2006.01) | |
| *C07D 213/38* | (2006.01) | |
| *H01L 51/50* | (2006.01) | |

(52) U.S. Cl.
CPC ...... *H01L 51/0059* (2013.01); *H01L 51/0061* (2013.01); *H01L 51/0067* (2013.01); *H01L 51/0068* (2013.01); *H01L 51/0069* (2013.01); *H01L 51/0072* (2013.01); *H01L 51/0073* (2013.01); *H01L 51/0074* (2013.01); *H01L 51/5012* (2013.01)

(56) References Cited

U.S. PATENT DOCUMENTS

| | | |
|---|---|---|
| 7,571,894 B2 | 8/2009 | Sotoyama |
| 7,981,523 B2 * | 7/2011 | Hosokawa ............ C07C 211/54 313/504 |
| 2007/0009758 A1 | 1/2007 | Funahashi |
| 2009/0096356 A1 | 4/2009 | Murase et al. |
| 2011/0121268 A1 | 5/2011 | Nagao et al. |

FOREIGN PATENT DOCUMENTS

| | | |
|---|---|---|
| JP | 2005-079459 | 3/2005 |
| JP | 2012-059747 | 3/2012 |
| KR | 10-2005-0107809 | 11/2005 |
| KR | 10-2006-0006760 | 1/2006 |
| KR | 10-2008-0055891 | 6/2008 |
| KR | 10-2011-0040874 | 4/2011 |
| KR | 10-2011-064222 | 6/2011 |
| WO | WO 2006/114949 A1 | 11/2006 |
| WO | WO 2009/084543 A1 | 7/2009 |

* cited by examiner

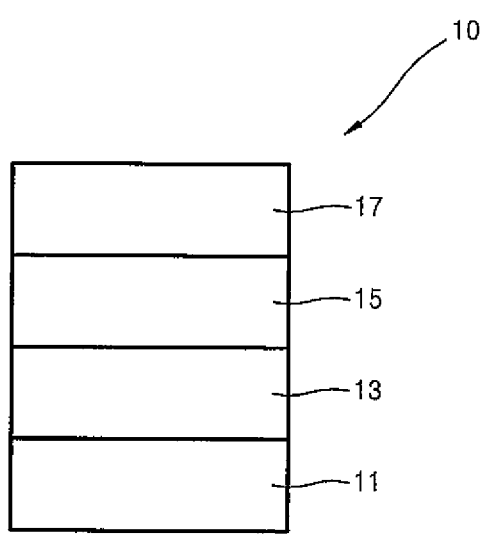

PYRENE-BASED COMPOUND AND ORGANIC LIGHT-EMITTING DIODE INCLUDING THE SAME

CROSS-REFERENCE TO RELATED APPLICATION

This application claims priority to and the benefit of Korean Patent Application No. 10-2012-0147721, filed on Dec. 17, 2012, in the Korean Intellectual Property Office, the entire content of which is incorporated herein by reference.

BACKGROUND

1. Field

The following description relates to a compound for an organic light-emitting diode and an organic light-emitting diode including the same.

2. Description of the Related Art

Organic light-emitting diodes (OLEDs), which are self-emitting diodes, have advantages such as wide viewing angles, good contrast, quick response, high brightness, and good driving voltage characteristics. Additionally, OLEDs can provide multicolored images.

A typical OLED has a structure including a substrate, an anode, a hole transport layer (HTL), an emission layer (EML), an electron transport layer (ETL), and a cathode, which are sequentially stacked on the substrate. The HTL, the EML, and the ETL are organic thin films formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons (carriers) recombine in the organic EML to generate excitons. When the excitons drop from an excited state to a ground state, light is emitted.

SUMMARY

Aspects of one or more embodiments of the present invention are directed toward providing a pyrene-based compound and an organic light-emitting device including the same.

In an embodiment, a pyrene-based compound is provided as represented by Formula 1 below:

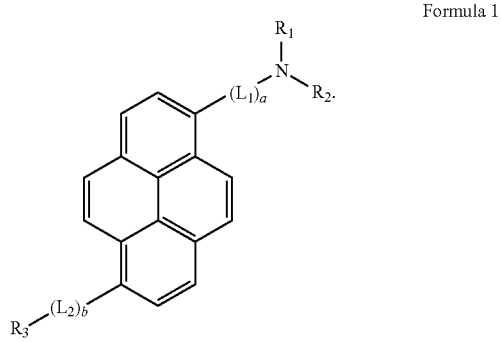

Formula 1

In Formula 1, $L_1$ and $L_2$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, and a substituted or unsubstituted $C_2$-$C_{60}$ heteroarylene group;

a is an integer from 1 to 3;

b is an integer from 0 to 3;

$R_1$ and $R_2$ are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, and a substituted or unsubstituted $C_2$-$C_{60}$ heteroaryl group; and $R_3$ is an electron transporting group selected from a substituted or unsubstituted N-containing 5-membered ring group, a substituted or unsubstituted N-containing 6-membered ring group, a substituted or unsubstituted N-containing 5-membered ring that is fused with a 6-membered ring, and a substituted or unsubstituted N-containing 6-membered ring that is fused with a 6-membered ring.

According to an embodiment of the present invention, provided is an organic light-emitting diode including: a first electrode; a second electrode facing the first electrode; and an organic layer interposed between the first electrode and the second electrode and comprising an emission layer, wherein the organic layer includes a hole transport area interposed between the first electrode and the emission layer and an electron transport area interposed between the emission layer and the second electrode, and the organic layer includes at least one of the pyrene-based compound according to one or more embodiments of the present invention.

BRIEF DESCRIPTION OF THE DRAWING

The above and other features and advantages of the present invention will become more apparent with reference to the following detailed description of exemplary embodiments thereof together with reference to the drawing.

The drawing is a cross-sectional view of the structure of an organic light-emitting device according to an embodiment of the present invention.

DETAILED DESCRIPTION

In the following detailed description, only certain exemplary embodiments of the present invention are shown and described, by way of illustration. As those skilled in the art would recognize, the invention may be embodied in many different forms and should not be construed as being limited to the embodiments set forth herein. Also, in the context of the present application, when a first element is referred to as being "on" a second element, it can be directly on the second element or be indirectly on the second element with one or more intervening elements interposed therebetween. Like reference numerals designate like elements throughout the specification. As used herein, the term "and/or" includes any and all combinations of one or more of the associated listed items. Expressions such as "at least one of", when preceding a list of elements, modifies the list of elements as a whole, and does not modify the individual elements of the list.

In an embodiment, a pyrene-based compound having a pyrene core is provided. The pyrene-based compound according to an embodiment of the present invention is represented by Formula 1 below:

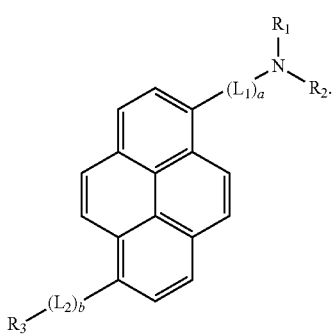

Formula 1

In one embodiment, in Formula 1, $L_1$ and $L_2$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, and a substituted or unsubstituted $C_2$-$C_{60}$ heteroarylene group.

In one embodiment, in Formula 1, $L_1$ and $L_2$ are each independently selected from i) phenylene, pentalenylene, indenylene, naphtylene, azulenylene, heptalenylene, indacenylene, acenaphtylene, fluorenylene, spiro-fluorenylene, phenalenylene, phenanthrenylene, anthrylene, fluoranthenylene, triphenylenylene, pyrenylene, chrysenylene, naphthacenylene, picenylene, perylenylene, pentaphenylene, hexacenylene, pyrrolylene, imidazolylene, pyrazolylene, pyridinylene, pyrazinylene, pyrimidinylene, pyridazinylene, isoindolylene, indolylene, indazolylene, purinylene, quinolinylene, benzoquinolinylene, phthalazinylene, naphthyridinylene, quinoxalinylene, quinazolinylene, cinnolinylene, carbazolylene, phenanthridinylene, acridinylene, phenanthrolinylene, phenazinylene, benzooxazolylene, benzoimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazdylene, triazinylene, benzooxazolylene, dibenzofuranylene, dibenzothiophenylene, and benzocarbazolylene; and ii) phenylene, pentalenylene, indenylene, naphtylene, azulenylene, heptalenylene, indacenylene, acenaphtylene, fluorenylene, spiro-fluorenylene, phenalenylene, phenanthrenylene, anthrylene, fluoranthenylene, triphenylenylene, pyrenylene, chrysenylene, naphthacenylene, picenylene, perylenylene, pentaphenylene, hexacenylene, pyrrolylene, imidazolylene, pyrazolylene, pyridinylene, pyrazinylene, pyrimidinylene, pyridazinylene, isoindolylene, indolylene, indazolylene, purinylene, quinolinylene, benzoquinolinylene, phthalazinylene, naphthyridinylene, quinoxalinylene, quinazolinylene, cinnolinylene, carbazolylene, phenanthridinylene, acridinylene, phenanthrolinylene, phenazinylene, benzooxazolylene, benzoimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazdylene, triazinylene, benzooxazolylene, dibenzofuranylene, dibenzothiophenylene, and benzocarbazolylene, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{20}$ aryl group and a $C_2$-$C_{20}$ heteroaryl group; and a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

In one embodiment, at least one of $L_1$ and $L_2$ in Formula 1 are each independently represented by one of Formulae 2-1 to 2-27 below, but is not limited thereto:

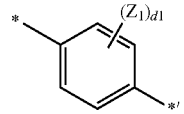

Formula 2-1

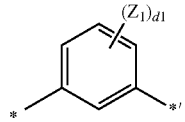

Formula 2-2

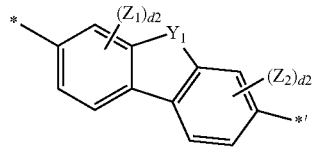

Formula 2-3

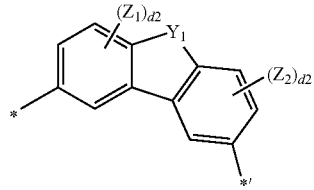

Formula 2-4

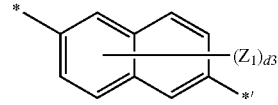

Formula 2-5

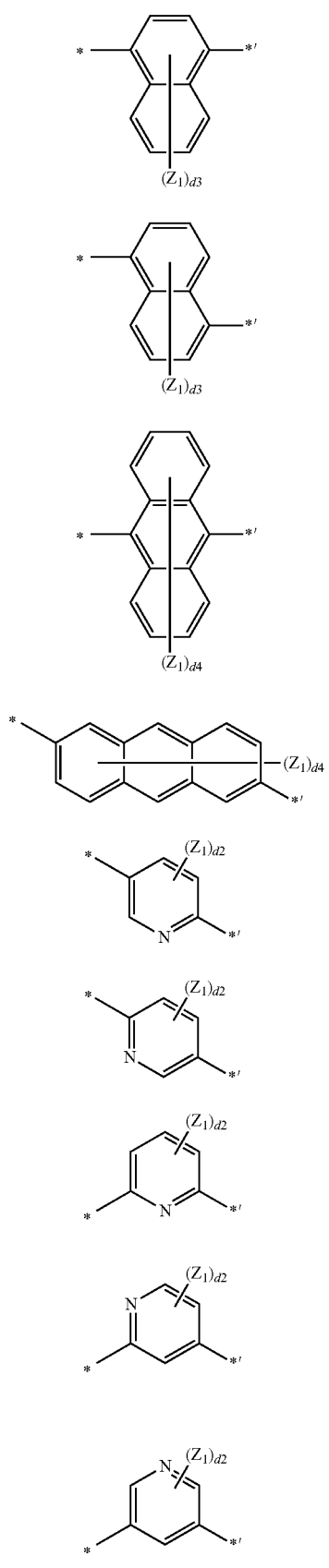
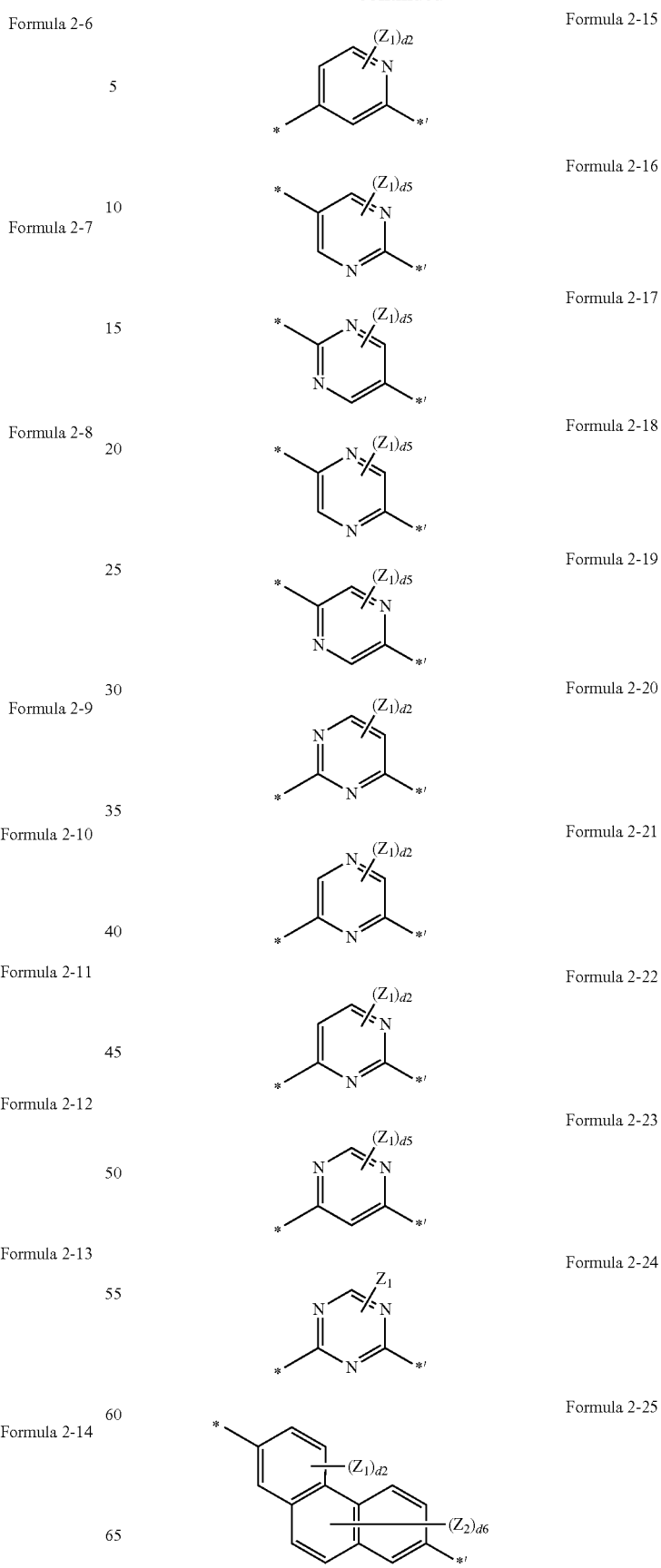

Formula 2-26

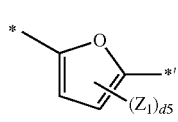

Formula 2-27

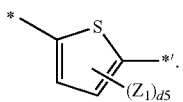

In one embodiment, in Formulae 2-1 to 2-27, $Y_1$ is O, S, $C(Z_3)(Z_4)$, or $N(Z_5)$; and $Z_1$ to $Z_5$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{20}$ aryl group and a $C_2$-$C_{20}$ heteroaryl group; and a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group;

d1 is an integer from 1 to 4; d2 is an integer from 1 to 3; d3 is an integer from 1 to 6; d4 is an integer from 1 to 8; d5 is 1 or 2; d6 is an integer from 1 to 5; * is a binding site with the pyrene core in Formula 1 or a binding site with a neighboring $L_1$ or $L_2$; and *' is a binding site with a neighboring $L_1$ or $L_2$ in Formula 1, or a binding site with $R_3$ or N.

For example, $Z_1$ to $Z_5$ in Formulae 2-1 to 2-27 may be each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —$Si(Q_{13})(Q_{14})(Q_{15})$ wherein $Q_{13}$ to $Q_{15}$ may be each independently a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, or an isoquinolyl group.

When $Z_1$ in Formula 2-1 is 2 or more, 2 or more of $Z_1$ may be identical to or different from each other, and this can also be applied to Formulae 2-2 to 2-27.

$L_1$ and $L_2$ in Formula 1 may be each independently represented by one of Formulae 3-1 to 3-15 below:

Formula 3-1

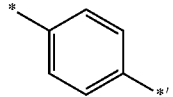

Formula 3-2

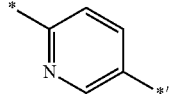

Formula 3-3

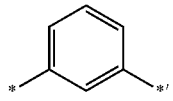

Formula 3-4

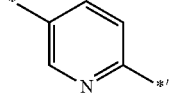

Formula 3-5

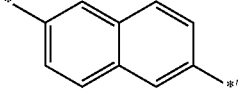

Formula 3-6

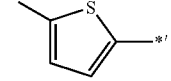

-continued

Formula 3-7

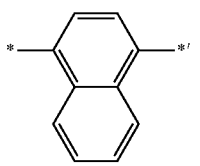

Formula 3-8

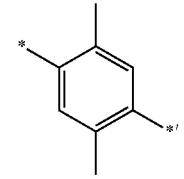

Formula 3-9

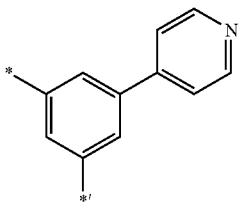

Formula 3-10

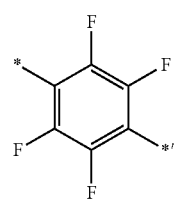

Formula 3-11

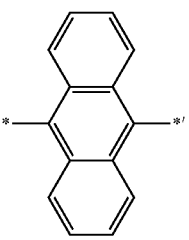

Formula 3-12

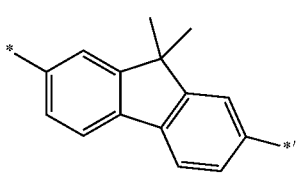

Formula 3-13

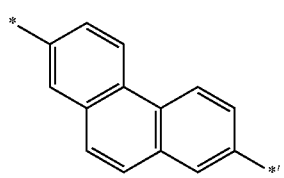

Formula 3-14

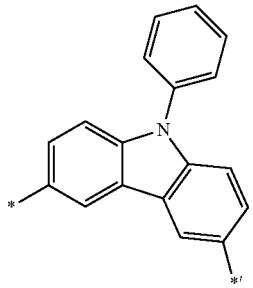

Formula 3-15

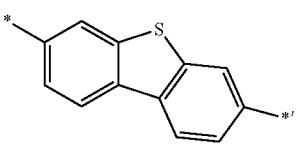

* in Formulae 3-1 to 3-15 is a binding site with the pyrene core in Formula 1 or a binding site with a neighboring $L_1$ or $L_2$; and *' is a binding site with a neighboring $L_1$ or $L_2$ in Formula 1 or a binding site with $R_3$ or N.

a in Formula 1 refers to a number of $L_1$ and is an integer from 1 to 3. When a is 2 or 3, each $L_1$ may be identical to or different from each other. For example, a may be 1 or 2, but is not limited thereto.

b in Formula 1 refers to a number of $L_2$ and is an integer from 0 to 3. When b is 0, $R_3$ may be directly linked to the pyrene core. When b is 2 or 3, each $L_2$ may be identical to or different from each other. For example, b may be 0 or 1, but is not limited thereto.

$R_3$ in Formula 1 may be an electron transporting group selected from a substituted or unsubstituted N-containing 5-membered ring group, a substituted or unsubstituted N-containing 6-membered ring group, a substituted or unsubstituted N-containing 5-membered ring that is fused with a 6-membered ring, and a substituted or unsubstituted N-containing 6-membered ring that is fused with a 6-membered ring.

For example, $R_3$ in Formula 1 may be selected from i) a pyrrolyl group, an imidazolyl group, a pyrazolyl group, a triazolyl group, a oxazolyl group, an isoxazolyl group, an oxadiazolyl group, an oxatriazolyl group, a thiazolyl group, an isothiazolyl group, a thiadiazolyl group, a thioatriazolyl group, a benzoimidazolyl group, an imidazopyrimidinyl group, an imidazopyridinyl group, a benzoxazolyl group, a benzothiazolyl group, a pyridinyl group, a pyrimidinyl group, a pyrazinyl group, a triazinyl group, a quinolinyl group, an isoquinolinyl group, an indolyl group, a phthalazinyl group, a quinoxalinyl group, and a quinazolinyl group; and ii) a pyrrolyl group, an imidazolyl group, a pyrazolyl group, a triazolyl group, a oxazolyl group, an isoxazolyl group, an oxadiazolyl group, an oxatriazolyl group, a thiazolyl group, an isothiazolyl group, a thiadiazolyl group, a thioatriazolyl group, benzoimidazolyl group, an imidazopyrimidinyl group, an imidazopyridinyl group, a benzoxazolyl group, benzothiazolyl group, a pyridinyl group, a pyrimidinyl group, a pyrazinyl group, a triazinyl group, a quinolinyl group, an isoquinolinyl group, an indolyl group, a phthalazinyl group, a quinoxalinyl group and a quinazolinyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —Si($Q_{13}$)($Q_{14}$)($Q_{15}$) wherein $Q_{13}$ to $Q_{15}$ may be each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

According to an embodiment of the present invention, $R_3$ in Formula 1 is represented by any one of Formulae 4-1 to 4-14 below, but is not limited thereto:

Formula 4-1

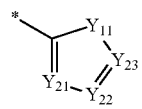

Formula 4-2

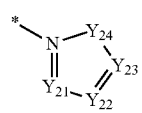

Formula 4-3

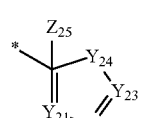

Formula 4-4

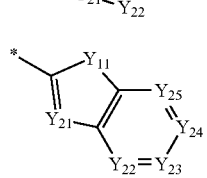

Formula 4-5

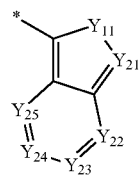

Formula 4-6

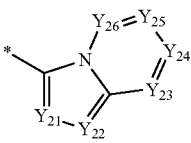

Formula 4-7

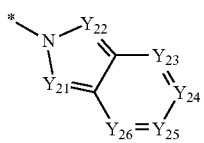

Formula 4-8

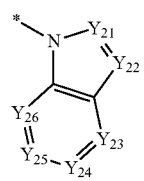

Formula 4-9

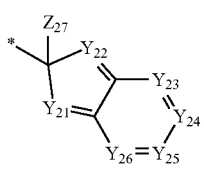

Formula 4-10

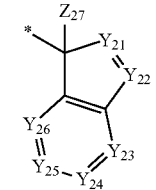

Formula 4-11

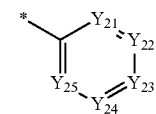

Formula 4-12

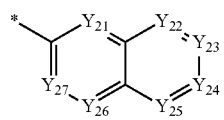

Formula 4-13

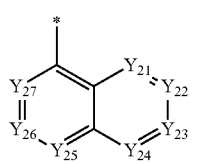

Formula 4-14

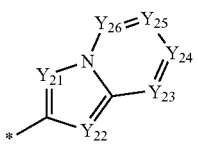

In Formulae 4-1 to 4-14, $Y_{11}$ is O, S, $N(Z_{11})$, or $C(Z_{12})(Z_{13})$; $Y_{21}$ is N or $C(Z_{21})$; $Y_{22}$ is N or $C(Z_{22})$; $Y_{23}$ is N or $C(Z_{23})$; $Y_{24}$ is N or $C(Z_{24})$; $Y_{25}$ is N or $C(Z_{25})$; $Y_{26}$ is N or $C(Z_{26})$; $Y_{27}$ is N or $C(Z_{27})$; $Z_{11}$ to $Z_{13}$ and $Z_{21}$ to $Z_{27}$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{20}$ aryl group and a $C_2$-$C_{20}$ heteroaryl group;

a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —$Si(Q_{13})(Q_{14})(Q_{15})$ wherein $Q_{13}$ to $Q_{15}$ may be each independently a $C_1$-$C_{20}$ alkyl group, a $C_1$-$C_{20}$ alkoxy group, a $C_6$-$C_{20}$ aryl group, or a $C_2$-$C_{20}$ heteroaryl group; and * is a binding site with $L_1$ in Formula 1.

In one embodiment, $Z_{11}$ to $Z_{13}$ and $Z_{21}$ to $Z_{27}$ in Formulae 4-1 to 4-14 are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —$Si(Q_{13})(Q_{14})(Q_{15})$ wherein $Q_{13}$ to $Q_{15}$ may be each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group, but is not limited thereto.

According to an embodiment of the present invention, $R_3$ in Formula 1 is selected from Formulae 4-1(1), 4-1(2), 4-1(3), 4-4(1), 4-4(2), 4-4(3), 4-6(1), 4-6(2), 4-8(1), 4-11(1), 4-11(2), 4-11(3), 4-11(4), 4-12(1), 4-14(1), and 4-14(2):

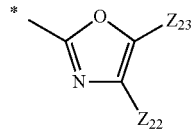

Formula 4-1(1)

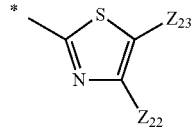

Formula 4-1(2)

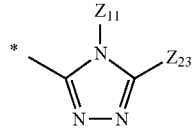

Formula 4-1(3)

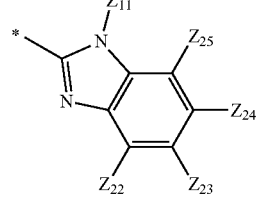

Formula 4-4(1)

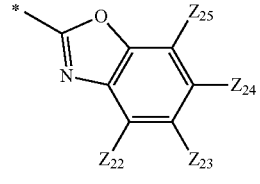

Formula 4-4(2)

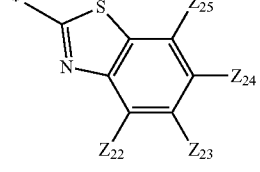

Formula 4-4(3)

In one embodiment, $Z_{11}$ and $Z_{21}$ and $Z_{21}$ to $Z_{26}$ in Formulae 4-1(1), 4-1(2), 4-1(3), 4-4(1), 4-4(2), 4-4(3), 4-6(1), 4-6(2), 4-8(1), 4-11(1), 4-11(2), 4-11(3), 4-11(4), 4-12(1), 4-14(1) and 4-14(2) are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —Si($Q_{13}$)($Q_{14}$)($Q_{15}$) wherein $Q_{13}$ to $Q_{15}$ may be each independently a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, or an isoquinolyl group.

$R_1$ and $R_2$ in Formula 1 may be each independently substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, and a substituted or unsubstituted $C_2$-$C_{60}$ heteroaryl group.

For example, in an embodiment, $R_1$ and $R_2$ in Formula 1 are each independently selected from i) phenyl, pentalenyl, indenyl, naphtyl, azulenyl, heptalenyl, indacenyl, acenaphtyl, fluorenyl, spiro-a fluorenyl, phenalenyl, phenanthrenyl, anthryl, fluoranthenyl, triphenylenylene, pyrenyl, chrysenyl, naphthacenyl, picenyl, perylenyl, pentaphenyl, hexacenyl, pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazolyl, oxadiazolylene, triazinylene, benzooxazolyl, dibenzofuranyl, dibenzothiophenyl, and benzocarbazolyl; and ii) phenyl, pentalenyl, indenyl, naphtyl, azulenyl, heptalenyl, indacenyl, acenaphtyl, fluorenyl, spiro-a fluorenyl, phenalenyl, phenanthrenyl, anthryl, fluoranthenyl, triphenylenylene, pyrenyl, chrysenyl, naphthacenyl, picenyl, perylenyl, pentaphenyl, hexacenyl, pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazolyl, oxadiazolylene, triazinylene, benzooxazolyl, dibenzofuranyl, dibenzothiophenyl, and benzocarbazolyl, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{20}$ aryl group and a $C_2$-$C_{20}$ heteroaryl group; and a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

According to an embodiment of the present invention, $R_1$ and $R_2$ in Formula 1 are each independently selected from Formulae 5-1 to 5-13 below:

Formula 5-1

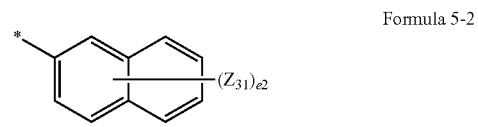

Formula 5-2

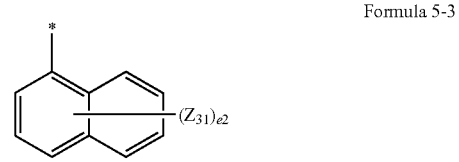

Formula 5-3

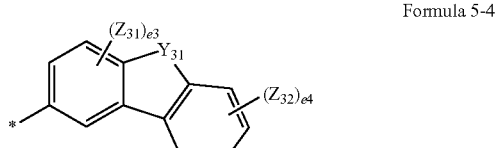

Formula 5-4

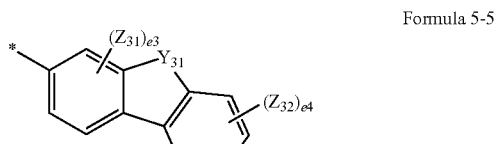

Formula 5-5

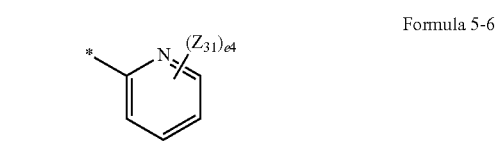

Formula 5-6

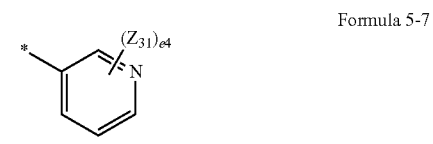

Formula 5-7

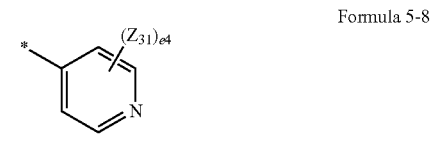

Formula 5-8

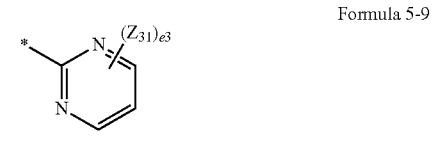

Formula 5-9

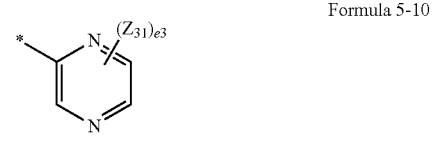

Formula 5-10

Formula 5-11

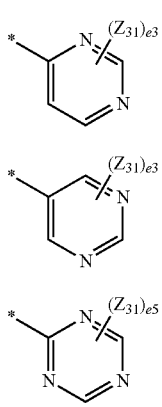

Formula 5-12

Formula 5-13

In one embodiment, $Y_{31}$ in Formulae 5-1 to 5-13 is O, S, $C(Z_{33})(Z_{34})$, or $N(Z_{35})$; $Z_{31}$ to $Z_{35}$ may be each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{20}$ aryl group and a $C_2$-$C_{20}$ heteroaryl group; and a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and e1 is an integer from 1 to 5; e2 is an integer from 1 to 7; e3 is an integer from 1 to 3; e4 is an integer from 1 to 4; e5 is 1 or 2; and * is a binding site with N in Formula 1.

For example, $Z_{31}$ to $Z_{35}$ in Formulae 5-1 to 5-13 may be each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group; and —$Si(Q_{13})(Q_{14})(Q_{15})$ wherein $Q_{13}$ to $Q_{15}$ may be each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

According to an embodiment of the present invention, the pyrene-based compound may be a compound having i) $L_1$ and $L_2$ that are each independently represented by one of Formula 2-1 to 2-27, ii) a that is 1 or 2; iii) b that is 0 or 1; iv) $R_3$ that is represented by one of Formulae 4-1 to 4-14 (for example, one of Formulae 4-1(1), 4-1(2), 4-1(3), 4-4(1), 4-4(2), 4-4(3), 4-6(1), 4-6(2), 4-8(1), 4-11(1), 4-11(2), 4-11(3), 4-11(4), 4-12(1), 4-14(1), and 4-14(2)), and v) $R_1$ and $R_2$ that are each independently one of Formulae 5-1 to 5-13.

According to embodiments herein described, $R_1$ and $R_2$ in Formula 1 are not bonded to each other (e.g. to form a ring) and instead are separate substituents.

In some embodiments, the pyrene-based compound is one of Compounds 1 to 71, but is not limited thereto:

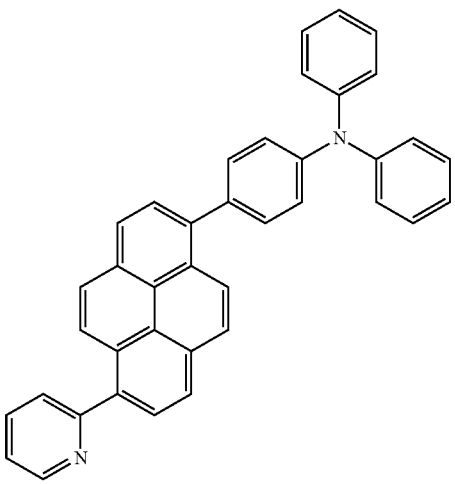

1

-continued
2
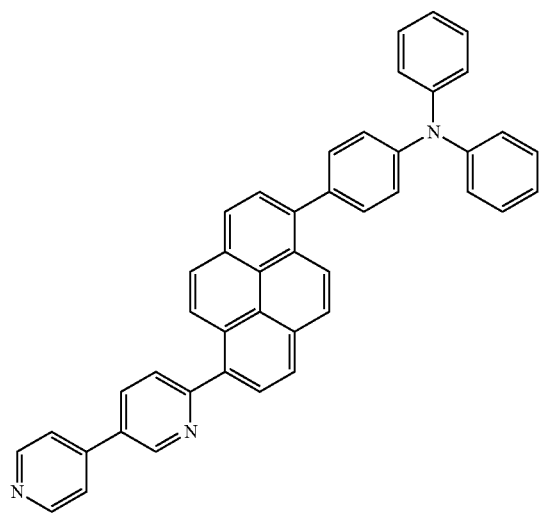
3
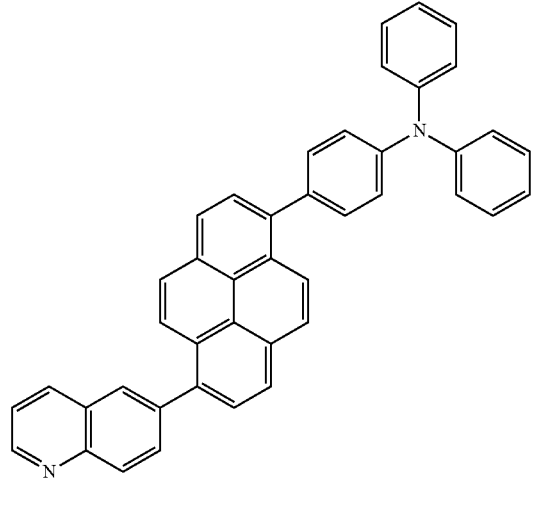
4
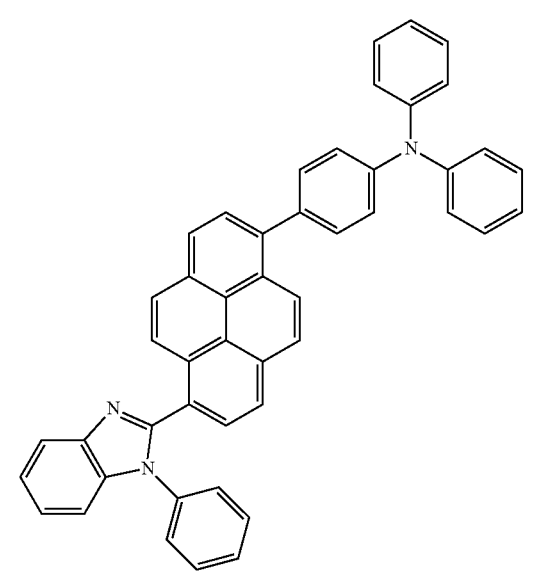
-continued
5
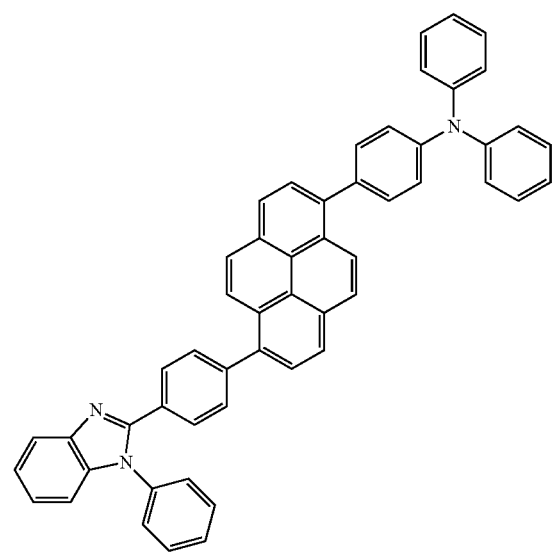
6
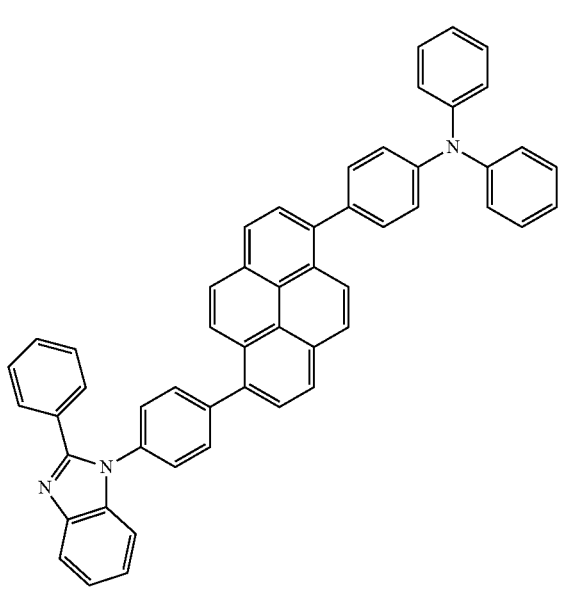
7
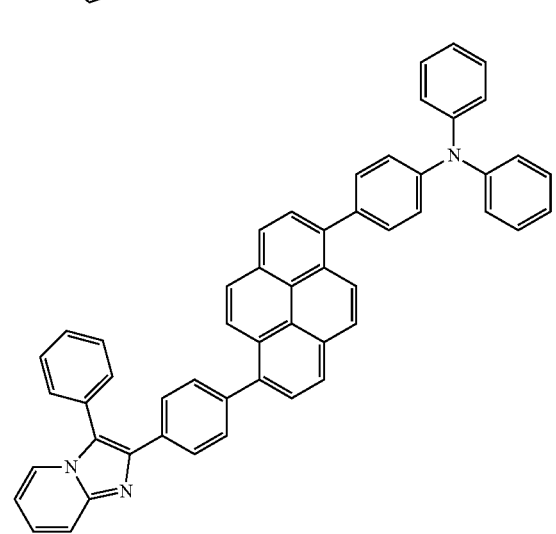

8
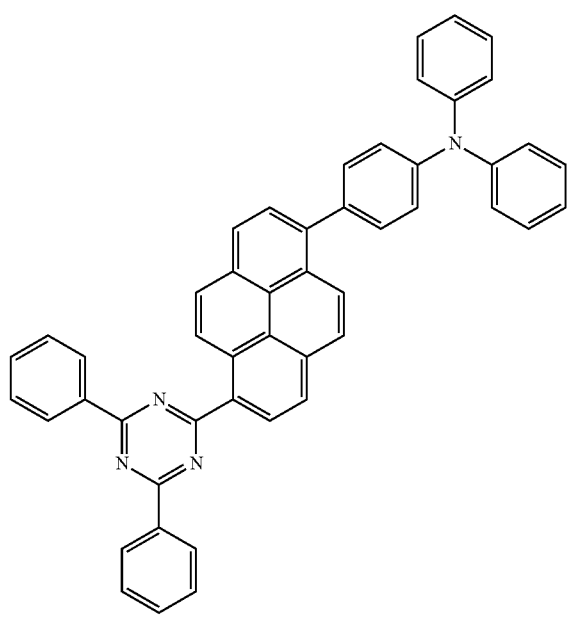
9
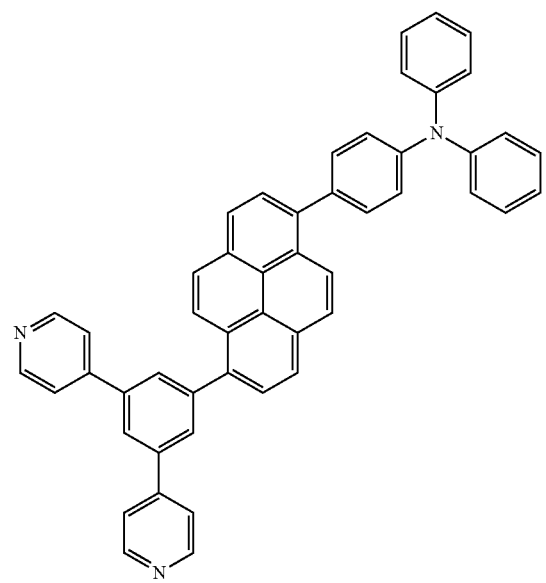
10
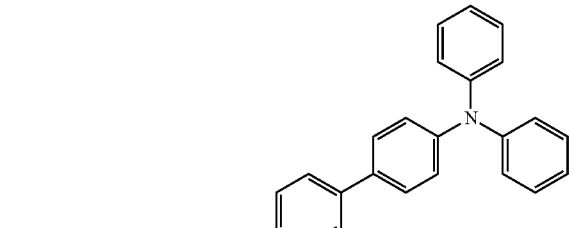
11
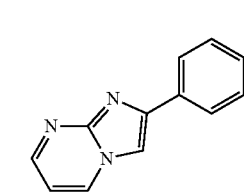
12
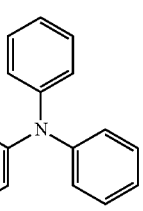

13
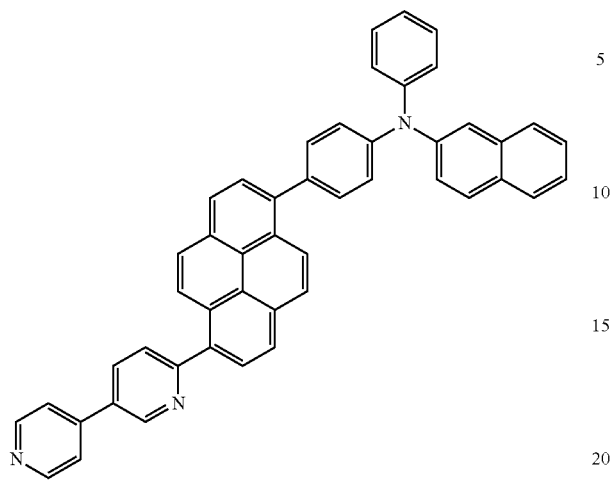
14
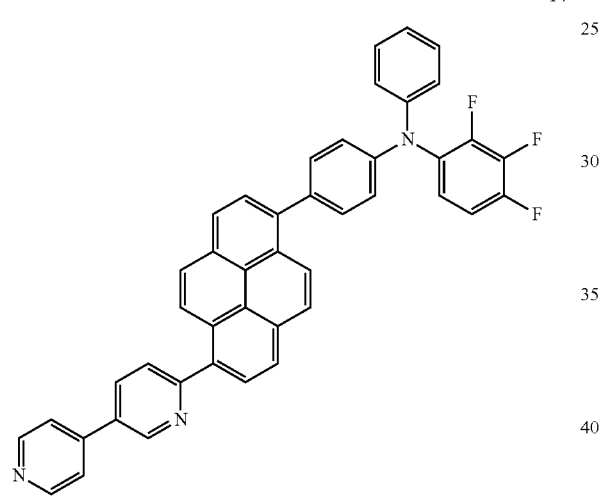
15
16
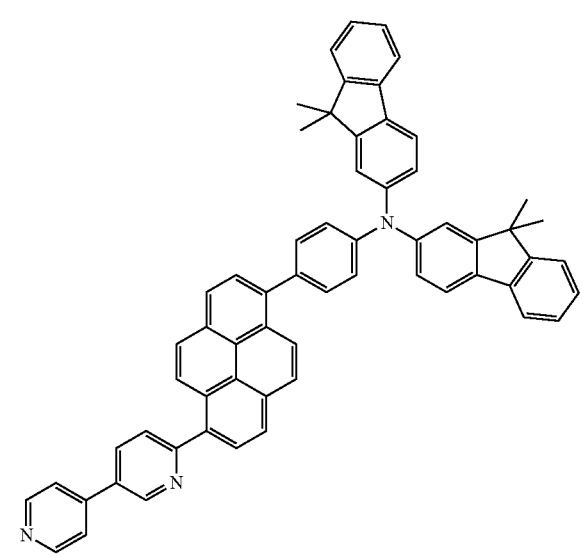
17
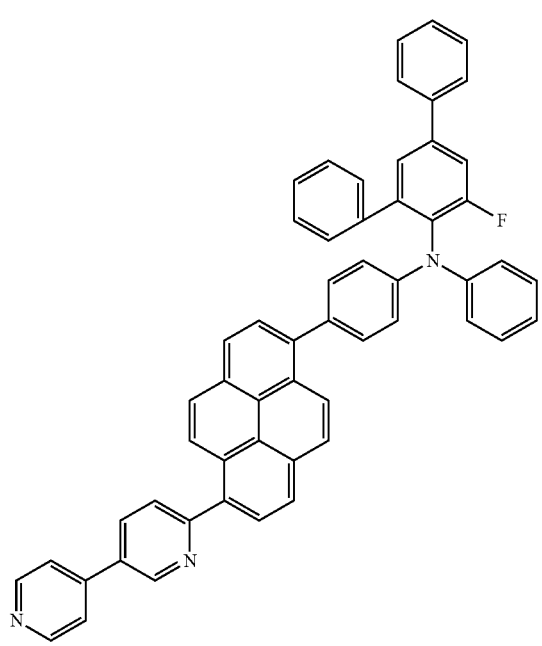

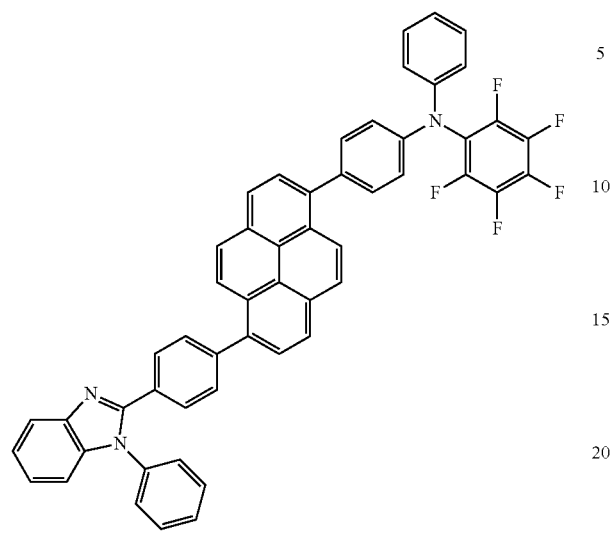
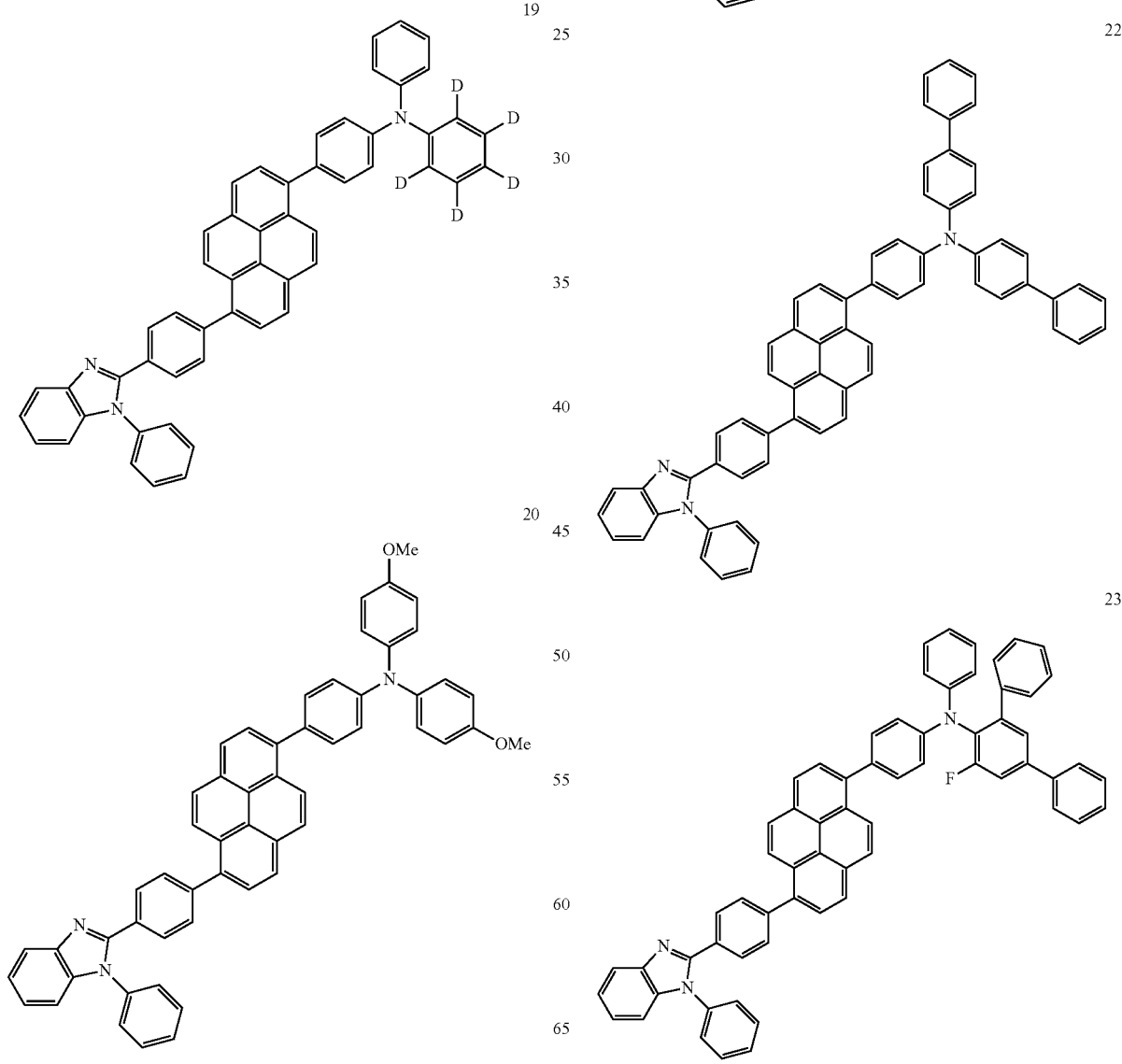

24
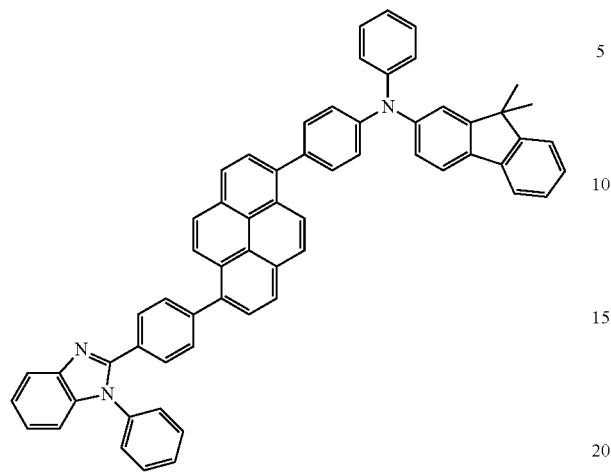
25
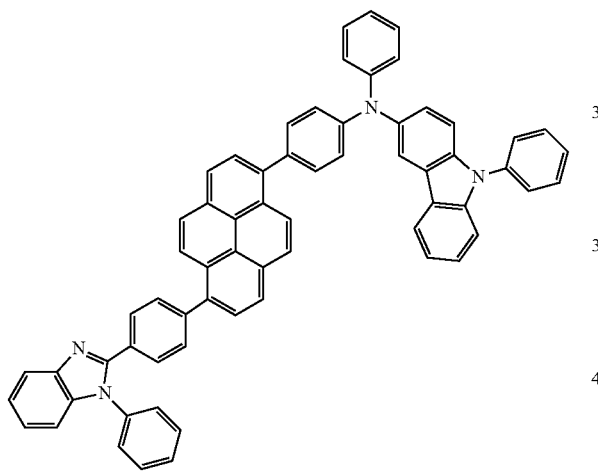
26
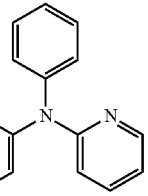
27
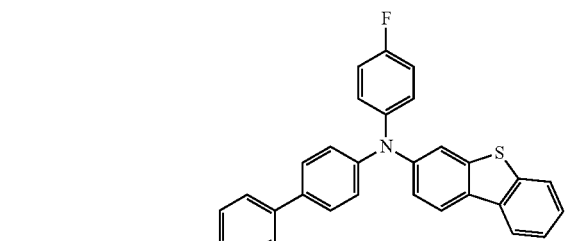
28
29
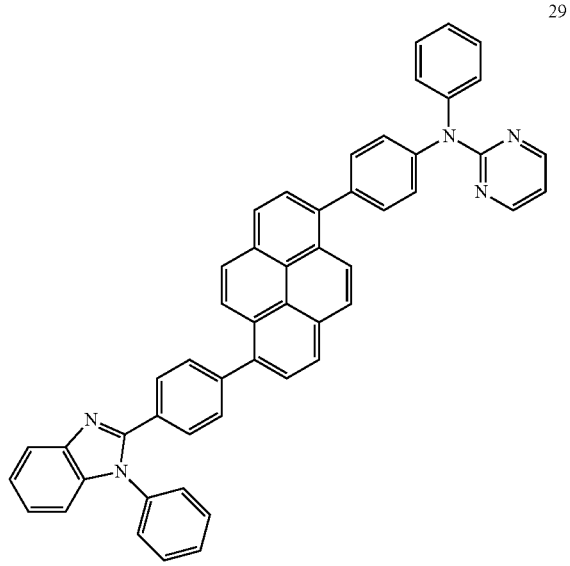

30
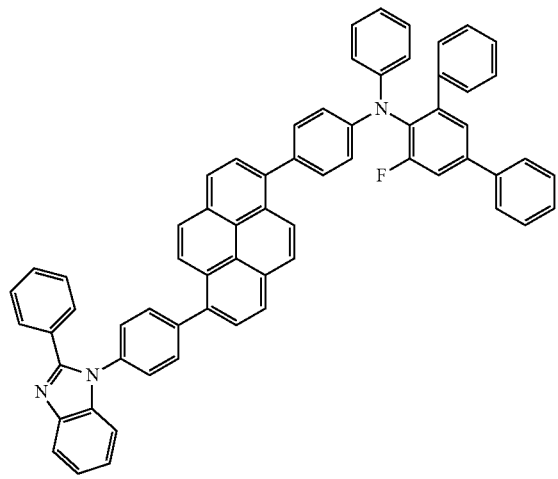
31
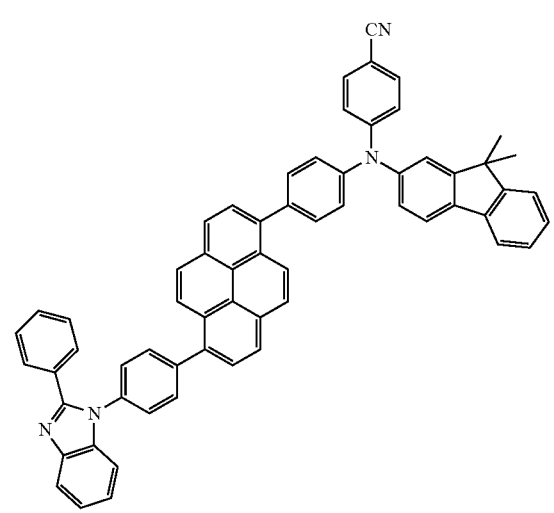
32
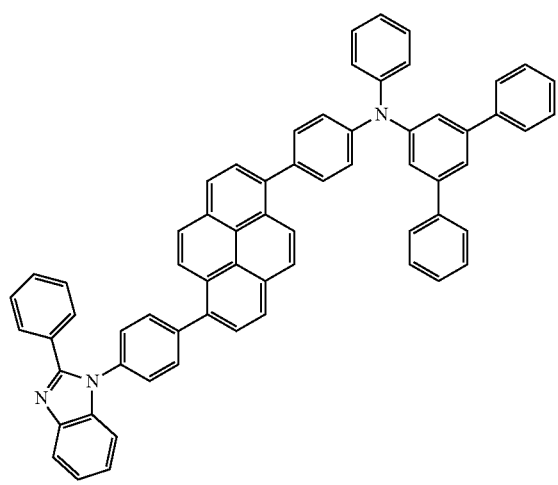
33
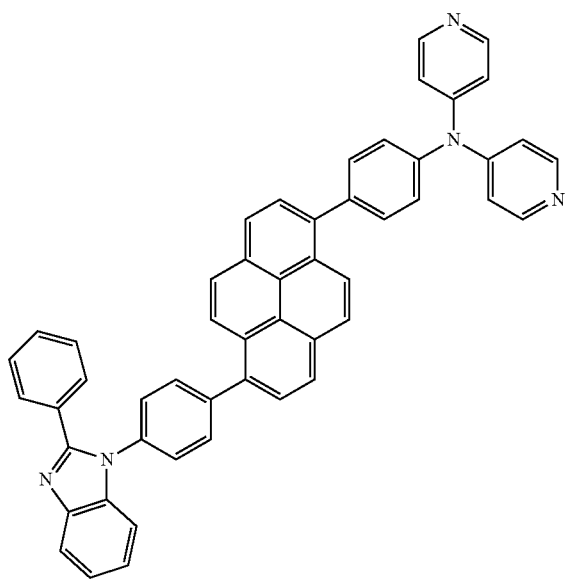
34
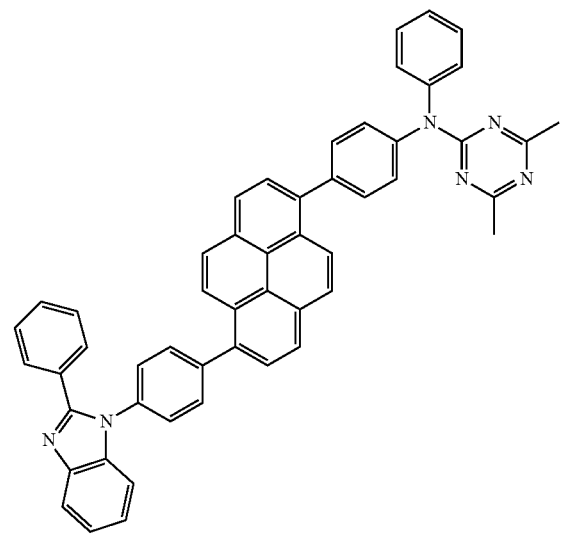
35
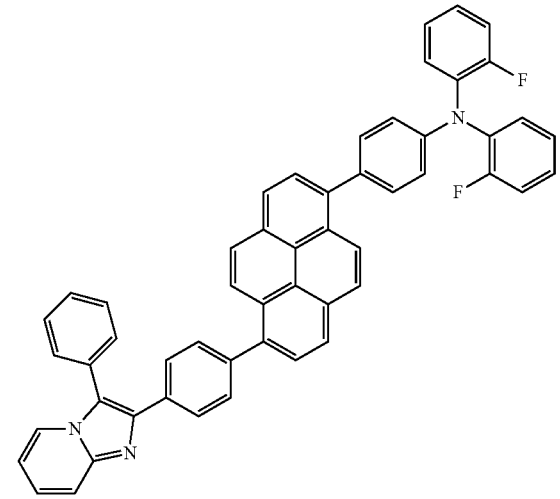

33
-continued
36
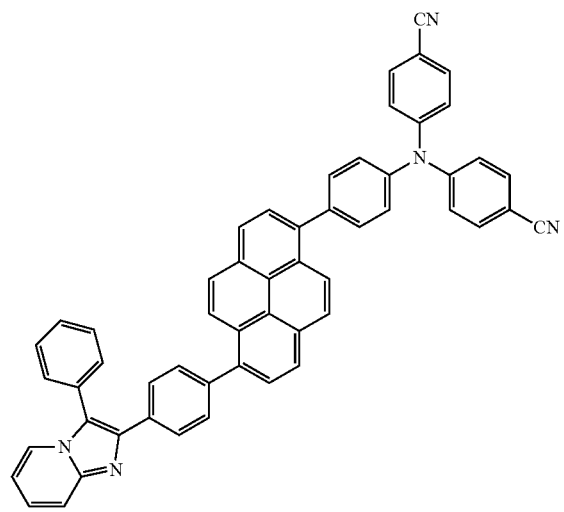
37
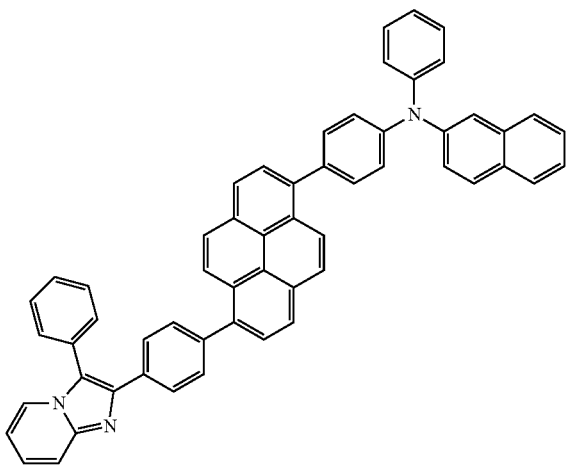
38
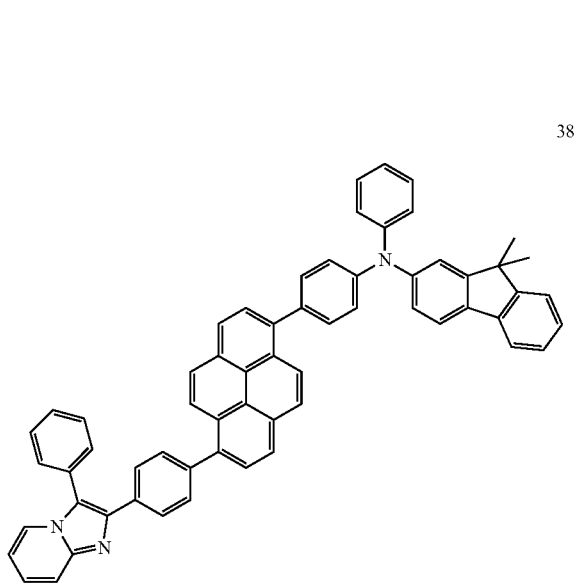
34
-continued
39
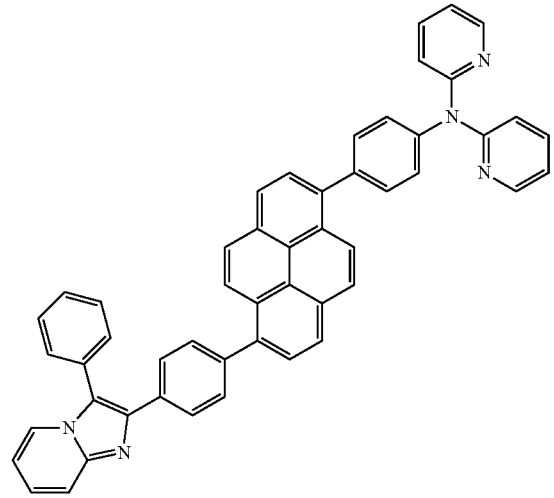
40
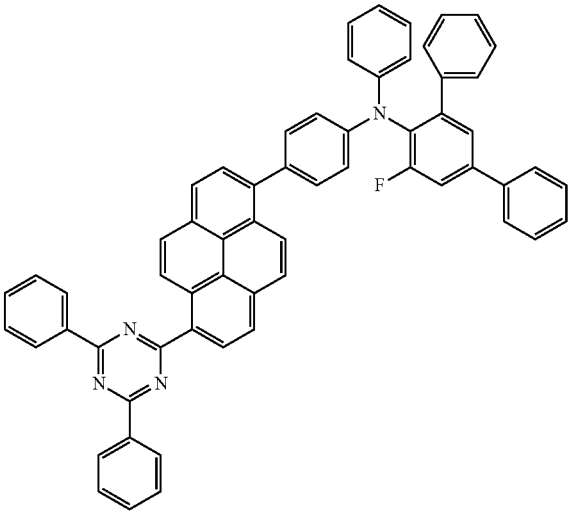
41
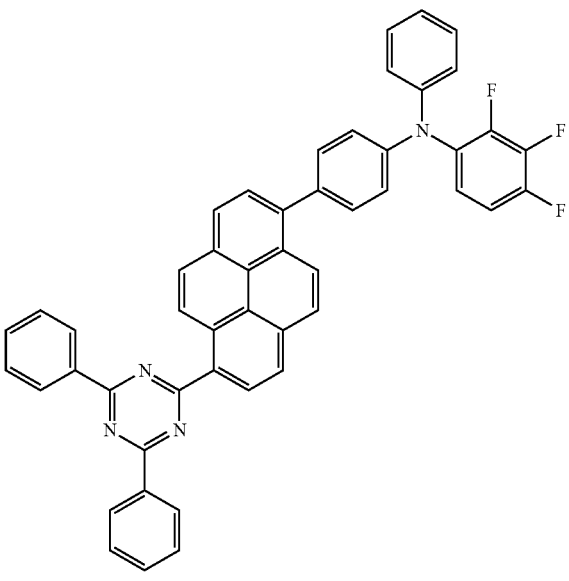

42
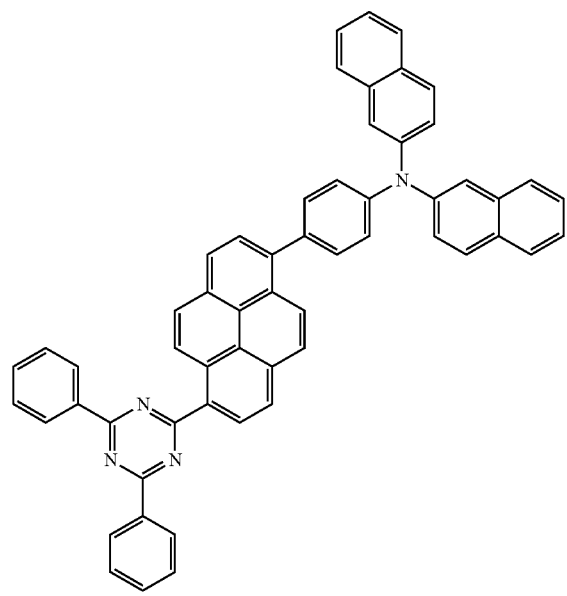
44
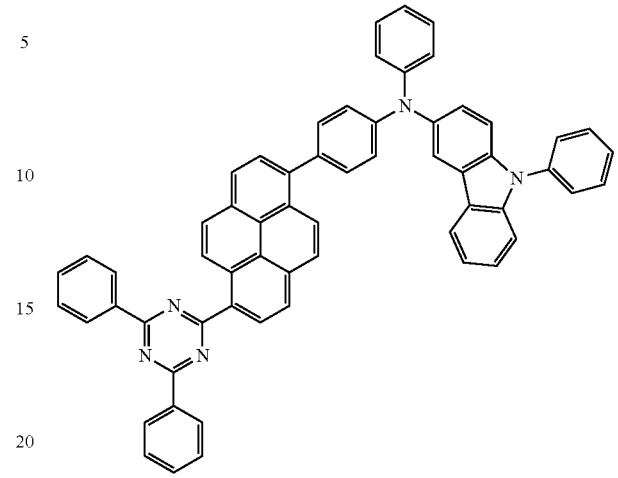
43
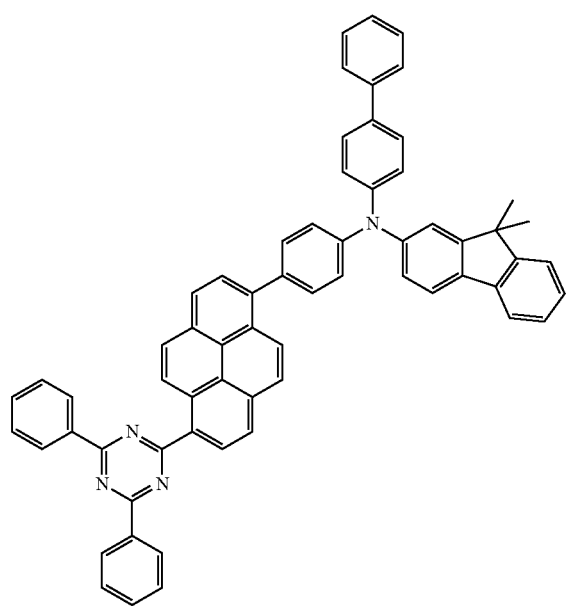
45
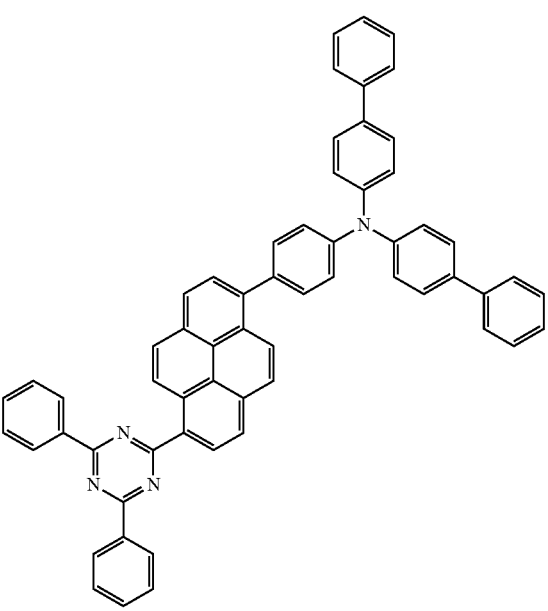

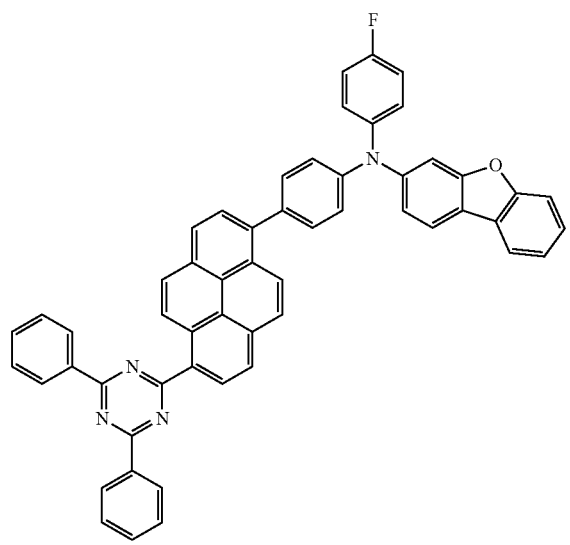
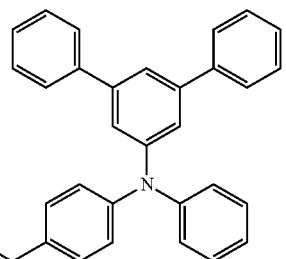
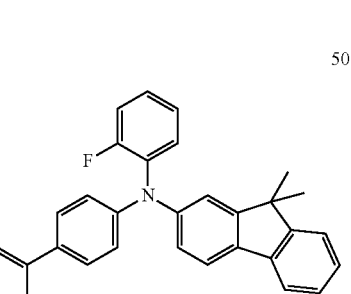
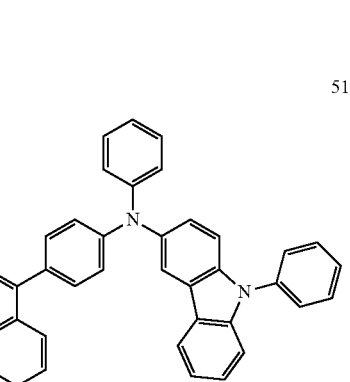

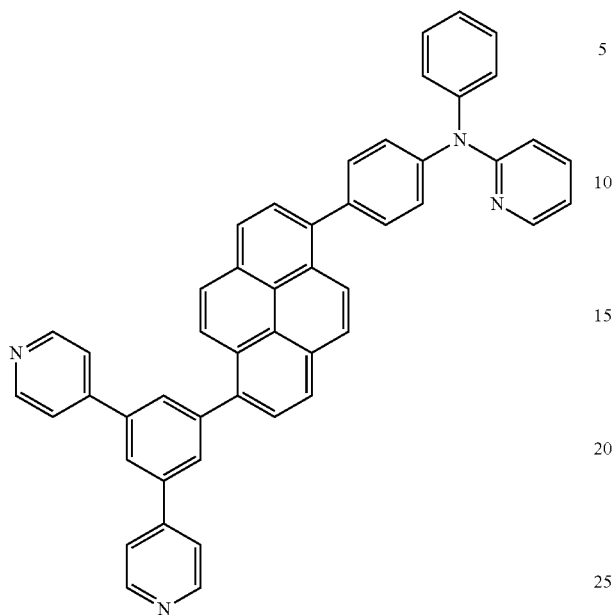
52
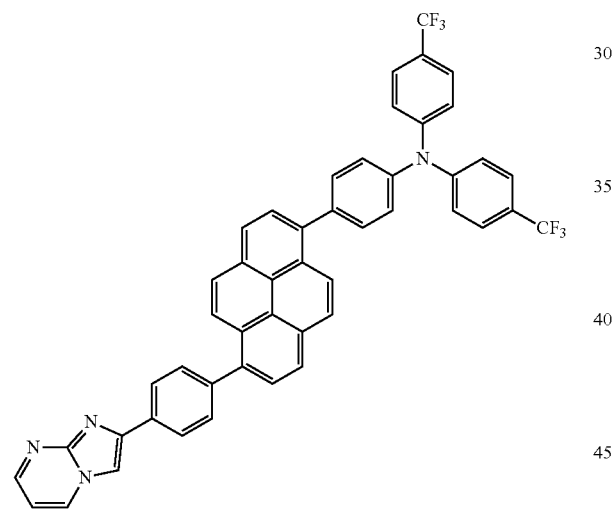
53
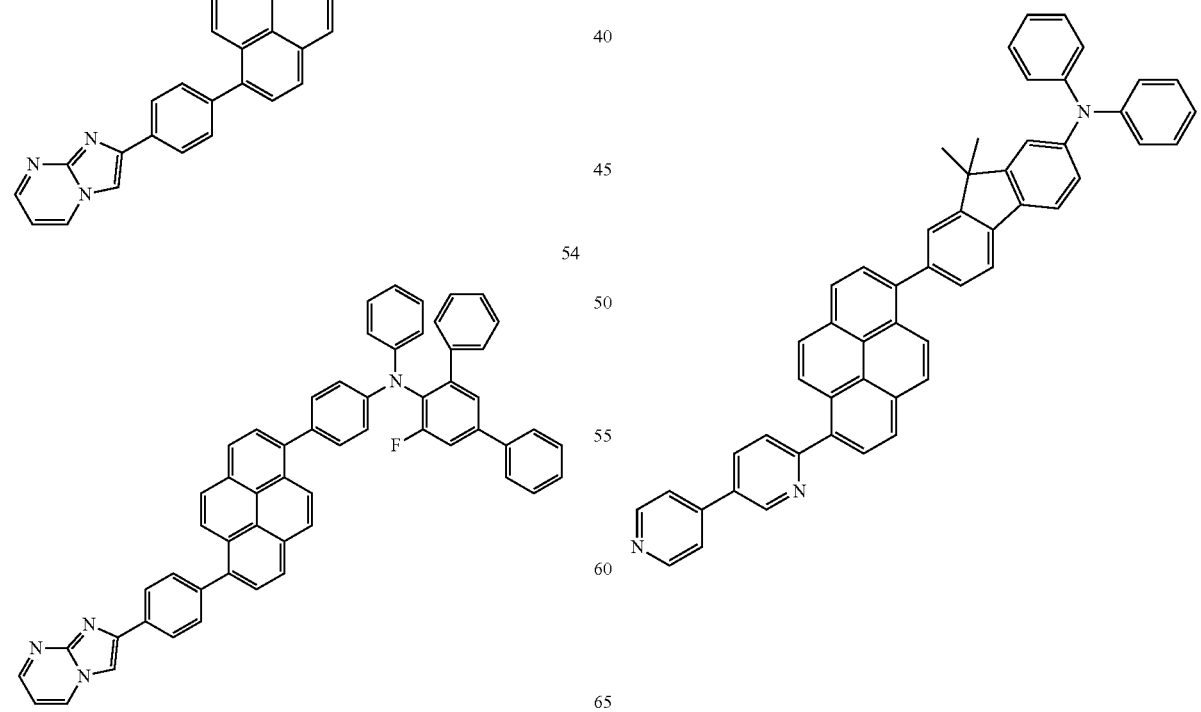
54
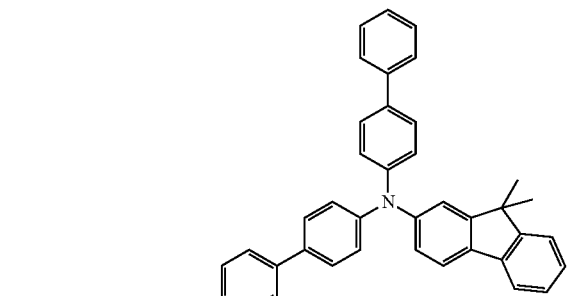
55
56

-continued
57
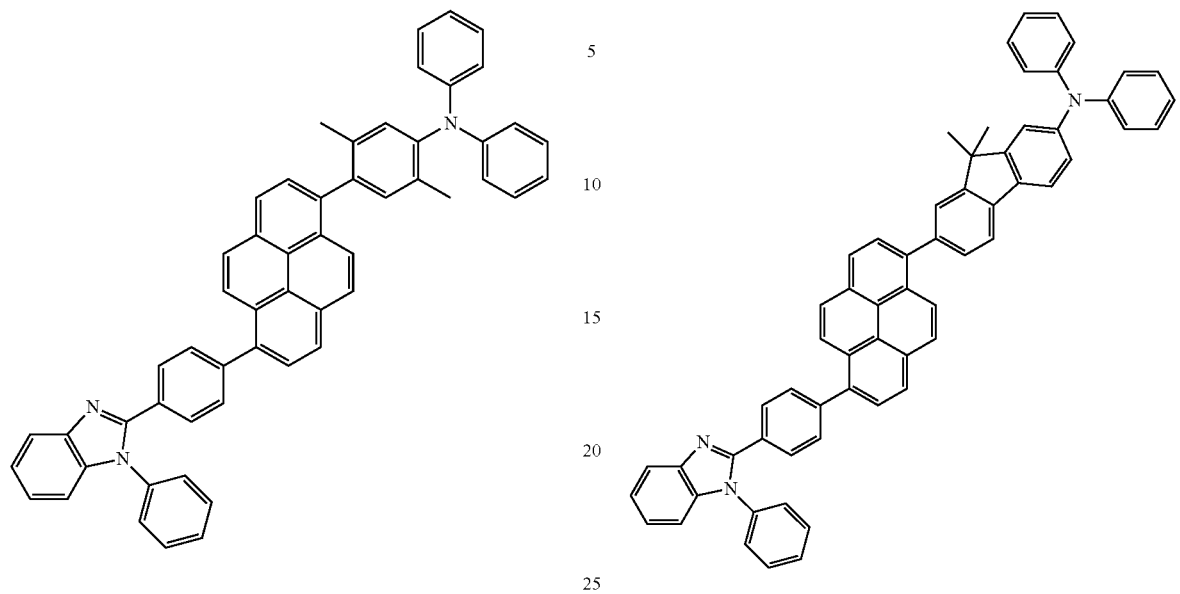
58
-continued
59
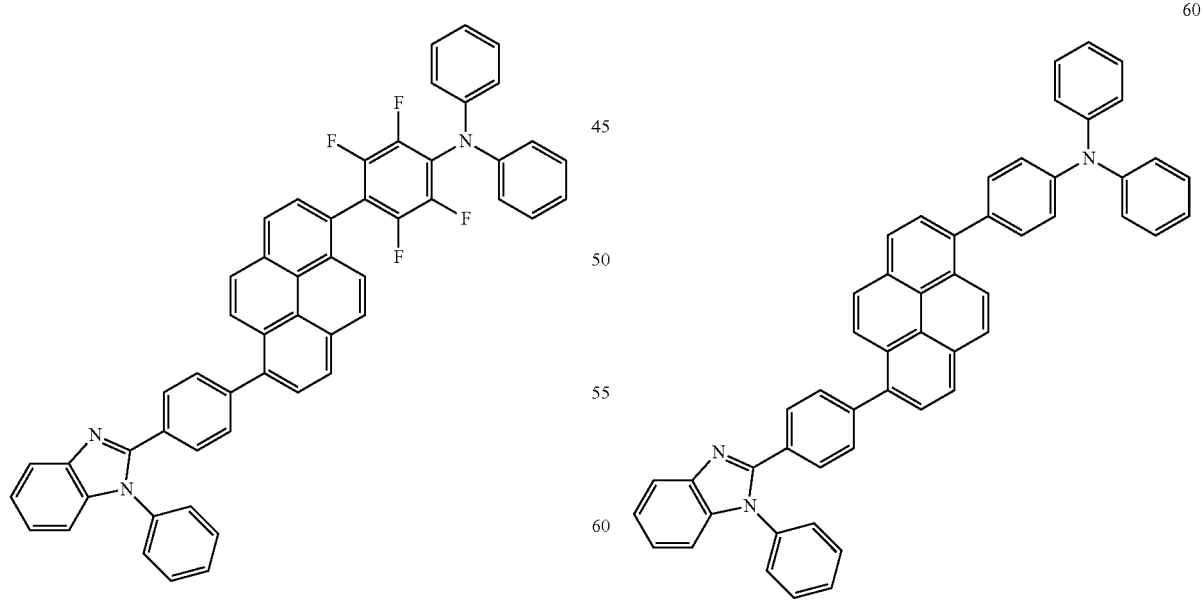
60

61
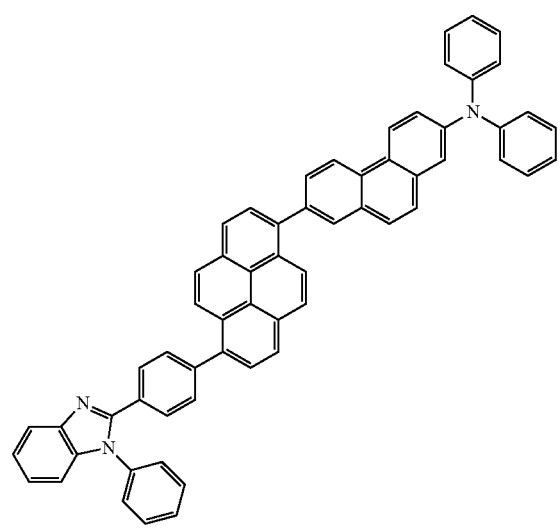
63
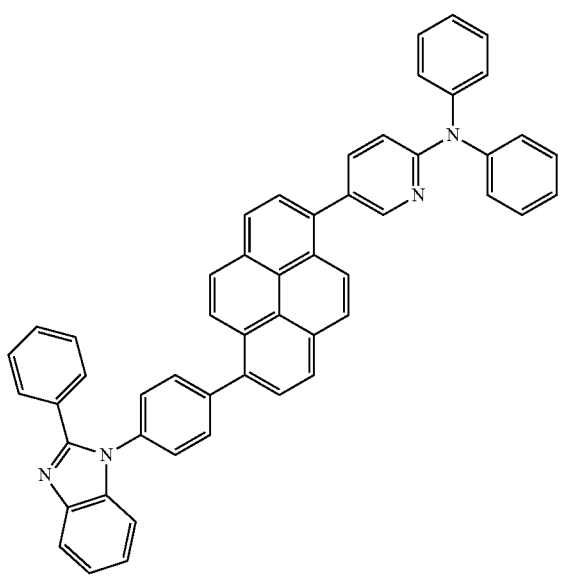
62
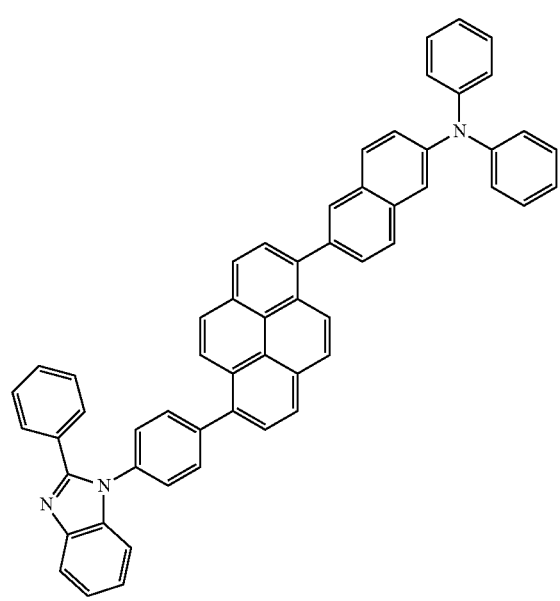
64
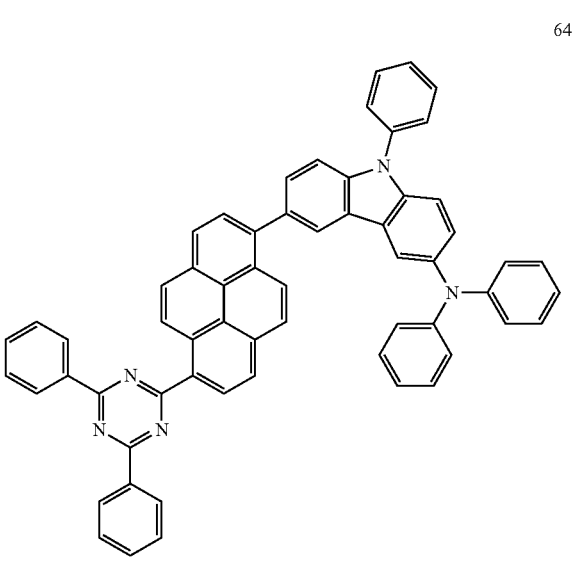

-continued
65
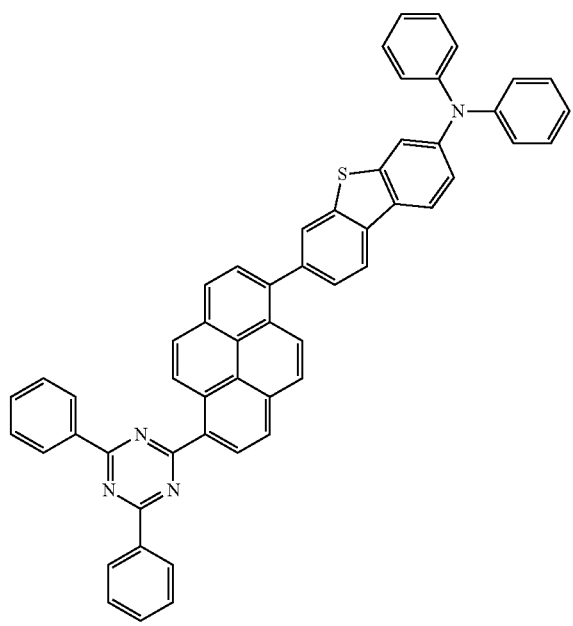
66
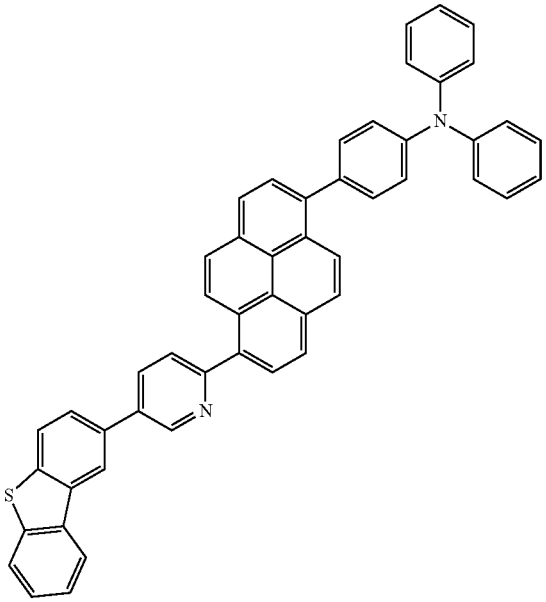
68
67
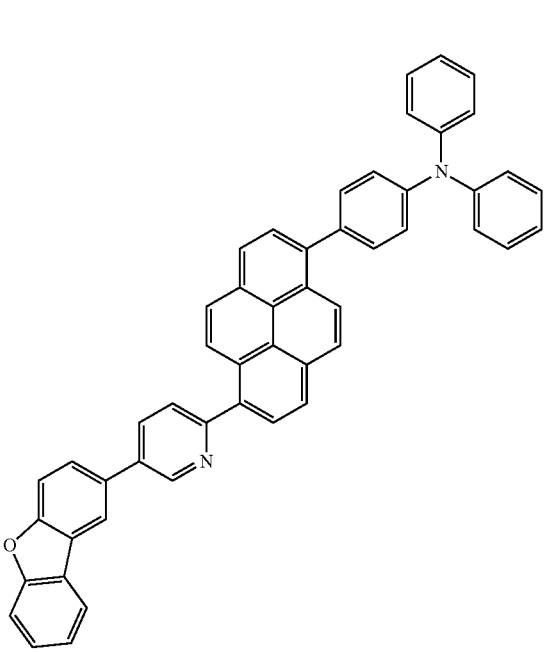
69

-continued

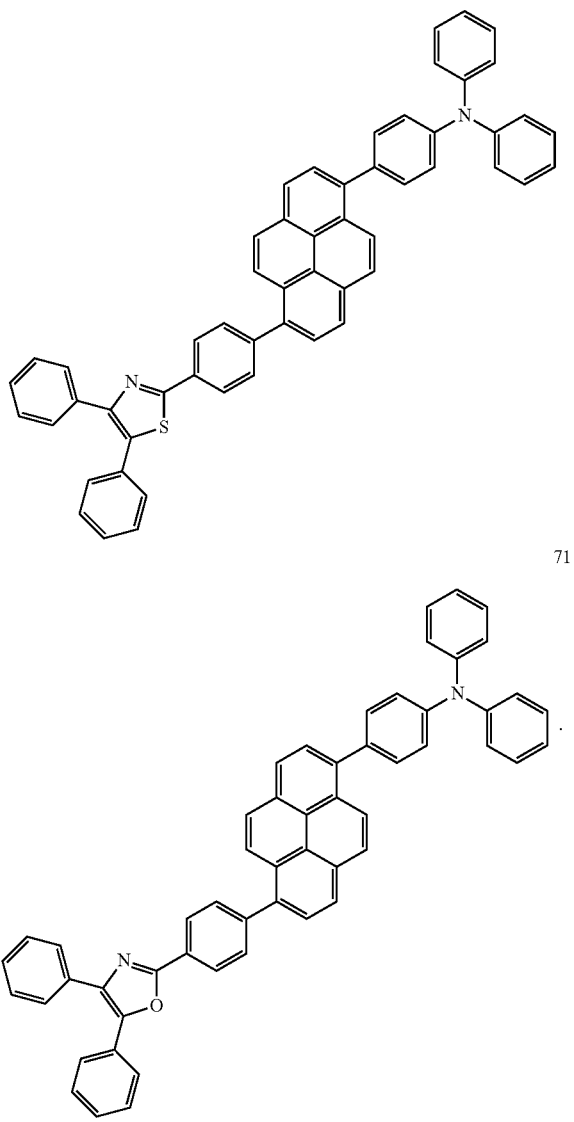

At least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_2$-$C_{60}$ heteroaryl group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_6$-$C_{60}$ aryloxy group and the substituted $C_6$-$C_{60}$ arylthio group may be selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —Si($Q_{13}$)($Q_{14}$)($Q_{15}$) wherein $Q_{13}$ to $Q_{15}$ may be each independently selected from a $C_1$-$C_{60}$ alkyl group, a $C_1$-$C_{60}$ alkoxy group, a $C_6$-$C_{60}$ aryl group, and $C_2$-$C_{60}$ heteroaryl group, but is not limited thereto.

In Formula 1, a first carbon of the pyrene core is connected to —N($R_1$)($R_2$), which is an amino group, with a linker -($L_1$)$_a$- therebetween, and a sixth carbon (that is, a carbon which is a distance of 6 carbons away from the first carbon) of the pyrene core is connected to an electron transporting group $R_3$. In some embodiments, the electron transporting group $R_3$ has a linker -($L_2$)$_b$-. According to embodiments herein described, an electron donor and an electron acceptor are both provided in a single molecule and thus, movement and transport of charges may be smoothly performed. As a result, efficiency of an organic light-emitting diode including the compound of Formula 1 may improve.

Furthermore, since $R_1$ and $R_2$ in Formula 1 are not bonded to each other to form a ring (for example, carbazole or the like), stabilization effects of an orbital energy function of the compound molecule of Formula 1 increases and thus, high emission efficiency may be obtained. Accordingly, in embodiments, from among the compounds of Formula 1, compounds having $R_1$ and $R_2$ that are bonded to each other for example, by a single bond, are excluded. That is, in Formula 1, $R_1$ and $R_2$ are not bonded to each other and do not form a ring.

Accordingly, an organic light-emitting diode including the pyrene-based compound represented by Formula 1 may have low driving voltage, high brightness, high efficiency, and a long lifespan.

The pyrene-based compound of Formula 1 may be synthesized, for example, by using a known organic synthesis method or by using an organic synthesis method identifiable to one of ordinary skill in the art in view of following examples.

In one embodiment, the pyrene-based compound of Formula 1 is used between a pair of electrodes of an organic light-emitting diode. For example, the pyrene-based compound may be used in at least one of an emission layer and an electron transport area between the emission layer and a cathode (for example, a hole blocking layer, an electron injection layer, an electron transport layer, or the like).

Accordingly, provided is an organic light-emitting diode including a first electrode, an organic layer on the first electrode, and a second electrode on the organic layer. In one embodiment, the organic layer includes an emission layer and includes at least one of the pyrene-based compound of Formula 1. In one embodiment, the organic layer further includes a hole transport area between the first electrode and the emission layer and an electron transport area between the emission layer and the second electrode. The pyrene-based compound may be in either the electron transport area or the emission layer, or both the electron transport area and the emission layer. Herein, when the pyrene-based compound is in both the electron transport area and the emission layer, the pyrene-based compound included in the electron transport area and the pyrene-based compound included in the emission layer may be identical to or different from each other. That is, each pyrene-based compound may have a same chemical formula within the scope of Formula 1, or each pyrene-based compound may have a different chemical formula within the scope of Formula 1.

The wording "at least one pyrene-based compound" as used herein may refer to one kind of pyrene-based compound represented by Formula 1 or at least two different kinds of pyrene-based compound represented by Formula 1. For example, an element referred to as including "at least one pyrene-based compound" may include one kind of pyrene-based compound represented by Formula 1 or at least two different kinds of pyrene-based compound represented by Formula 1. That is, the element may have a pyrene-based compound having a single formula within the scope of Formula 1, or may have a at least two pyrene-based compounds, each having different formulas within the scope of Formula 1.

For example, in an embodiment, the organic layer includes only Compound 1 as the pyrene-based compound. In one embodiment, Compound 1 may be in an electron transport layer of an organic light-emitting diode. According to another embodiment of the present invention, the organic layer may include Compound 1 and Compound 10 as the pyrene-based compound. In one embodiment, Compound 1 and Compound 10 may be in a single layer (for example, Compound 1 and Compound 10 may all be in an electron transport layer), or different layers (for example, Compound 1 may be in an electron transport layer and Compound 10 may be in an emission layer.)

The hole transport area of the organic layer may include at least one layer selected from a hole injection layer, a hole transport layer, a functional layer having a hole injection function and a hole transport function (hereinafter referred to as "H-functional layer"), a buffer layer, and an electron blocking layer. The electron transport area of the organic layer may include at least one layer selected from a hole blocking layer, an electron transport layer, and an electron injection layer.

The term "organic layer" used herein refers to a single- and/or multi-layer structure between the first electrode and the second electrode of the organic light-emitting diode.

The drawing is a schematic sectional view of an organic light-emitting device 10 according to an embodiment of the present invention. Hereinafter, the structure and manufacturing method of an organic light-emitting device according to an embodiment of the present invention is described in detail with reference to the drawing.

A substrate 11, which may be any suitable substrate that is used in general organic light-emitting devices, for example, a glass substrate or a transparent plastic substrate having mechanical strength, thermal stability, transparency, surface smoothness, ease of handling, and water resistance.

A first electrode 13 may be formed by, for example, depositing or sputtering a material for a first electrode on the substrate 11. When the first electrode 13 is an anode, the material for the first electrode may be selected from materials with a high work function to enable ease of hole injection. The first electrode 13 may be a reflective electrode or a transmission electrode. The material for the first electrode may be a transparent material with high conductivity, and examples of such a material are indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode 13 may be used as a reflective electrode.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a hole transport area that sequentially includes a hole injection layer and a hole transport layer; an emission layer; and an electron transport area that sequentially includes an electron transport layer and an electron injection layer.

A hole injection layer (HIL) may be formed on the first electrode 13 by using various methods, such as vacuum deposition, spin coating, casting, Langmuir-Blodgett (LB) deposition.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

As a material for the HIL, the pyrene-based compound of Formula 1 may be used. Alternatively, a known hole injection material may be used, for example, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris (3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (pani/CSA), or (polyaniline)/poly(4-styrenesulfonate) (PANI/PSS), but the hole injection material is not limited thereto:

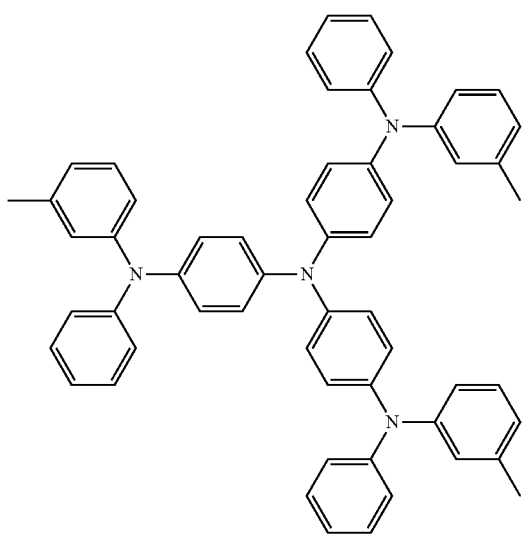

m-MTDATA

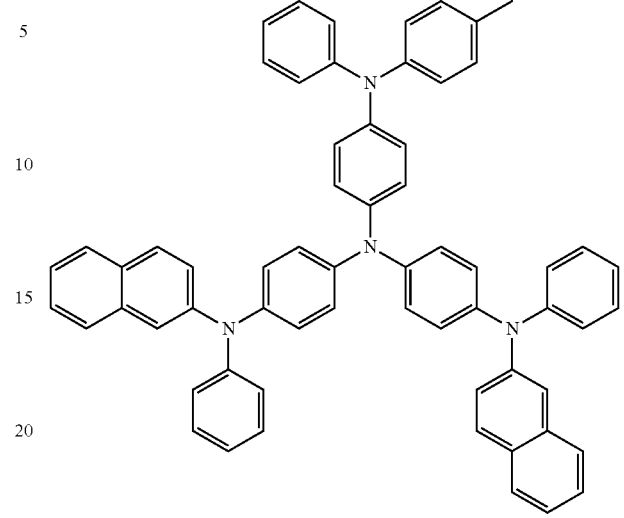

2-TNATA

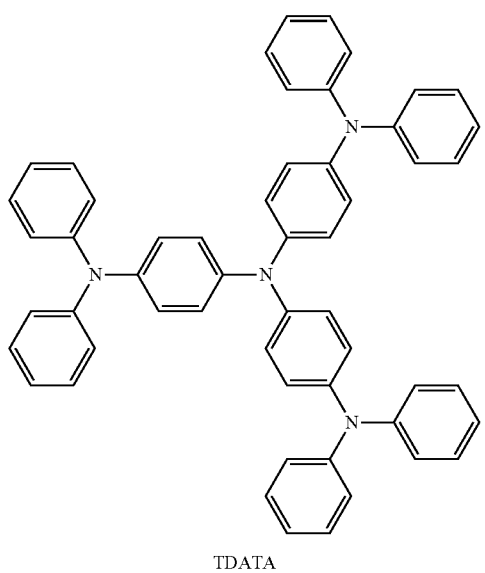

TDATA

In an embodiment, a thickness of the HIL is in a range of about 100 Å to about 10000 Å. In another embodiment, the thickness of the HIL is in a range of about 100 Å to about 1000 Å. In one embodiment, when the thickness of the HIL is within the range described above, the HIL has good hole injection characteristics without a substantial increase in a driving voltage.

Then, a hole transport layer (HTL) may be formed on the HIL by using vacuum deposition, spin coating, casting, LB deposition, or the like. When the HTL is formed using vacuum deposition or spin coating, the deposition and coating conditions may be similar to those for the formation of the HIL, though the deposition and coating conditions may vary according to a compound that is used to form the HTL.

As a material for the HTL, the pyrene-based compound of Formula 1 may be used. Alternatively, as a known material for a HTL, a carbazole derivative, such as N-phenylcarbazole, or polyvinylcarbazole, N,N'-bis(3-methylphenyl)-N,N'-diphenyl-[1,1-biphenyl]-4,4'-diamine (TPD, shown below), 4,4',4"-tris(N-carbazolyl)triphenylamine (TCTA), N,N'-di(1-naphthyl)-N,N'-diphenylbenzidine (NPB, shown below), or the like may be used, but the material for the HTL is not limited thereto.

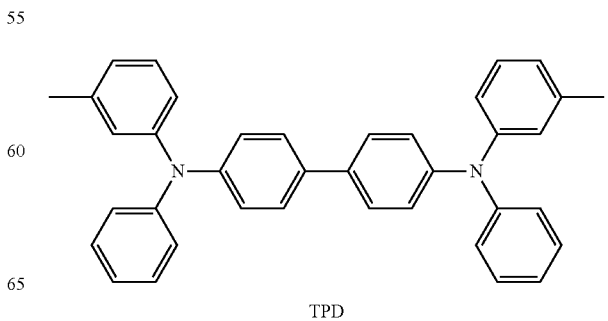

TPD

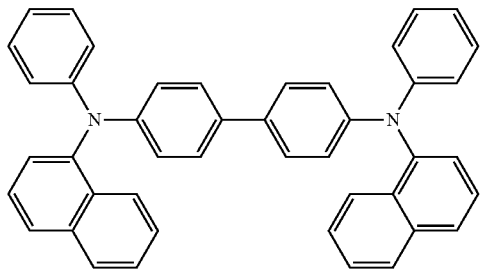

NPB

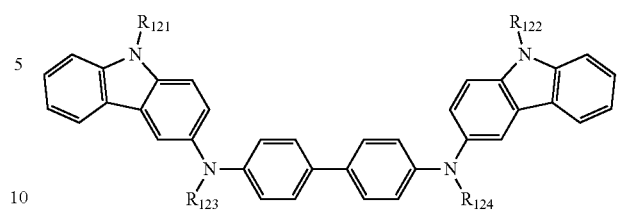

Formula 301

In an embodiment, a thickness of the HTL is in a range of about 50 Å to about 20000 Å. In another embodiment, the thickness of the HTL is in a range of about 100 Å to about 1500 Å. In one embodiment, when the thickness of the HTL is within the range described above, the HTL has good hole transport characteristics without a substantial increase in a driving voltage.

The organic light-emitting diode 10 may include, instead of the HIL and the HTL, the H-functional layer (a functional layer having a hole injection function and a hole transport function). The H-functional layer may include one or more materials selected from the materials for the HIL and the materials for the HTL. In an embodiment, a thickness of the H-functional layer is in a range of about 100 Å to about 10000 Å. In another embodiment, the thickness of the H-functional layer about 100 Å to about 1000 Å. In one embodiment, when the thickness of the H-functional layer is within the range described above, the H-functional layer has good hole injection and transport characteristics without a substantial increase in a driving voltage.

In addition, at least one layer of the hole injection layer, the hole transport layer, and the H-functional layer may include at least one of a compound represented by Formula 300 below and a compound represented by Formula 301 below:

Formula 300

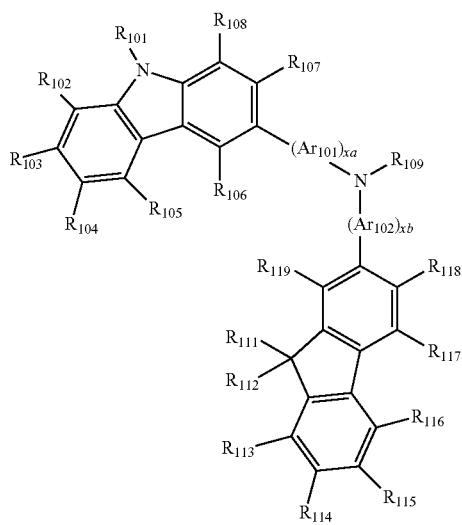

$Ar_{101}$ and $Ar_{102}$ in Formula 300 may be each independently selected from a substituted or unsubstituted $C_6$-$C_{60}$ arylene group. For example, $Ar_{101}$ and $Ar_{102}$ may be each independently phenylene, pentalenylene, indenylene, naphtylene, azulenylene, heptalenylene, a substituted or unsubstituted acenaphtylene, fluorenylene, phenalenylene, phenanthrenylene, anthrylene, fluoranthenylene, triphenylenylene, pyrenylene, chrysenylene, naphthacenylene, picenylene, perylenylene and pentacenylene; and phenylene, pentalenylene, indenylene, naphtylene, azulenylene, heptalenylene, substituted or unsubstituted acenaphtylene, fluorenylene, phenalenylene, phenanthrenylene, anthrylene, fluoranthenylene, triphenylenylene, pyrenylene, chrysenylene, naphthacenylene, picenylene, perylenylene, and pentacenylene, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group.

xa and xb in Formula 300 may be each independently an integer from 0 to 5, or 0, 1 or 2. For example, xa may be 1 and xb may be 0, but xa and xb are not limited thereto.

$R_{101}$ to $R_{108}$, $R_{111}$ to $R_{119}$ and $R_{121}$ to $R_{124}$ in Formulae 300 and 301 may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$ and $R_{71}$, and $R_{72}$ may be each independently selected from a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like);

a $C_1$-$C_{10}$ alkyl group and a $C_1$-$C_{10}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group; a naphthyl group; an anthryl group; a fluorenyl group; a pyrenyl group;

a phenyl group, a naphthyl group, an anthryl group, a fluorenyl group, and a pyrenyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group, but are not limited thereto.

$R_{109}$ in Formula 300 may be selected from a phenyl group; a naphthyl group; an anthryl group; a biphenyl group; a pyridyl group; and a phenyl group, a naphthyl group, an anthryl group, a biphenyl group and a pyridyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{20}$ alkyl group, and substituted or unsubstituted $C_1$-$C_{20}$ alkoxy group.

According to an embodiment of the present invention, the compound represented by Formula 300 may be represented by Formula 300A below, but the compound is not limited to the compound of Formula 300A:

Formula 300A

A detailed description of $R_{101}$, $R_{111}$, $R_{112}$ and $R_{109}$ in Formula 300A is already described above.

For example, at least one layer of the HIL, the HTL, and the H-functional layer may include at least one of Compounds 301 to 320, but is not limited thereto:

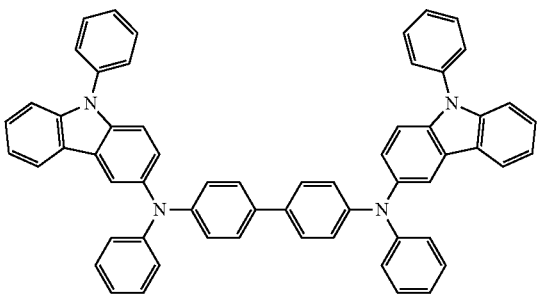

301

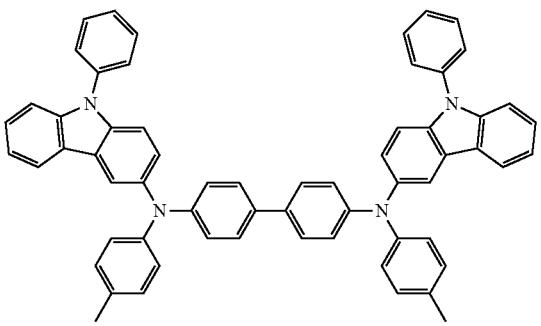

302

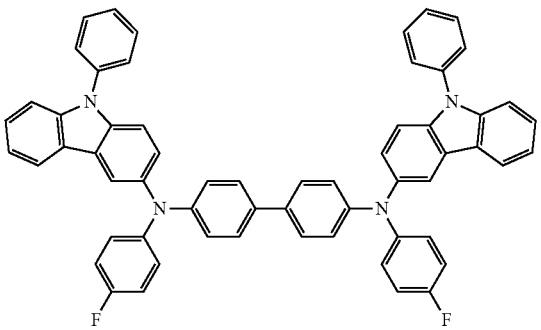

303

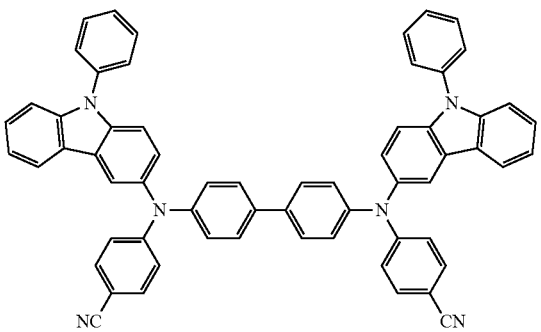

304

305
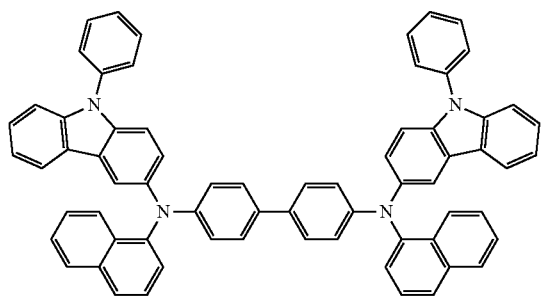
306
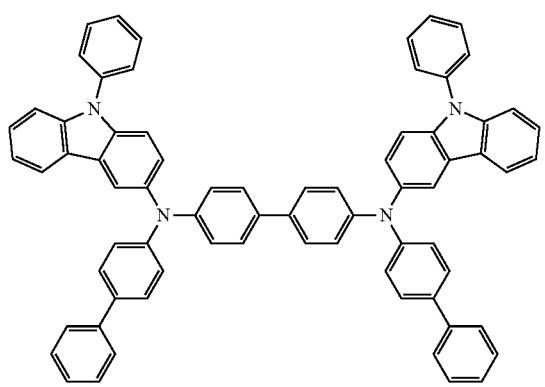
307
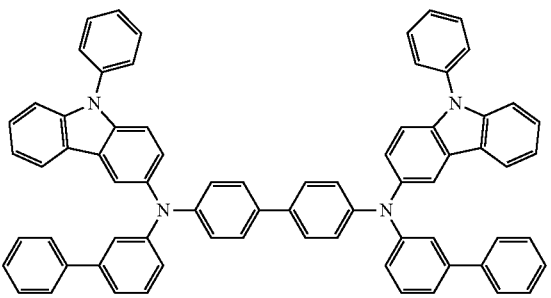
308
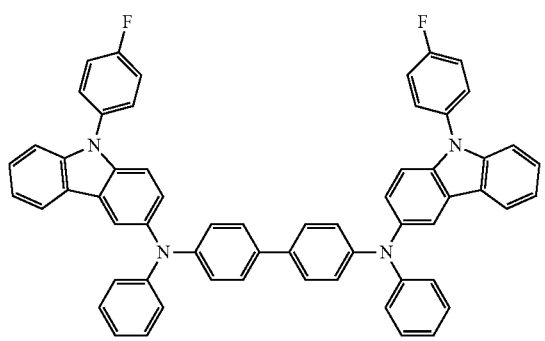
309
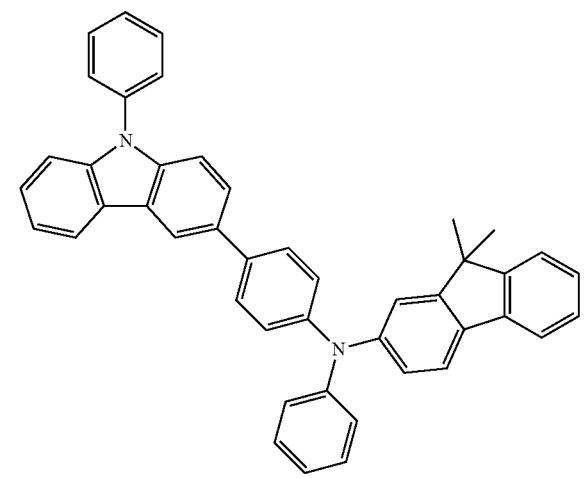
310
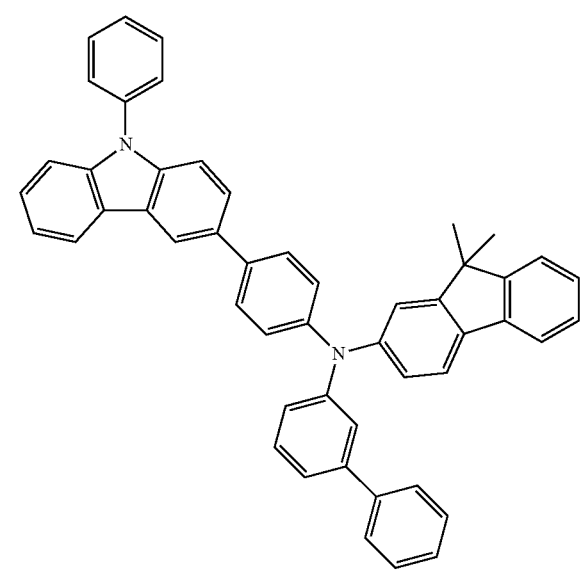

311
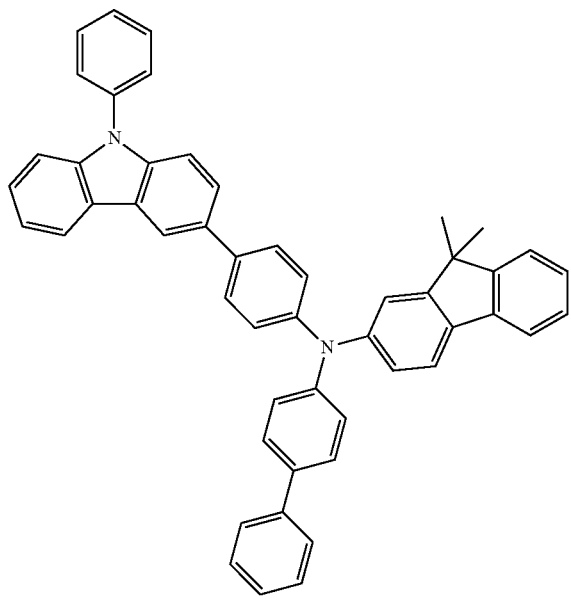
312
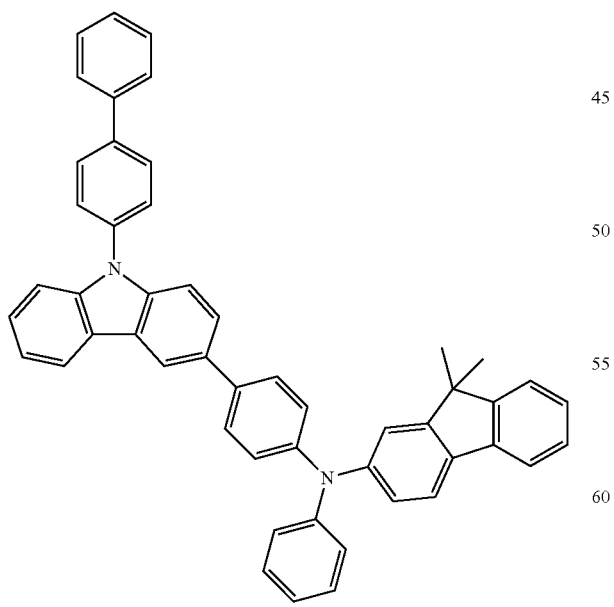
313
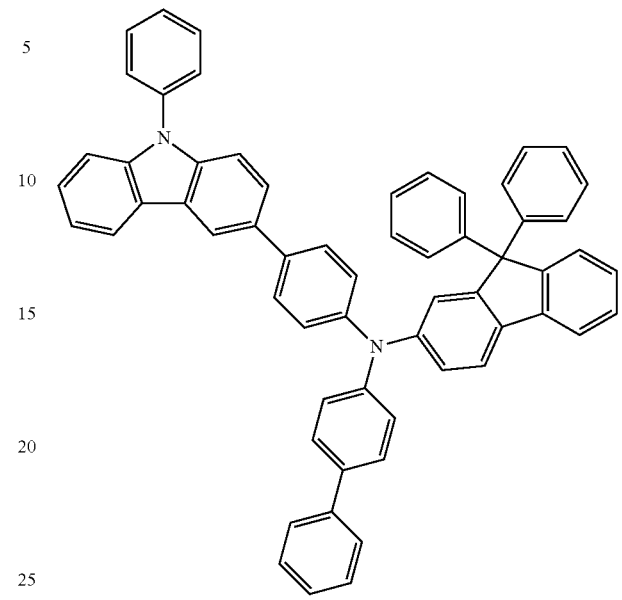
314
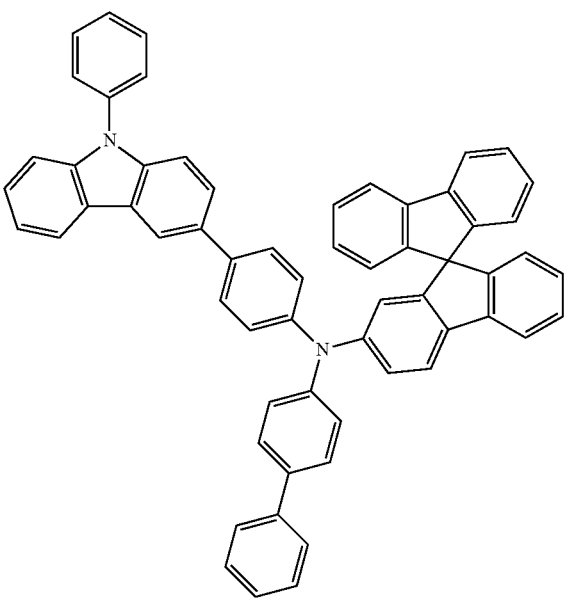

315
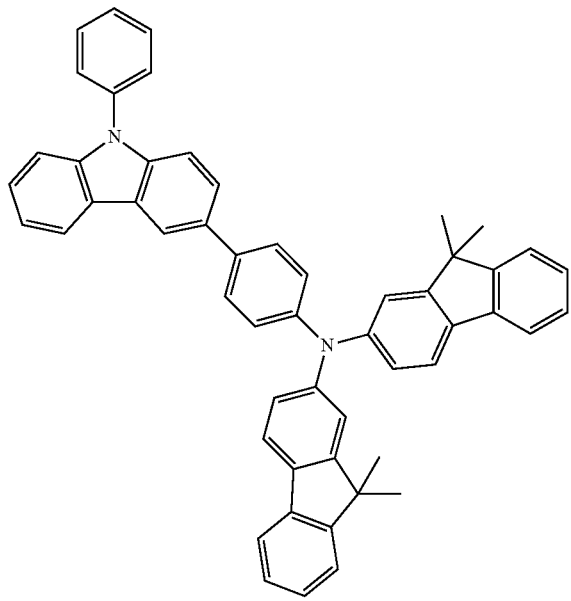
316
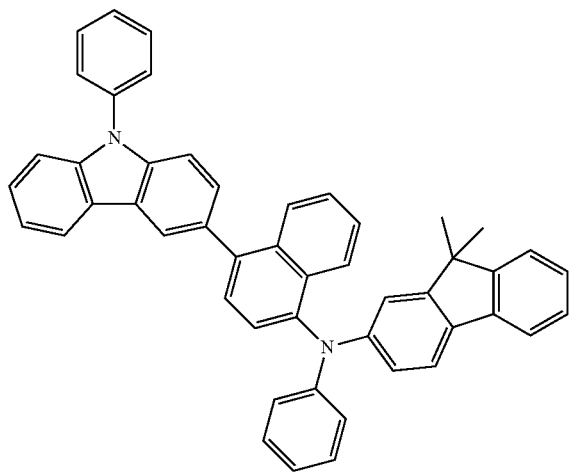
317
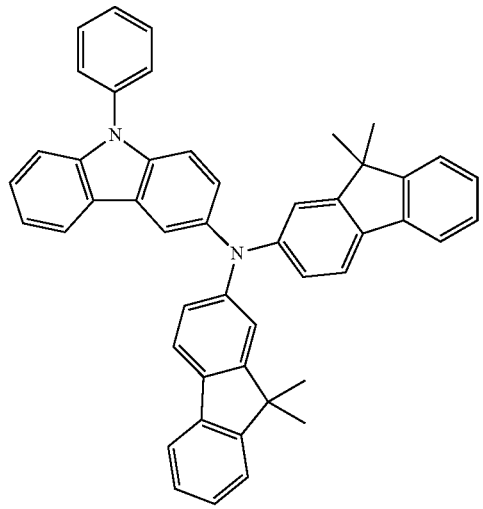
318
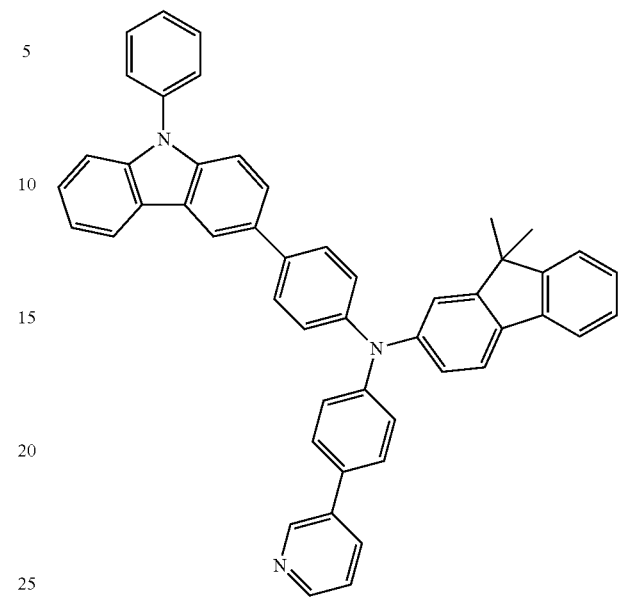
319
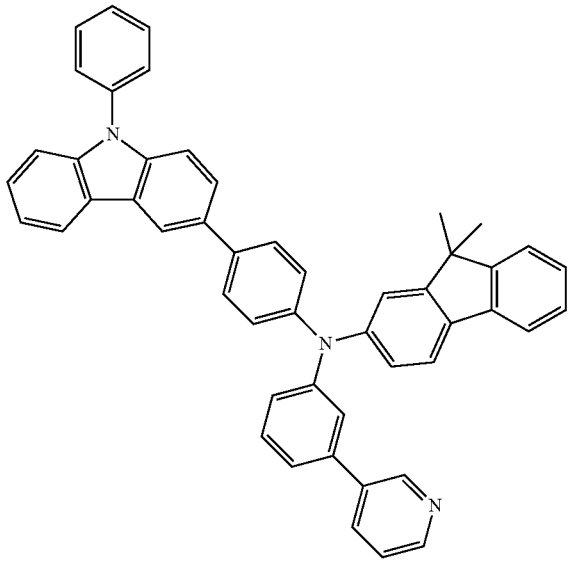

-continued

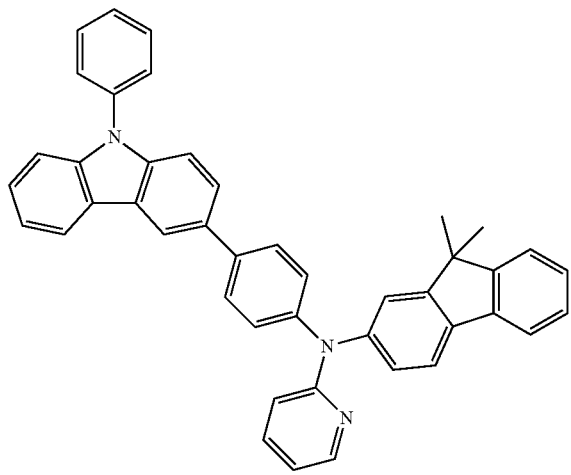

320

The hole transport area may further include, in addition to known hole injection materials and/or known hole transport materials, a charge-generation material to improve conductivity of a film.

The charge-generating material may be, for example, a p-dopant. The p-dopant may be one of quinine derivatives, metal oxides, and compounds with a cyano group, but is not limited thereto. Non-limiting examples of the p-dopant include a quinine derivative, such as tetracyanoquinodimethane (TCNQ) and 2,3,5,6-tetrafluoro-tetracyano-1,4-benzoquinodimethane (F4-TCNQ); a metal oxide, such as tungsten oxide and molybdenym oxide; and a cyano group-containing compound, such as Compound 200 below, but is not limited thereto.

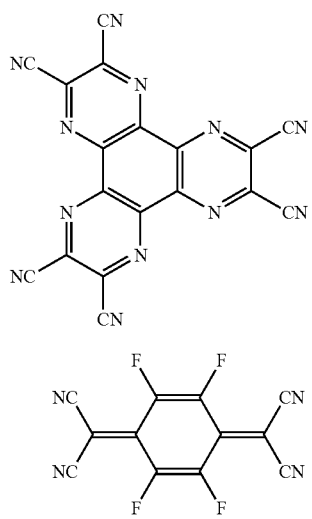

Compound 200

F4-TCNQ

When the hole transport area further includes a charge-generation material, the charge-generation material may be homogeneously or non-homogeneously dispersed in the hole transport area.

The hole transport area may further include a buffer layer between the HTL and the EML (or between the H-functional layer and the EML).

The buffer layer may compensate for an optical resonance distance of light according to a wavelength of the light emitted from the EML, and thus may increase efficiency. The buffer layer may include any hole injecting material or hole transporting material that are known or used in the art. In some other embodiments, the buffer layer may include the same material as one of the materials included in the HTL (or the H-functional layer) that underlies the buffer layer.

Then, an emission layer (EML) may be formed on the hole transport area by vacuum deposition, spin coating, casting, LB deposition, or the like. When the EML is formed using vacuum deposition or spin coating, the deposition and coating conditions may be similar to those for the formation of the HIL, though the conditions for deposition and coating may vary according to the material that is used to form the EML.

The EML may include a host and a dopant, which may include known hosts and dopants.

As the host, Alq3, 4,4'-N,N'-dicarbazol-biphenyl (CBP), poly(n-vinylcarbazole) (PVK), 9,10-di(naphthalen-2-yl)anthracene (ADN), TCTA, 1,3,5-tris(N-phenylbenzimidazole2-yl)benzene (TPBI), 3-tert-butyl-9,10-di(naphth-2-yl) anthracene (TBADN), E3, distyryl arylene (DSA), dmCBP, and Compounds 501 to 509 below, or the like may be used, but the host is not limited thereto:

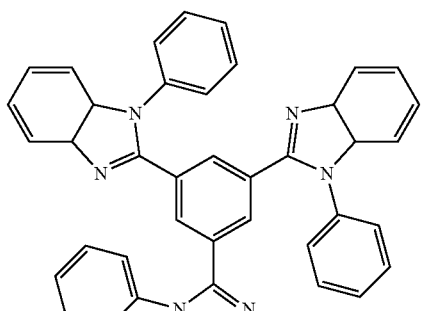

TPBI

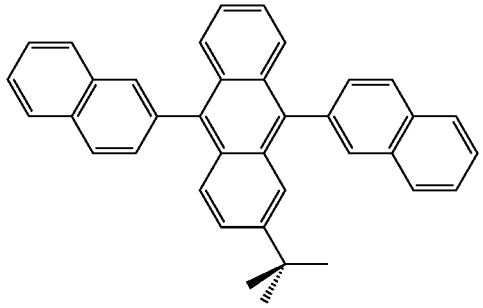

TBADN

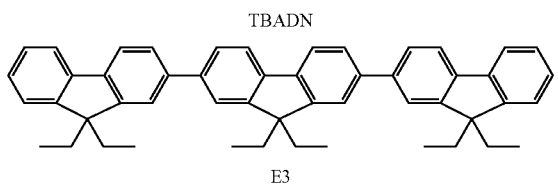

E3

-continued
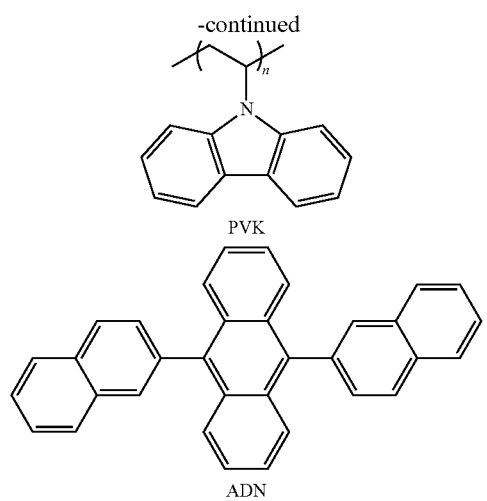
PVK
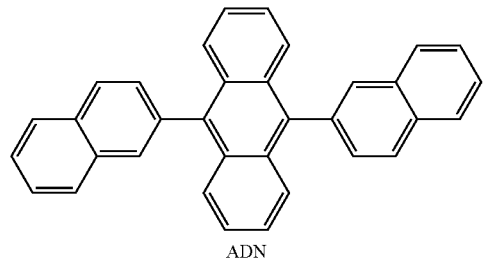
ADN
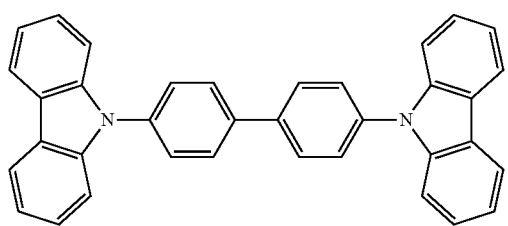
CBP
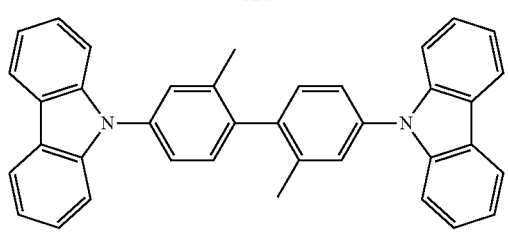
dmCBP
501
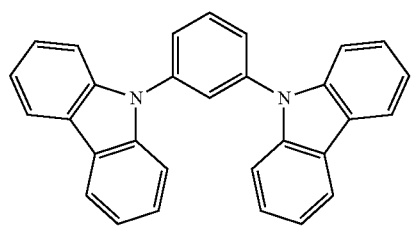
502
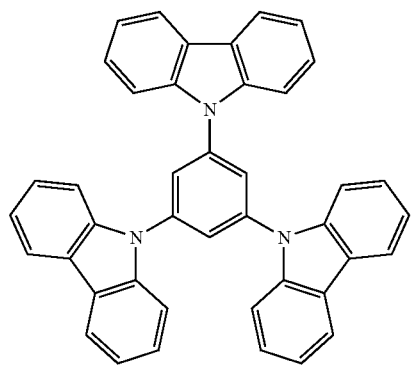
-continued
503
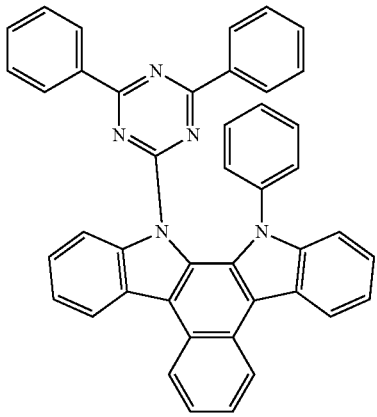
504
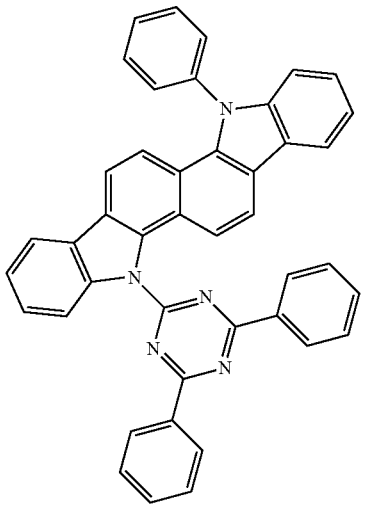
505
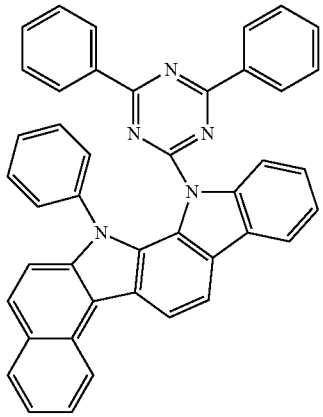

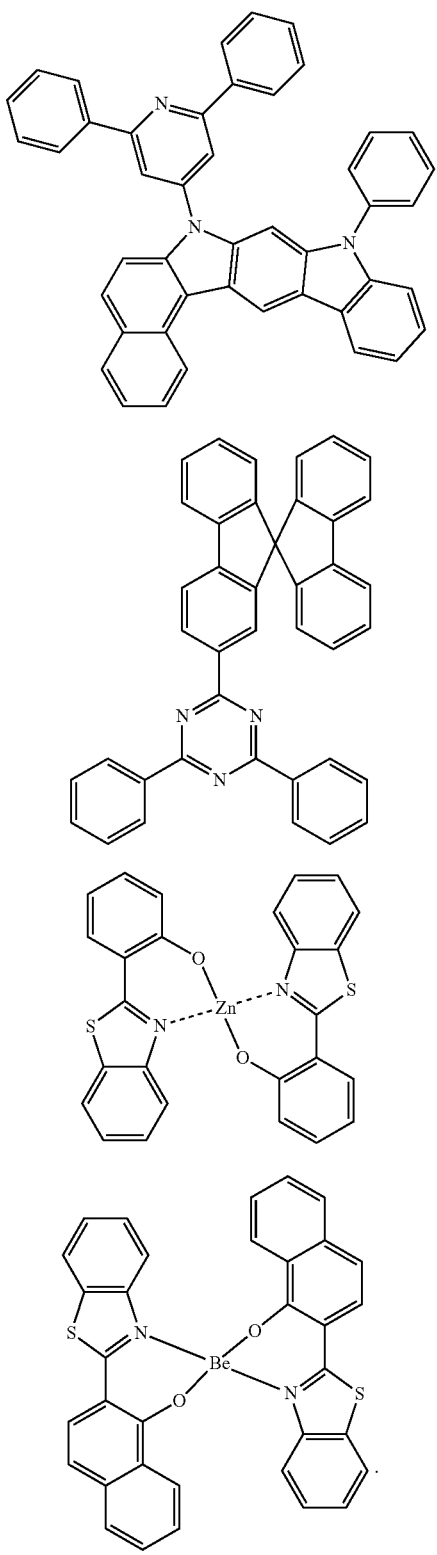

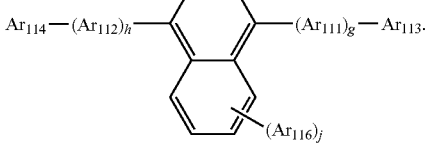

Formula 400

Ar$_{111}$ and Ar$_{112}$ in Formula 400 may be each independently a substituted or unsubstituted C$_6$-C$_{60}$ arylene group; and Ar$_{113}$ to Ar$_{116}$ may be each independently a substituted or unsubstituted C$_1$-C$_{10}$ alkyl group, or a substituted or unsubstituted C$_6$-C$_{50}$ aryl group; and g, h, i, and j may be each independently an integer from 0 to 4.

For example, Ar$_{111}$ and Ar$_{112}$ in Formula 400 may be phenylene, naphtylene, phenanthrenylene, or pyrenylene; or phenylene, naphtylene, phenanthrenylene, fluorenyl group, or pyrenylene, each substituted with at least one substituent selected from a phenyl group, a naphthyl group and an anthryl group, but is not limited thereto.

g, h, i and j in Formula 400 may be each independently 0, 1, or 2.

Ar$_{113}$ to Ar$_{116}$ in Formula 400 may be each independently selected from a C$_1$-C$_{10}$ alkyl group, each substituted with at least one substituent selected from a phenyl group, a naphthyl group, and an anthryl group;

a phenyl group; a naphthyl group; an anthryl group; a pyrenyl group; a phenanthrenyl group; a fluorenyl group;

a phenyl group, a naphthyl group, an anthryl group, a pyrenyl group, a phenanthrenyl group and a fluorenyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a phenyl group, a naphthyl group, an anthryl group, a pyrenyl group, a phenanthrenyl group and a fluorenyl group; and

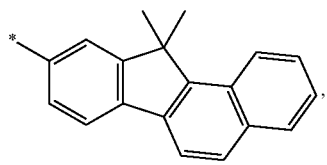 [SMILES: *c1ccc2c(c1)C(C)(C)c1c-2ccc2ccccc12]

but is not limited thereto.

According to an embodiment of the present invention, as the host, an anthracene-based compound represented by Formula 400 below is used:

For example, the anthracene-based compound represented by Formula 400 may be any one of the compounds below, but is not limited thereto:

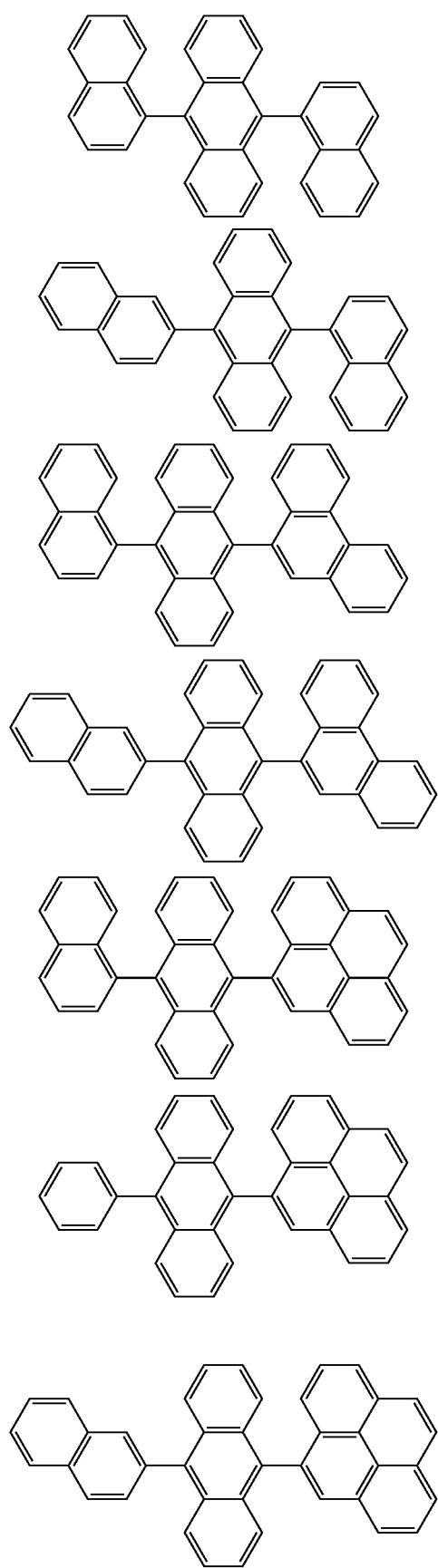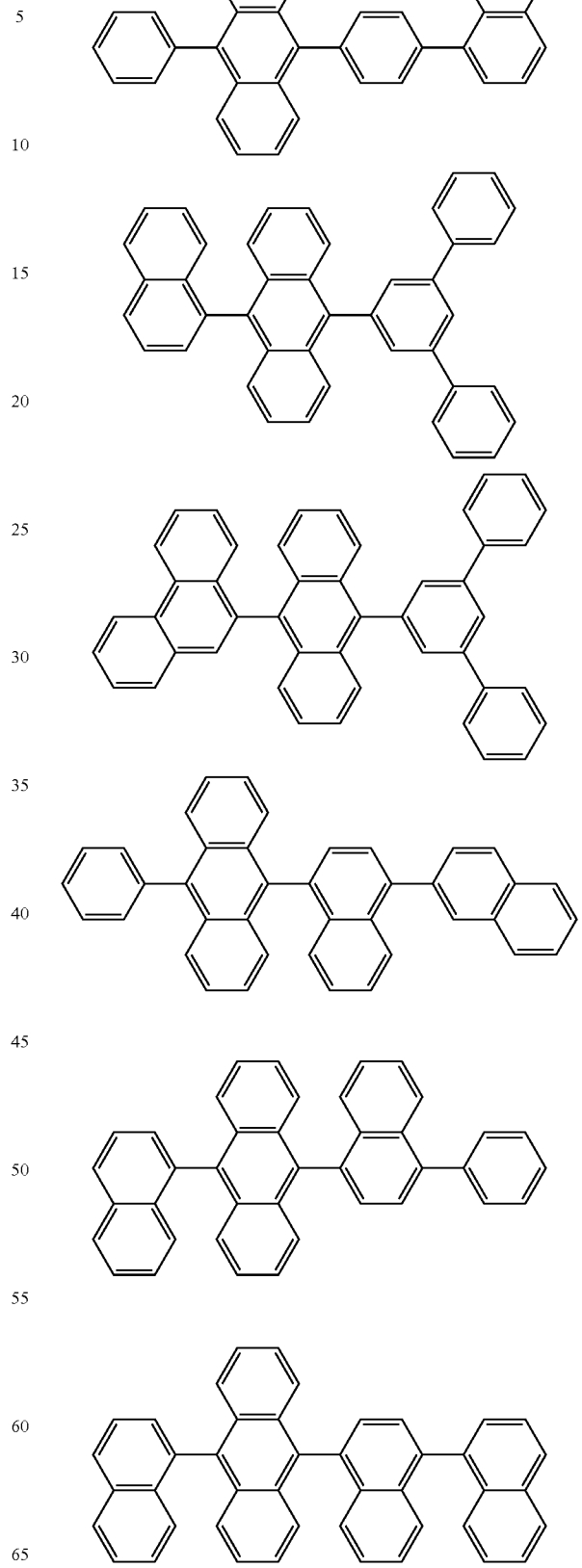

71
-continued
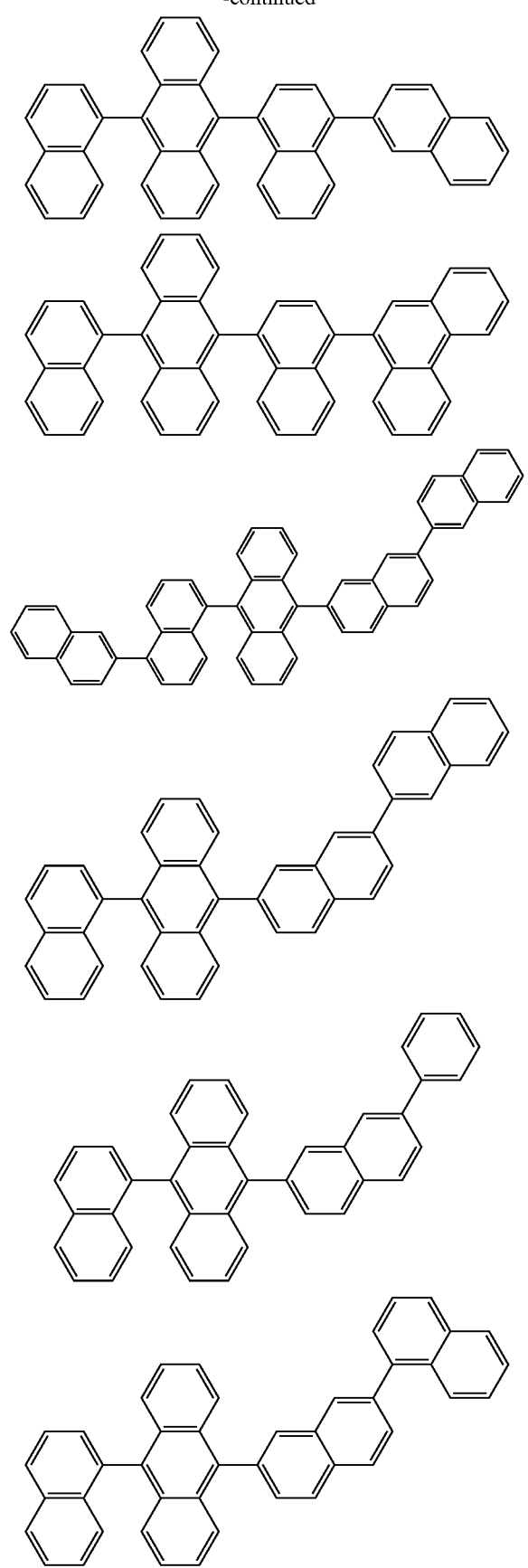
72
-continued
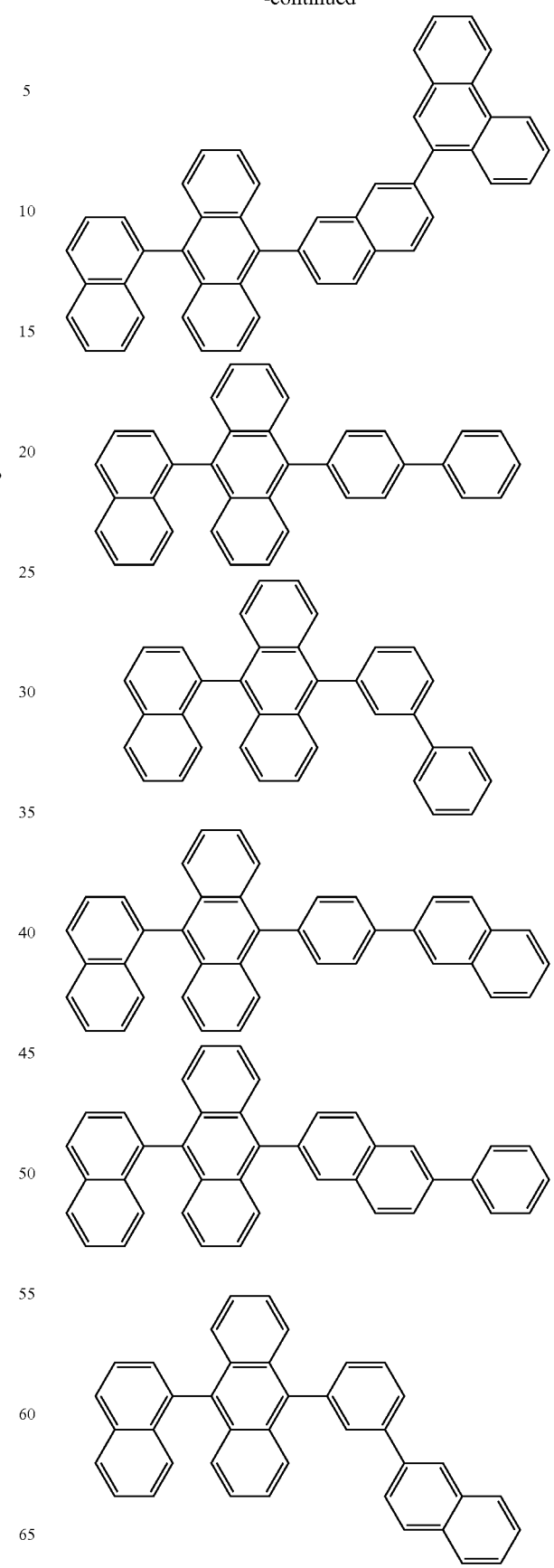

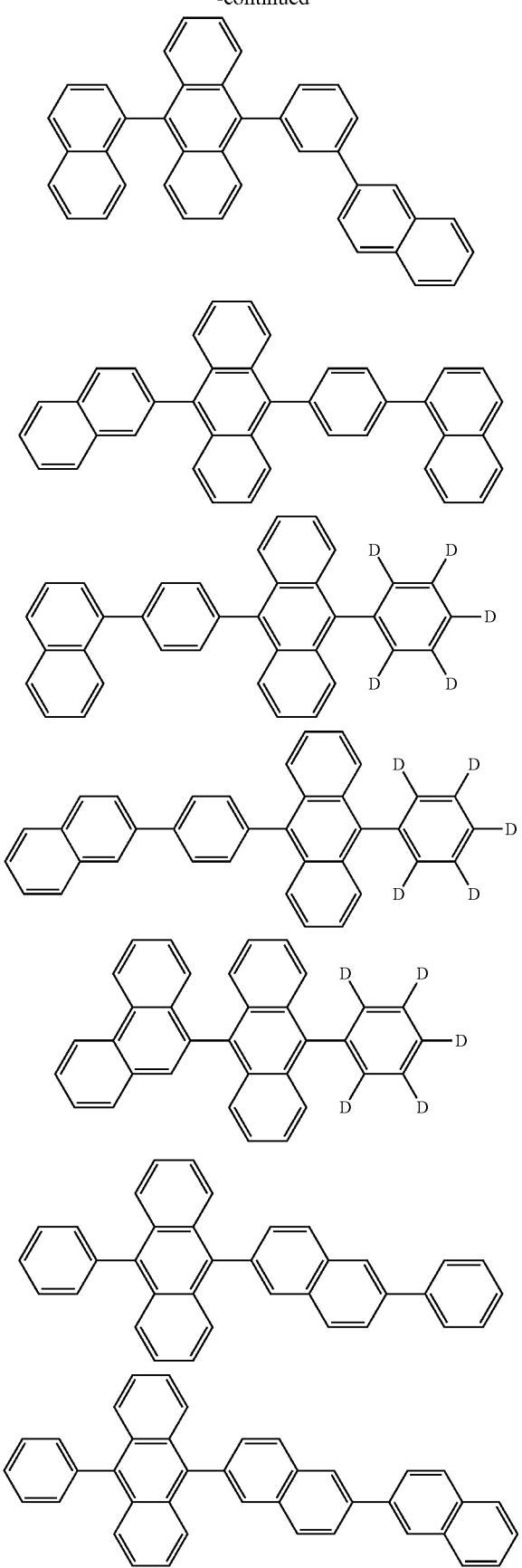

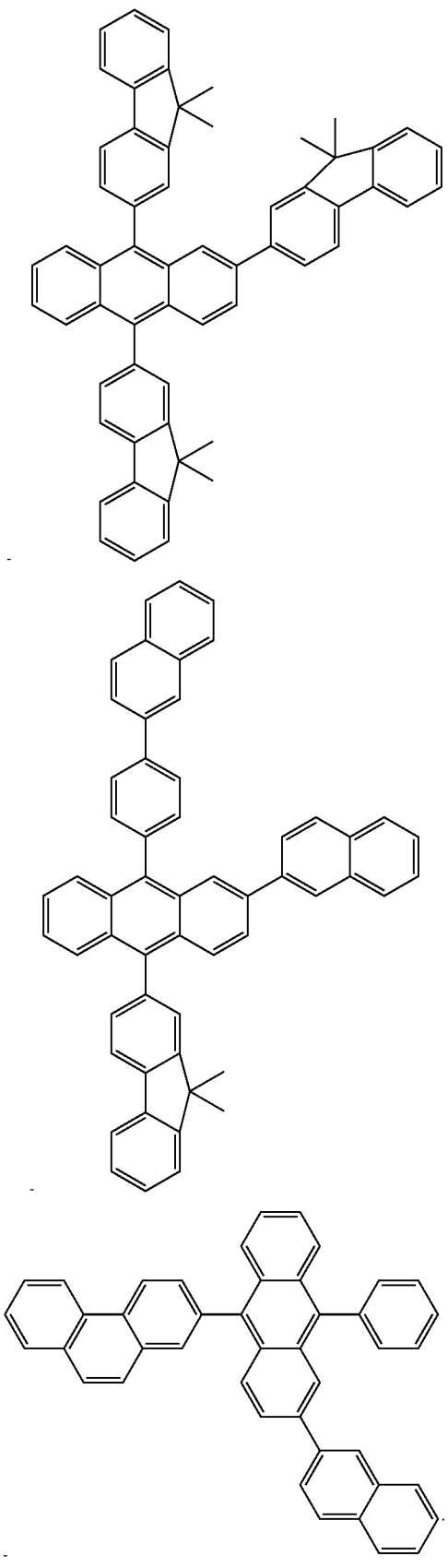

According to another embodiment of the present invention, as the host, an anthracene-based compound represented by Formula 401 below may be used:

Formula 401

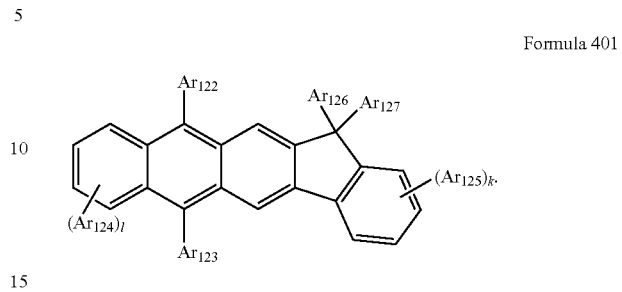

A detailed description of $Ar_{122}$ to $Ar_{125}$ in Formula 401 may include substituents as described with reference to $Ar_m$ in Formulae 400 herein.

$Ar_{126}$ and $Ar_{127}$ in Formula 401 may be each independently a $C_1$-$C_{10}$ alkyl group (for example, a methyl group, an ethyl group, or a propyl group).

k and l in Formula 401 may be each independently an integer from 0 to 4. For example, k and l may be 0, 1, or 2.

For example, the anthracene-based compound represented by Formulae 401 may be one of compounds below, but is not limited thereto:

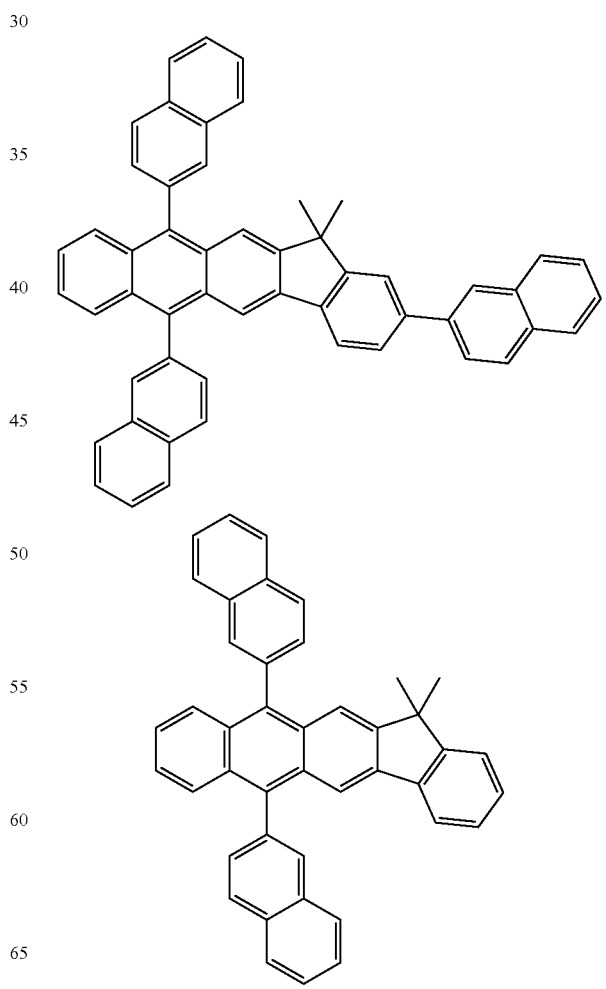

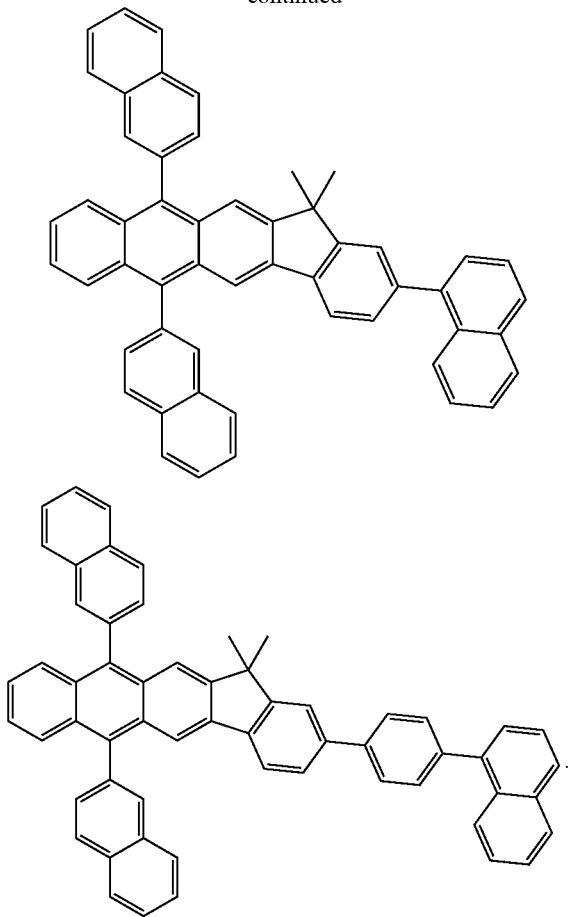

When the organic light-emitting device is a full color organic light-emitting device, the emission layer may be patterned into a red emission layer, a green emission layer, and a blue emission layer. According to another embodiment of the present invention, due to the inclusion of a stack structure including a red EML, a green EML, and/or a blue EML, the EML may emit white light.

The dopant in the EML may be the pyrene-based compound represented by Formula 1. In one embodiment, the pyrene-based compound may act as a fluorescent dopant that emits light according to an emission mechanism. For example, the pyrene-based compound may act as a fluorescent dopant emitting blue light, green light, or bluish green light, but is not limited thereto.

In addition, as a known dopant, dopants illustrated below may be used.

At least one of the red EML, the green EML, and the blue EML may include dopants illustrated below (ppy=phenylpyridine).

For example, compounds illustrated below may be used as a blue dopant, but the blue dopant is not limited thereto:

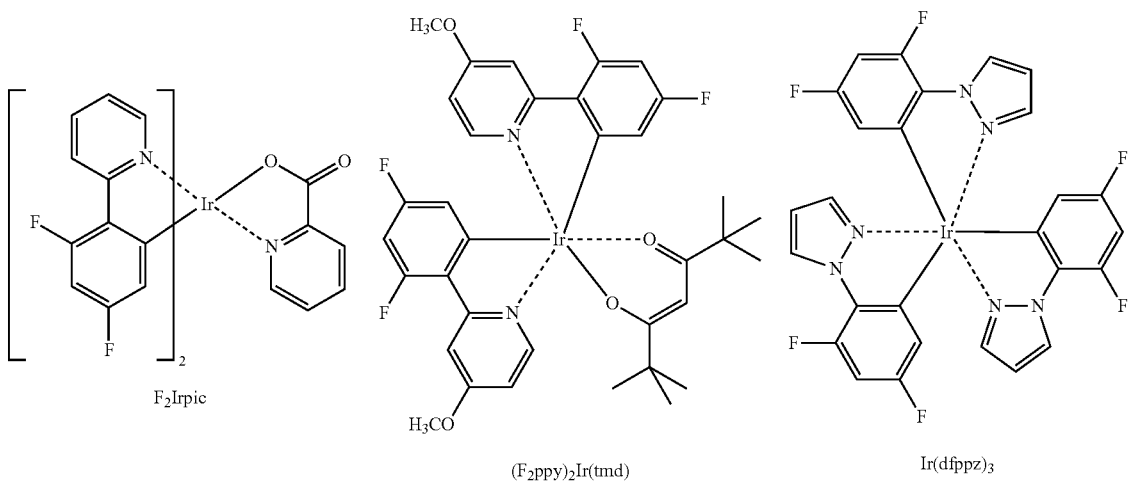

-continued
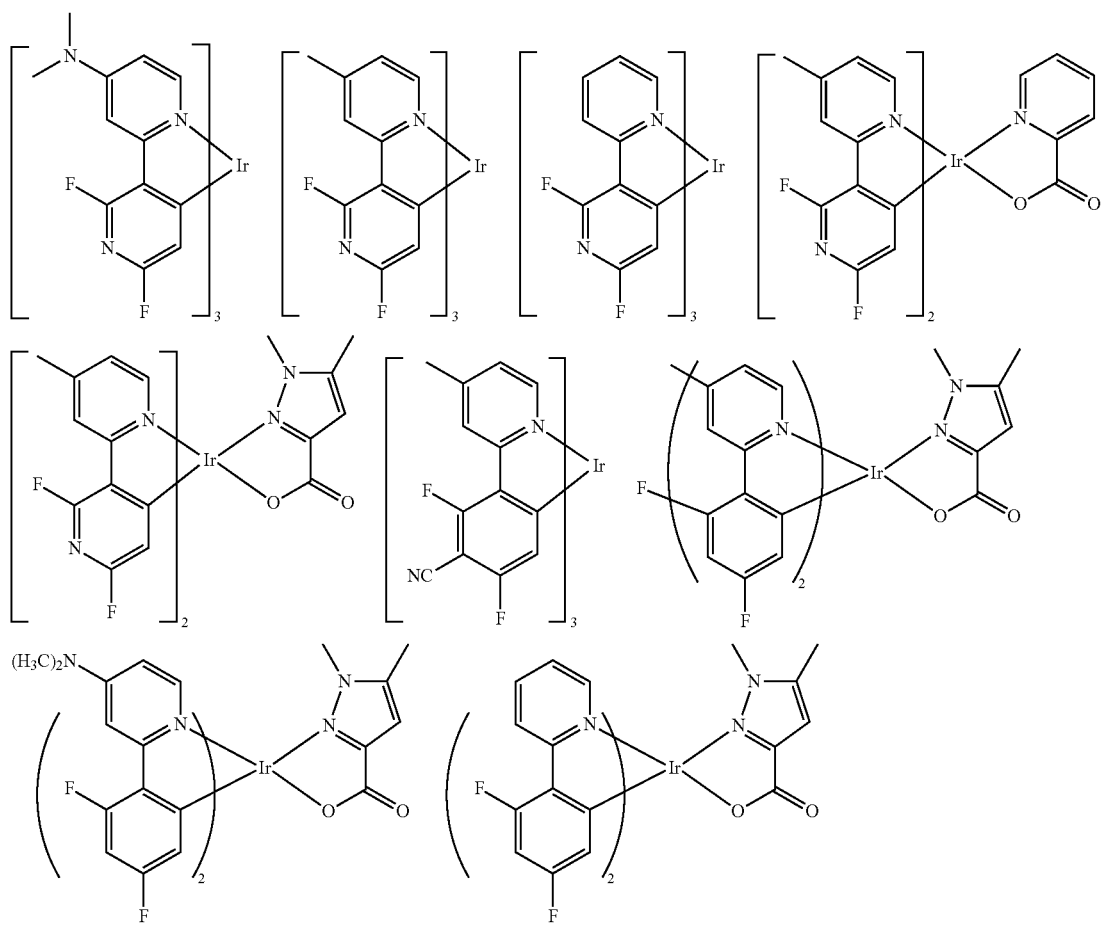
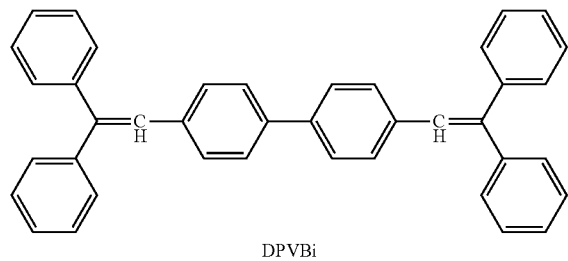
DPVBi
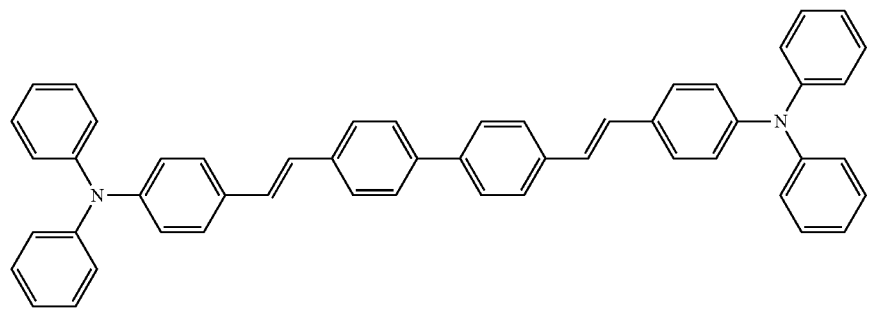
DPAVBi

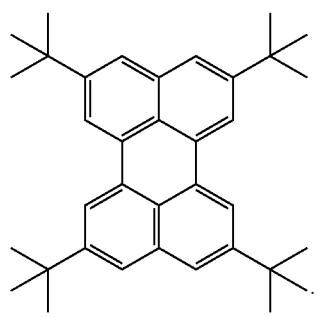
TBPe
For example, compounds illustrated below may be used as a red dopant, but the red dopant is not limited thereto:
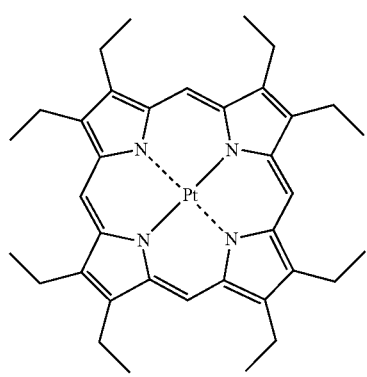
PtOEP
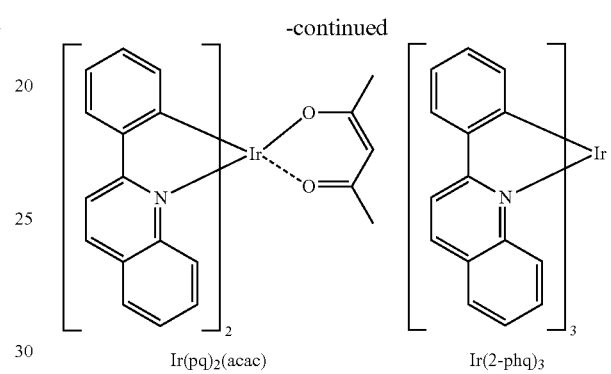
Ir(pq)₂(acac)    Ir(2-phq)₃
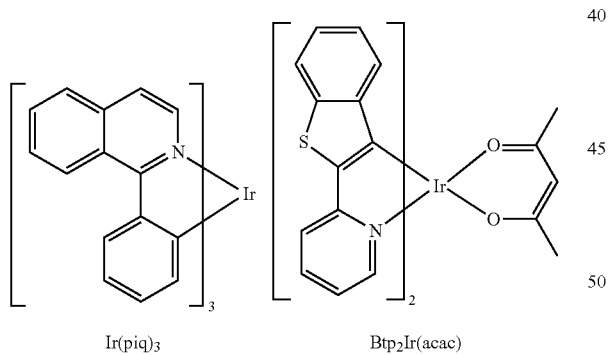
Ir(piq)₃    Btp₂Ir(acac)
Ir(BT)₂(acac)
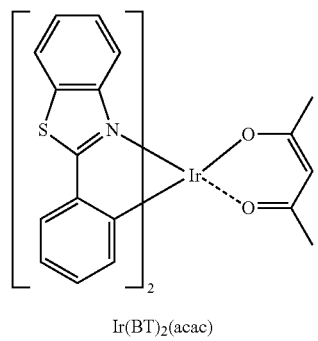
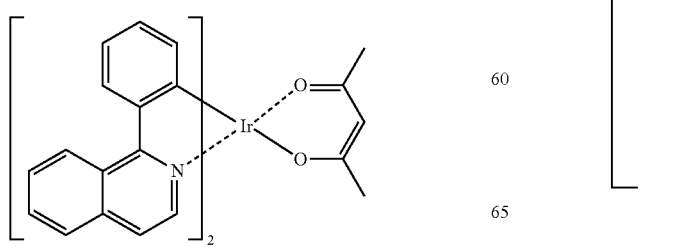
Ir(flq)₂(acac)

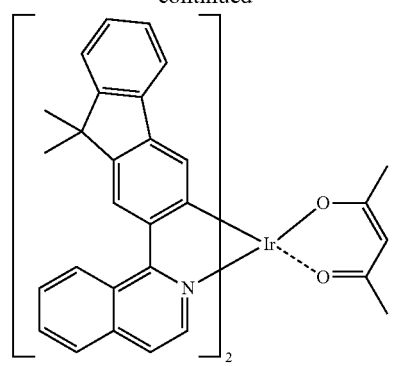

Ir(fliq)₂(acac)

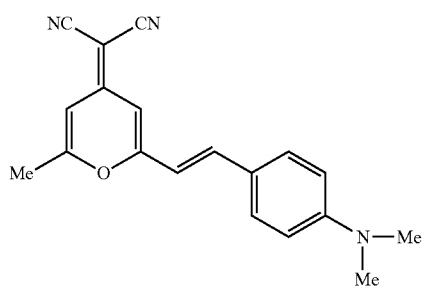

DCM

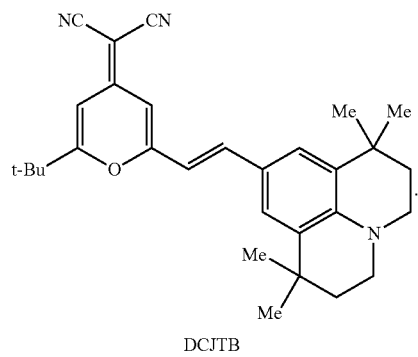 [SMILES: CC(C)(C)C1=CC(=C(C#N)C#N)C=C(/C=C/c2cc3c4c(c2)C(C)(C)CCN4CCC3(C)C)O1]

DCJTB

According to another embodiment of the present invention, DCM or DCJTB may be used as the red dopant.

For example, compounds illustrated below may be used as a green dopant, but the green dopant is not limited thereto:

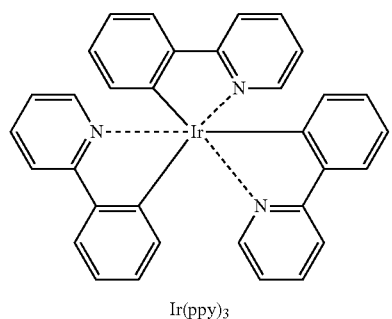

Ir(ppy)₃

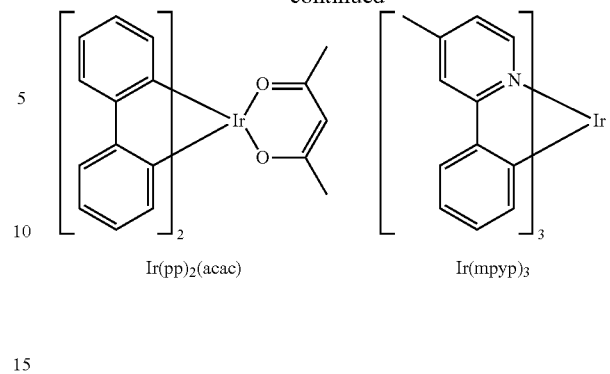

Ir(pp)₂(acac)    Ir(mpyp)₃

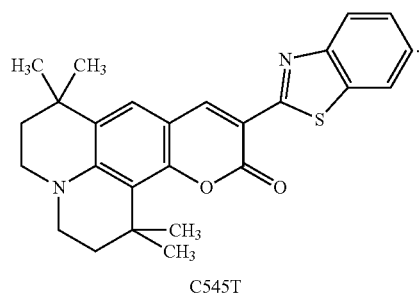

C545T

For example, C545T may be used as the green dopant.

Non-limiting examples of the dopant that may be used in the EML are complexes represented by the following formulae:

D1

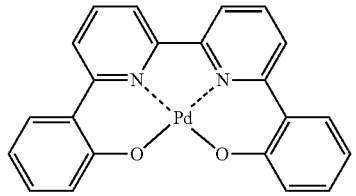

D2

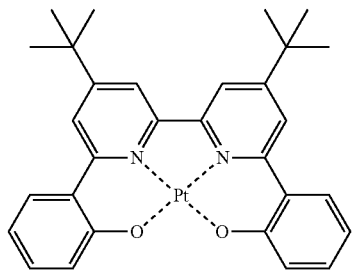

D3

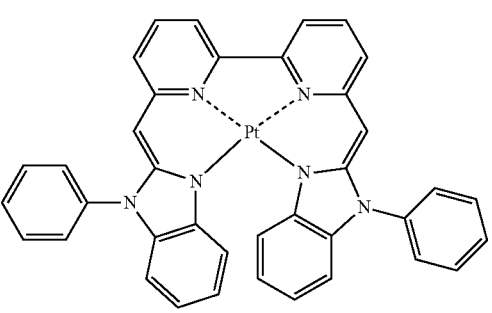

-continued
D4
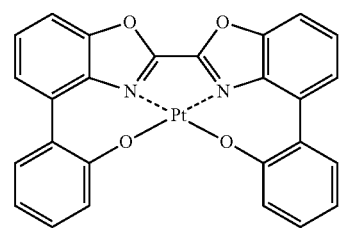
D5
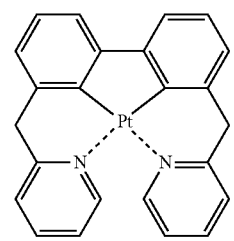
D6
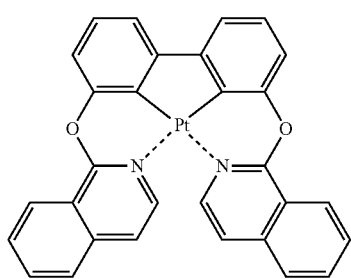
D7
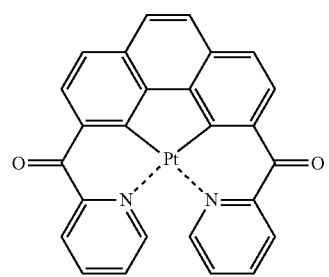
D8
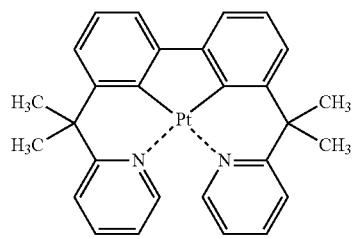
D9
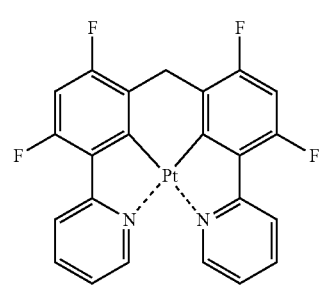
-continued
D10
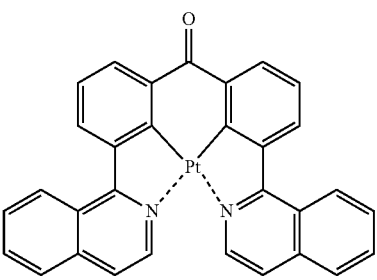
D11
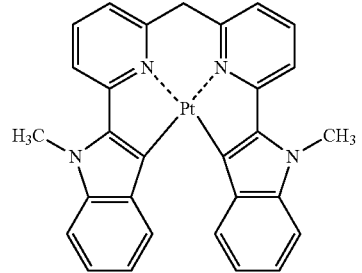
D12
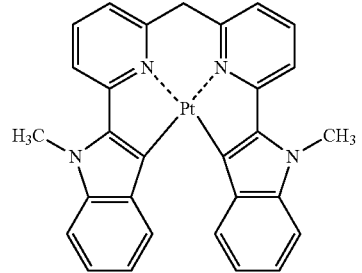
D13
D14
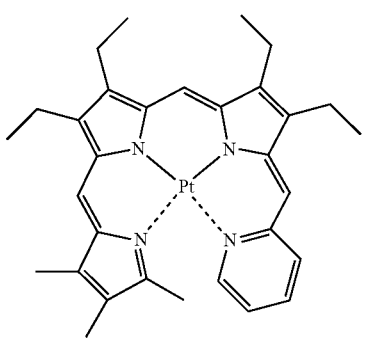

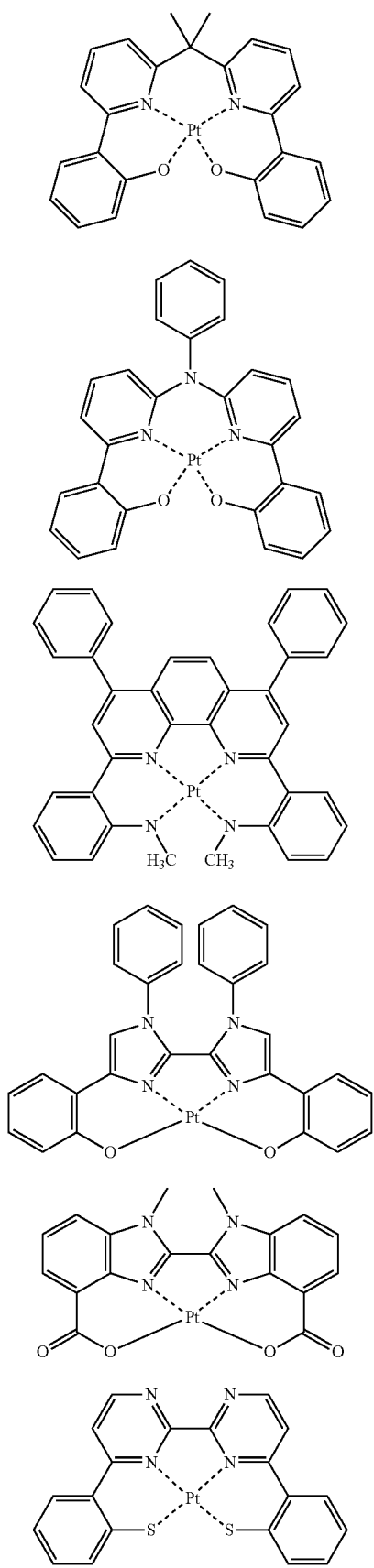
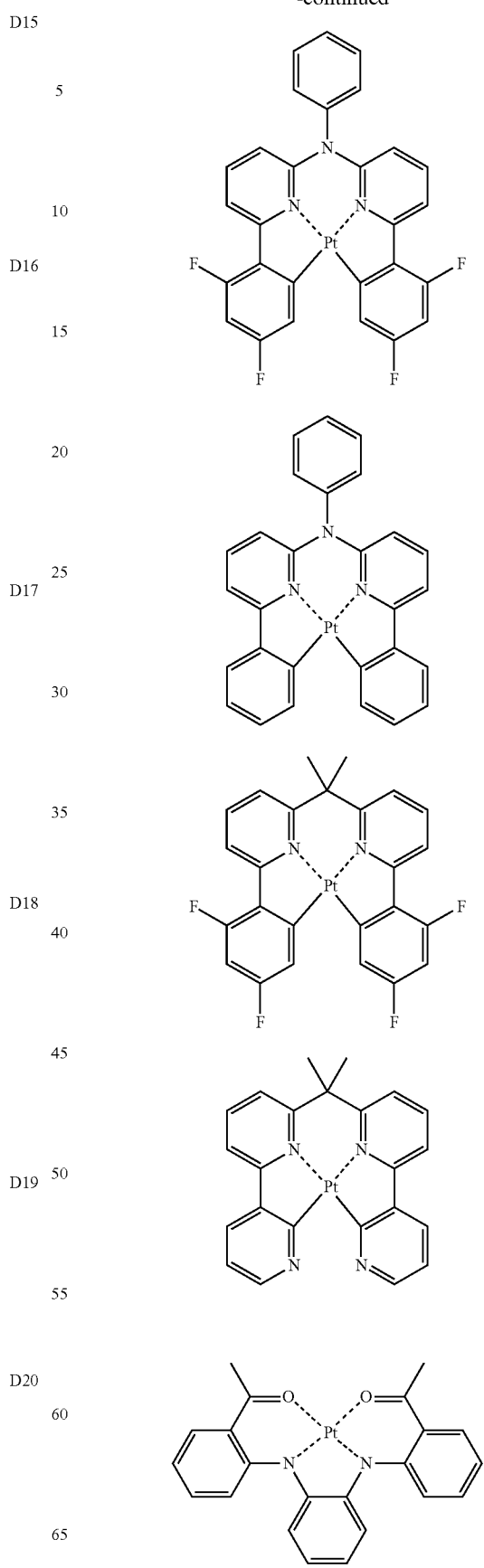

-continued
D26
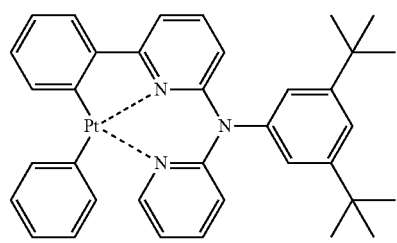
D27
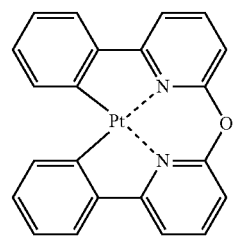
D28
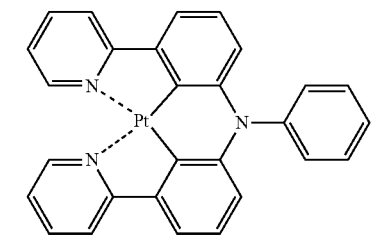
D29
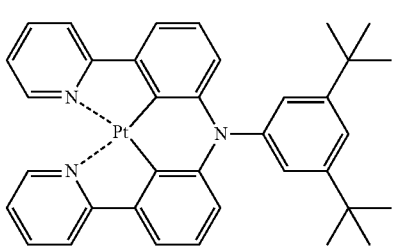
D30
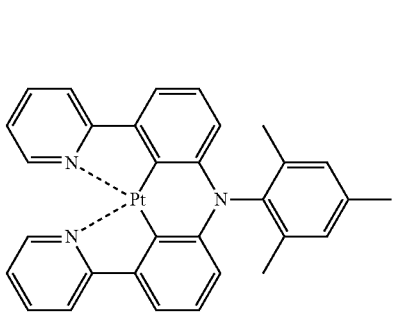
D31
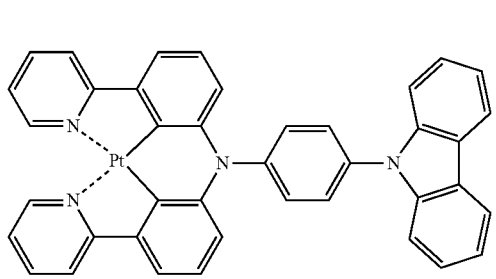
-continued
D32
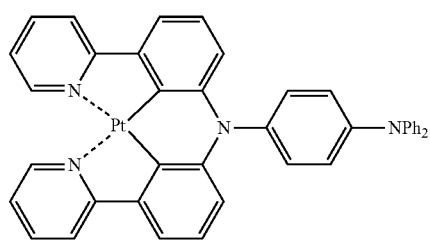
D33
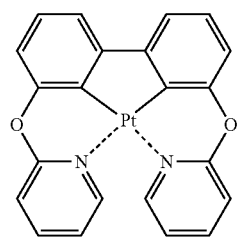
D34
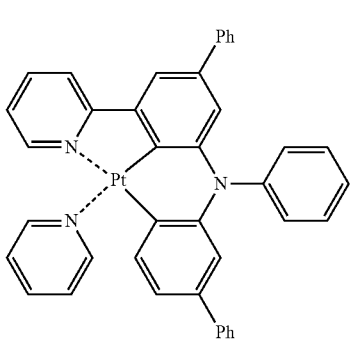
D35
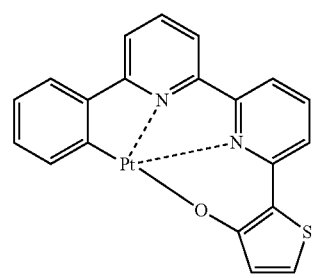
D36
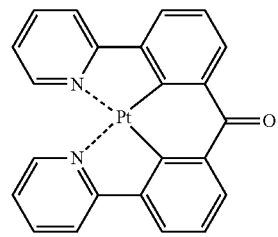

D37 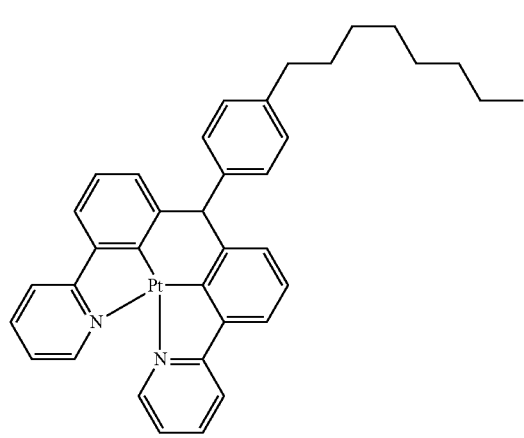
D38 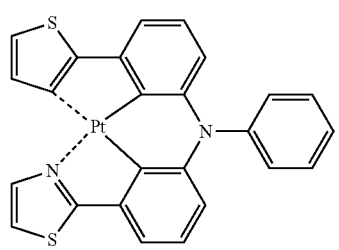
D39 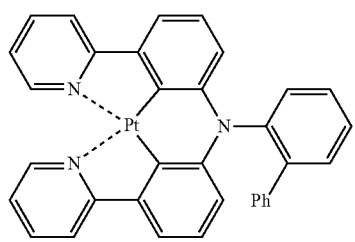
D40 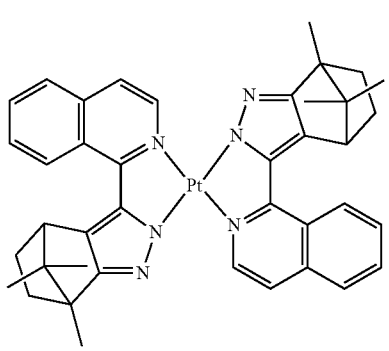
D41 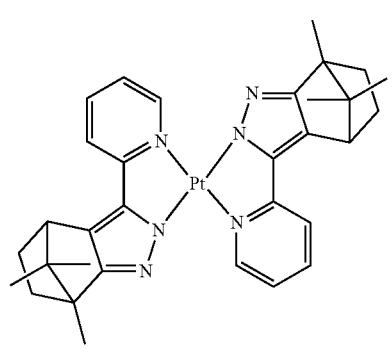
D42 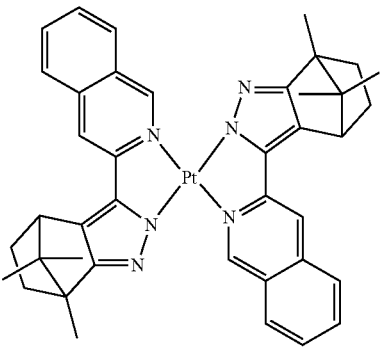
D43 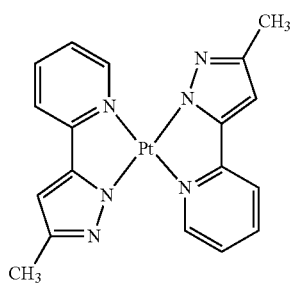
D44 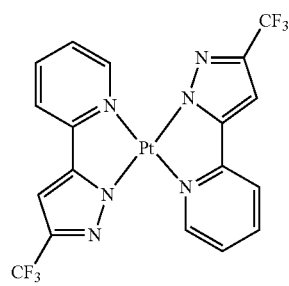
D45 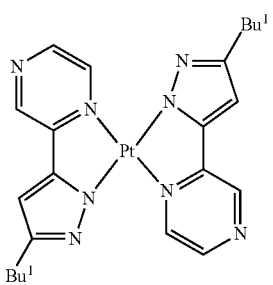
D46 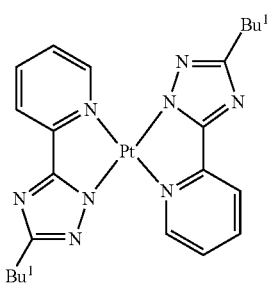

-continued

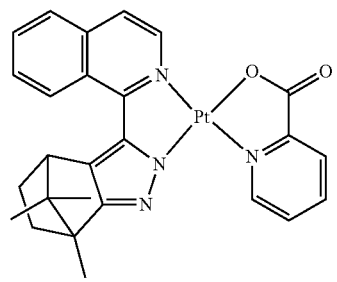
D47

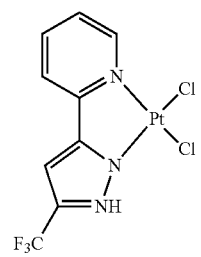
D48

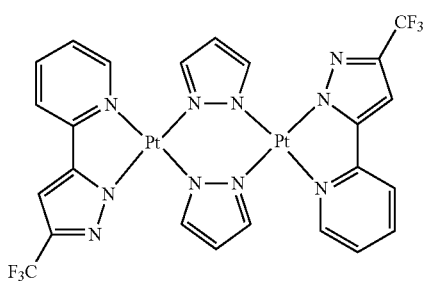
D49

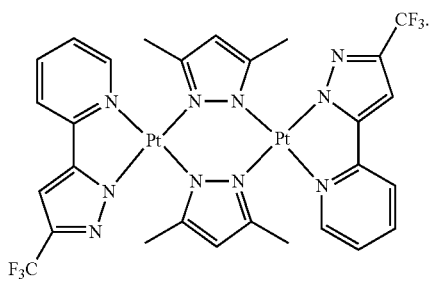
D50

Non-limiting examples of the dopant that may be used in the EML are Pt complexes represented by the following formulae:

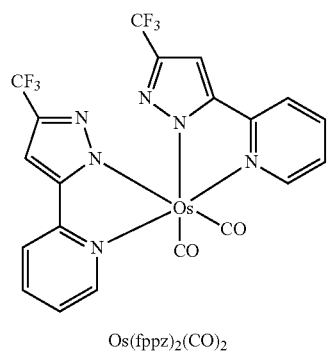

Os(fppz)₂(CO)₂

-continued

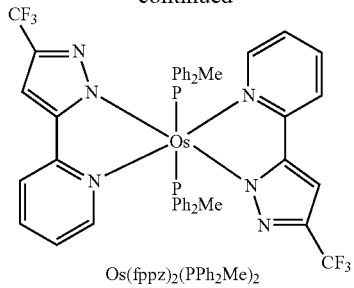

Os(fppz)₂(PPh₂Me)₂

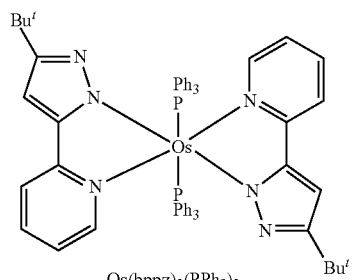

Os(bppz)₂(PPh₃)₂

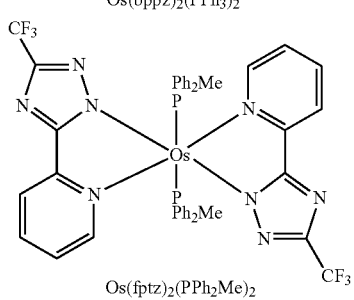

Os(fptz)₂(PPh₂Me)₂

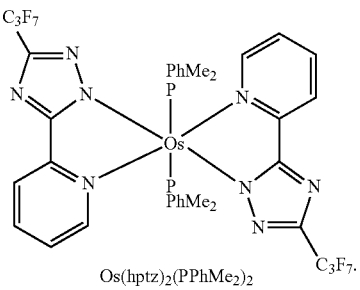

Os(hptz)₂(PPhMe₂)₂

In one embodiment, when the EML includes both a host and a dopant, the amount of the dopant is from about 0.01 parts to about 15 parts by weight based on 100 parts by weight of the host. However, the amount of the dopant is not limited to this range.

In one embodiment, a thickness of the HIL is in a range of about 100 Å to about 10000 Å. In another embodiment, the thickness of the HIL is about 200 Å to about 600 Å. In one embodiment, when the thickness of the EML is within these ranges, the EML has improved light emitting ability without a substantial increase in driving voltage.

Next, an electron transport layer (ETL) is formed on the EML using various methods, for example, by vacuum deposition, spin coating, casting, or the like. When the ETL is formed using vacuum deposition or spin coating, the deposition and coating conditions may be similar to those for the formation of the HIL, though the conditions for deposition and coating may vary according to the material that is used to form the ETL. As a material for the ETL, the pyrene-based compound of Formula 1 may be used.

In an embodiment, a thickness of the ETL is in a range of about 100 Å to about 1000 Å. In another embodiment, the thickness of the ETL is in a range of about 150 Å to about 500 Å. In one embodiment, when the thickness of the ETL is within these ranges, the ETL has satisfactory electron transporting ability without a substantial increase in driving voltage.

The ETL may further include, in addition to the pyrene-based compound, a metal-containing material.

The metal-containing material may include a lithium (Li) complex. Non-limiting examples of the Li complex are lithium quinolate (LIQ) and Compound 203 below:

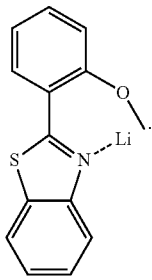

Compound 203

An EIL, which facilitates injection of electrons from the second electrode (for example, a cathode), may be formed on the ETL. Any suitable electron-injecting material may be used to form the EIL.

Non-limiting examples of materials for forming the EIL are LIF, NaCl, CsF, $Li_2O$, and BaO. Deposition conditions of the EIL may be similar to those for the formation of the HIL, although the conditions may vary according to a material that is used to form the EIL.

In an embodiment, a thickness of the EIL is in a range of about 1 Å to about 100 Å. In another embodiment, the thickness of the EIL is in a range about 3 Å to about 90 Å. In one embodiment, when the thickness of the EIL is within these ranges, the EIL may have satisfactory electron transporting ability without a substantial increase in driving voltage.

In an embodiment, the second electrode 17 is disposed on the organic layer 15. The second electrode 17 may be a cathode, which is an electron injecting electrode. A metal for forming the second electrode may be a metal, an alloy, an electrically conductive compound having a low-work function, or a mixture thereof. In this regard, the second electrode 17 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting diode, the transmission electrode may be formed of indium tin oxide (ITO) or indium zinc oxide (IZO).

Herein, an organic light-emitting diode 10 according to an embodiment of the present invention has been described with reference to the drawing, but is not limited to the structure illustrated in the drawing.

When the EML is formed using a phosphorescent dopant, to prevent diffusion of triplet excitons or holes toward the ETL, a hole blocking layer (HBL) may be formed between the HTL and the EML or between the H-functional layer and the EML by a method such as vacuum deposition, spin coating, casting, LB, or the like. When the HBL is formed using vacuum deposition or spin coating, the deposition and coating conditions may be similar to those for the formation of the HIL, though the conditions for deposition and coating may vary according to the material that is used to form the HBL. Any hole-blocking material used in the art may be used. Non-limiting examples of hole-blocking materials include oxadiazole derivatives, triazole derivatives, and phenanthroline derivatives. For example, BCP illustrated below may be used as a material for the HBL.

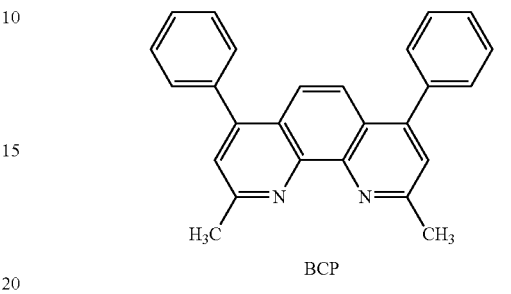

BCP

In an embodiment, a thickness of the HBL is in a range of about 20 Å to about 1000 Å. In another embodiment, the thickness of the HBL is in a range of about 30 Å to about 300 Å. In one embodiment, when the thickness of the HBL is within these ranges, the HBL has improved hole blocking ability without a substantial increase in driving voltage.

The organic light-emitting diode may be included in an organic light-emitting device. According to another aspect, an organic light-emitting device including the organic light-emitting diode and a transistor is provided. The transistor may include an active layer, source and drain electrodes, a gate electrode, and a gate insulating film, and at least one of a first electrode and a second electrode of the organic light-emitting diode may be electrically connected to one of the source and drain electrodes of the transistor. The active layer of the transistor may be selected from various known active layers formed of amorphous silicon, crystalline silicon, an oxide semiconductor, an organic compound semiconductor, for example.

The unsubstituted $C_1$-$C_{60}$ alkyl group (or $C_1$-$C_{60}$ alkyl group) used herein may be a $C_1$-$C_{60}$ linear or branched alkyl group, such as methyl, ethyl, propyl, isobutyl, sec-butyl, pentyl, iso-amyl, or hexyl, and at least one substituent of the substituted $C_1$-$C_{60}$ alkyl group may be selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group and $C_1$-$C_{50}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group;

—N($Q_{11}$)($Q_{12}$); and

—Si($Q_{11}$)($Q_{12}$)($Q_{13}$) wherein $Q_{11}$ and $Q_{12}$ may be each independently a $C_6$-$C_{60}$ aryl group or a $C_2$-$C_{60}$ heteroaryl group, and $Q_{13}$ to $Q_{15}$ may be each independently a $C_1$-$C_{60}$ alkyl group, a $C_1$-$C_{60}$ alkoxy group, a $C_6$-$C_{60}$ aryl group, or a $C_2$-$C_{60}$ heteroaryl group, but is not limited thereto.

In one embodiment, the unsubstituted $C_1$-$C_{60}$ alkoxy group (or $C_1$-$C_{60}$ alkoxy group) used herein has a formula of —OA (where A is the unsubstituted $C_1$-$C_{60}$ alkyl group described above), and examples thereof are methoxy, ethoxy, and isopropyloxy, and at least one hydrogen atom of these alkoxy groups may be substituted with the same substituent as described above in connection with the substituted $C_1$-$C_{60}$ alkyl group.

In one embodiment, the unsubstituted $C_2$-$C_{60}$ alkenyl group (or $C_2$-$C_{60}$ alkenyl group) used herein refers to an unsubstituted $C_2$-$C_{60}$ alkyl group having one or more carbon double bonds at a center or end thereof. Examples of the unsubstituted $C_2$-$C_{60}$ alkenyl group are ethenyl, propenyl, and butenyl. At least one hydrogen atom of these unsubstituted $C_2$-$C_{60}$ alkenyl groups may be substituted with the same substituent as described above in connection with the substituted $C_1$-$C_{60}$ alkyl group.

In one embodiment, the unsubstituted $C_2$-$C_{60}$ alkynyl group (or $C_2$-$C_{60}$ alkynyl group) used herein refers to an unsubstituted $C_2$-$C_{60}$ alkyl group having one or more carbon triple bonds at a center or end thereof. Examples of the unsubstituted $C_2$-$C_{60}$ alkynyl group are ethynyl, propynyl, and the like. At least one hydrogen atom of these alkynyl groups may be substituted with the same substituent as described above in connection with the substituted $C_1$-$C_{60}$ alkyl group.

In an embodiment, the unsubstituted $C_6$-$C_{60}$ aryl group is a monovalent group having a carbocyclic aromatic system having 6 to 60 carbon atoms including at least one aromatic ring. In another embodiment, the unsubstituted $C_6$-$C_{60}$ arylene group is a divalent group having a carbocyclic aromatic system having 6 to 60 carbon atoms including at least one aromatic ring. When the aryl group and the arylene group include two or more rings, the rings may be fused to each other. At least one hydrogen atom of these aryl groups and arylene groups may be substituted with the same substituent as described above in connection with the substituted $C_1$-$C_{60}$ alkyl group.

Examples of the substituted or unsubstituted $C_6$-$C_{60}$ aryl group are a phenyl group, a $C_1$-$C_{10}$ alkylphenyl group (for example, ethylphenyl group), a $C_1$-$C_{10}$ alkylbiphenyl group (for example, ethylbiphenyl group), a halophenyl group (for example, an o-, m- or p-fluorophenyl group, a dichlorophenyl group), a dicyanophenyl group, a trifluoromethoxyphenyl group, o-, m-, and p-tolyl groups, o-, m- and p-cumenyl groups, a mesityl group, a phenoxyphenyl group, a (α,α-dimethylbenzene)phenyl group, a (N,N'-dimethyl)amino-phenyl group, a (N,N'-diphenyl)aminophenyl group, a pentalenyl group, an indenyl group, a naphthyl group, halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), an anthracenyl group, azrenyl group, a heptalenyl group, an acenaphthylenyl group, a phenalenyl group, a fluorenyl group, anthraquinolinyl group, a methylanthryl group, a phenanthryl group, a triphenylenyl group, a pyrenyl group, a chrysenyl group, an ethyl-chrysenyl group, a picenyl group, perylenyl group, a chloroperylenyl group, a pentaphenyl group, a pentasenyl group, a tetraphenylenyl group, a hexaphenyl group, a hexacenyl group, a rubicenyl group, a coroneryl group, a trinaphthylenyl group, a heptaphenyl group, a heptacenyl group, a piranthrenyl group, and an obarenyl group, and examples of the substituted $C_6$-$C_{60}$ aryl group will be understood by referring to the examples of the unsubstituted $C_6$-$C_{60}$ aryl group and the substituents of the substituted $C_1$-$C_{60}$ alkyl group. Examples of the substituted or unsubstituted $C_6$-$C_{60}$ arylene group will be understood by referring to examples of the substituted or unsubstituted $C_6$-$C_{60}$ aryl group.

In an embodiment, the unsubstituted $C_2$-$C_{60}$ heteroaryl group used herein refers to a monovalent group having a system composed of one or more aromatic rings having at least one hetero atom selected from nitrogen (N), oxygen (O), phosphorous (P), and sulfur (S) and carbon atoms as the remaining ring atoms. In another embodiment, the unsubstituted $C_2$-$C_{60}$ heteroarylene group used herein refers to a divalent group having a system composed of one or more aromatic rings having at least one heteroatom selected from nitrogen (N), oxygen (O), phosphorous (P), and sulfur (S), with carbon atoms as the remaining ring atoms. In one embodiment, when the heteroaryl group and the heteroarylene group each include two or more rings, the rings are fused to each other. At least one hydrogen atom of the heteroaryl group and the heteroarylene group may be substituted with the same substituent described in connection with the $C_1$-$C_{60}$ alkyl group.

Examples of the unsubstituted $C_2$-$C_{60}$ heteroaryl group are a pyrazolyl group, an imidazolyl group, a oxazolyl group, a thiazolyl group, a triazolyl group, tetrazolyl, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoan imidazolyl group, an imidazo pyridinyl group, and an imidazo pyrimidinyl group. Examples of the unsubstituted $C_2$-$C_{60}$ heteroarylene group will be understood by referring to the examples of the substituted or unsubstituted $C_2$-$C_{60}$ arylene group.

In one embodiment, the substituted or unsubstituted $C_6$-$C_{60}$ aryloxy group indicates —$OA_2$ (where $A_2$ is the substituted or unsubstituted $C_6$-$C_{60}$ aryl group), and the substituted or unsubstituted $C_5$-$C_{60}$ arylthio group indicates —$SA_3$ (where $A_3$ is the substituted or unsubstituted $C_6$-$C_{60}$ aryl group).

Hereinafter, an organic light-emitting diode according to an embodiment of the present invention is described in detail with reference to Synthesis Examples and Examples. However, the aforementioned Examples are presented for illustrative purposes only, and do not limit the scope of the present invention. The organic light-emitting diode according to an embodiment of the present invention is not limited to the Synthesis Examples and Examples. Regarding Synthesis Examples below, the wording "B was used instead of A" includes the meaning that a molar equivalent amount of B is identical to that of A.

EXAMPLE
Compounds A-5 to A-66
A-5
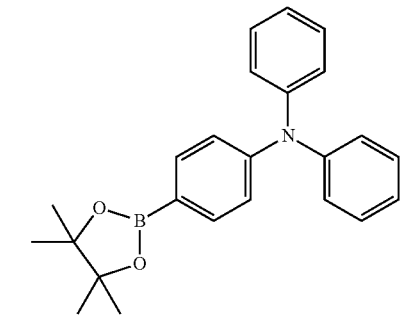
A-14
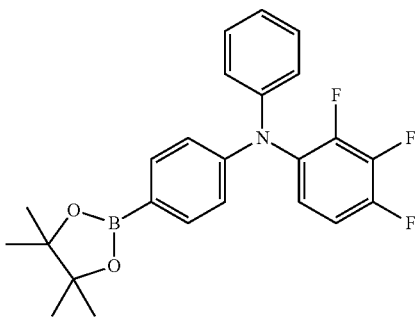
A-15
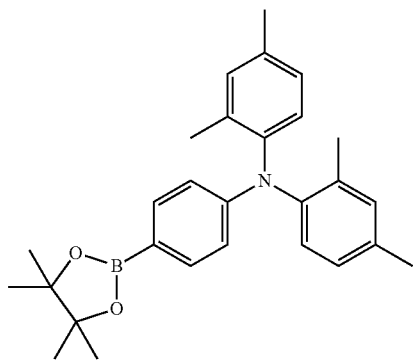
A-17
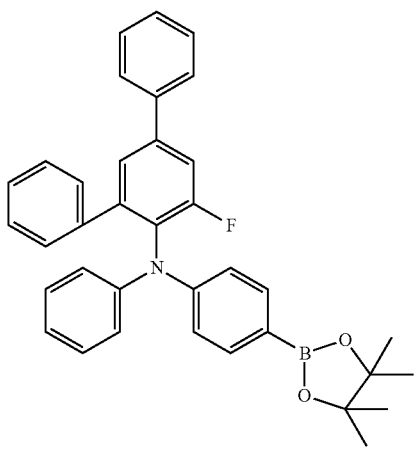
A-19
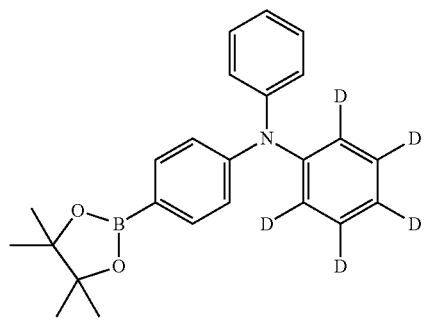
A-20
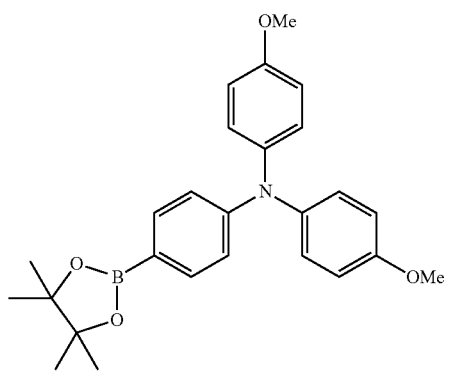
A-21
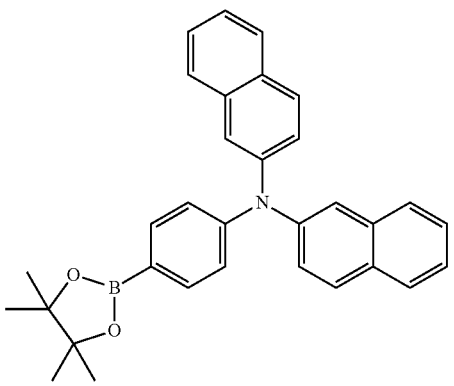
A-22
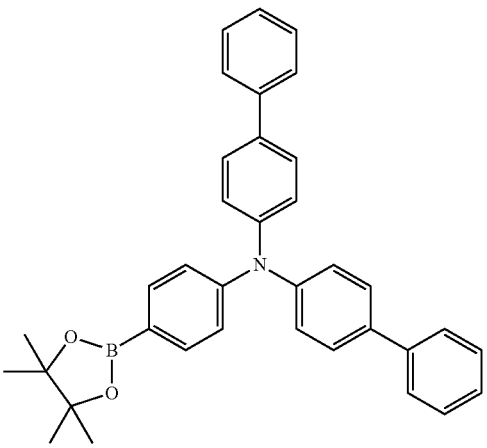

-continued
A-26
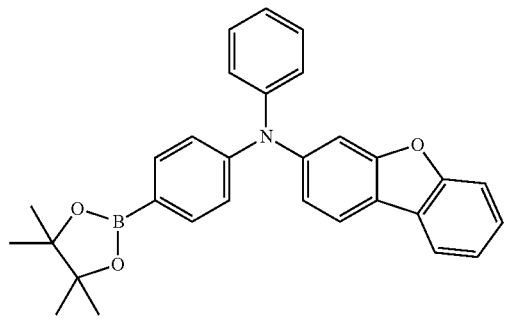
A-27
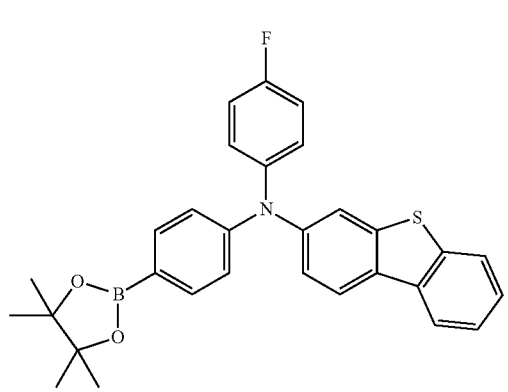
A-29
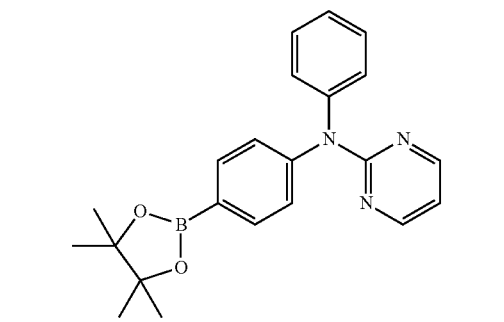
A-31
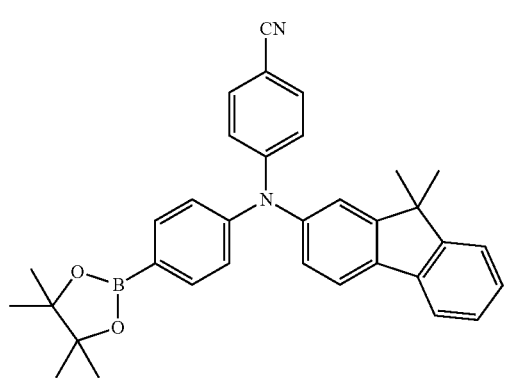
-continued
A-34
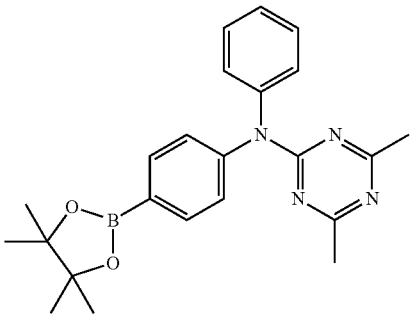
A-35
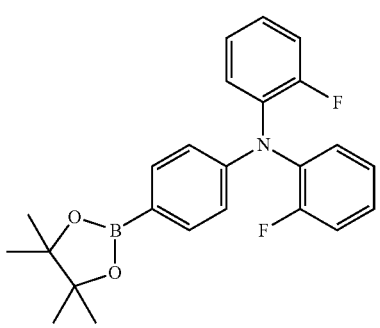
A-36
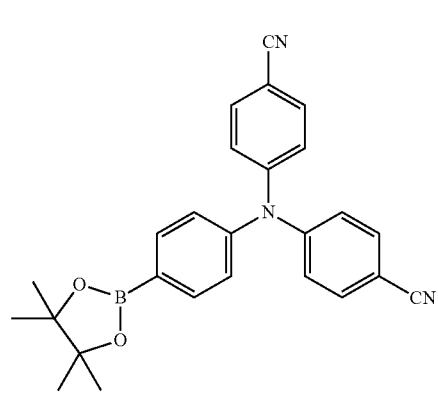
A-38
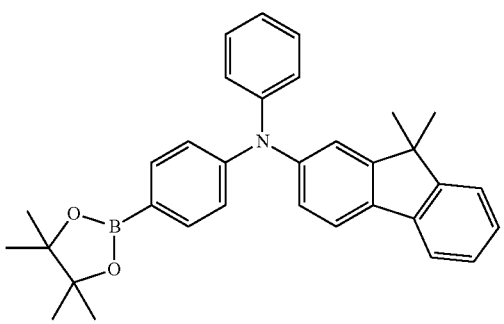

A-43
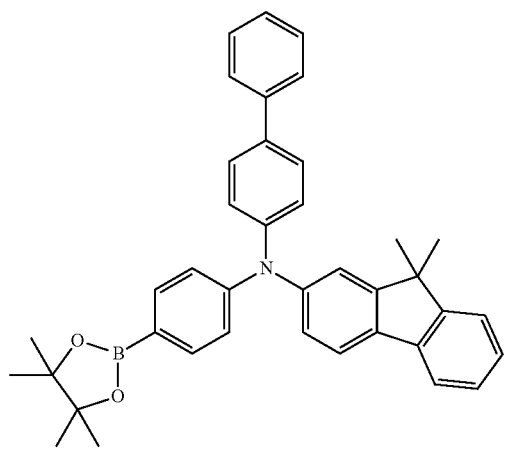
A-48
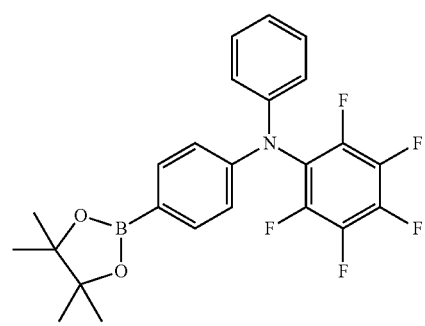
A-51
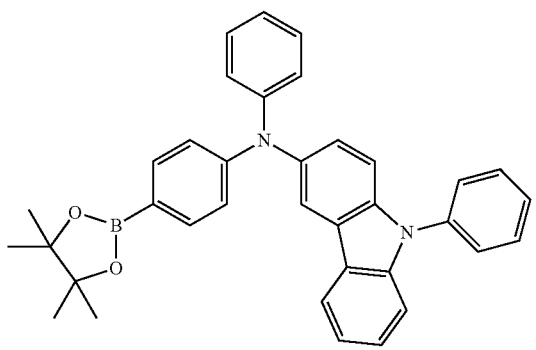
A-53
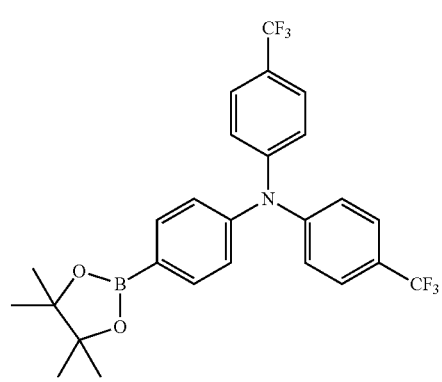
A-57
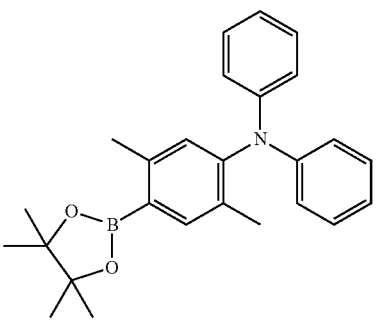
A-58
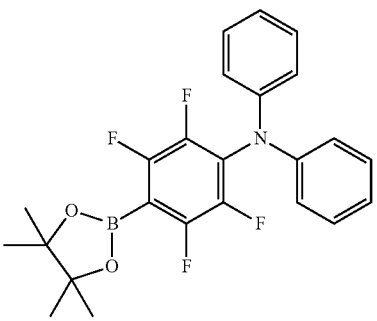
A-59
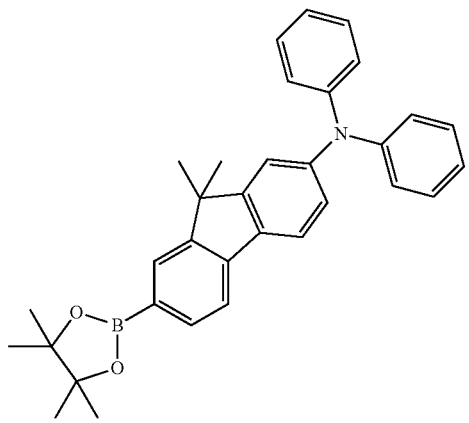
A-61
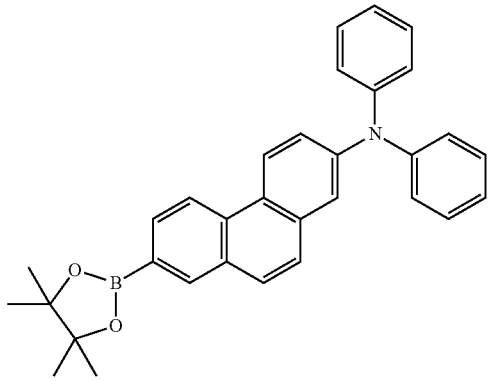

A-64
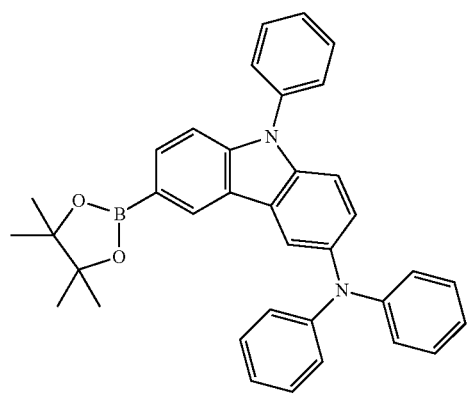
A-65
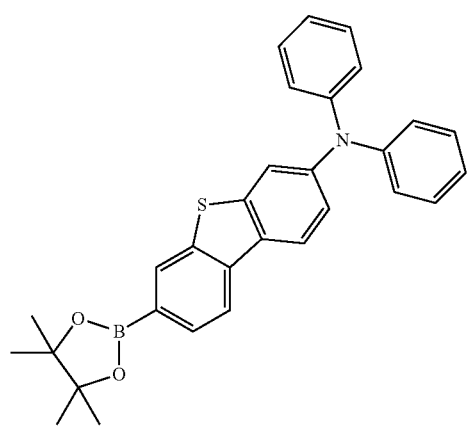
A-66
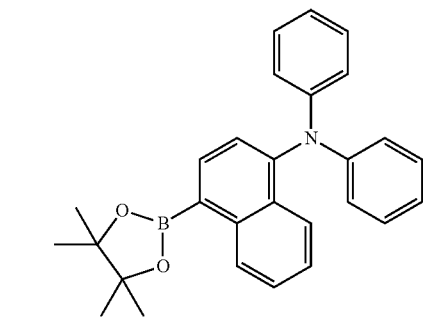
Intermediates 1-5 to 1-66
Intermediate 1-5
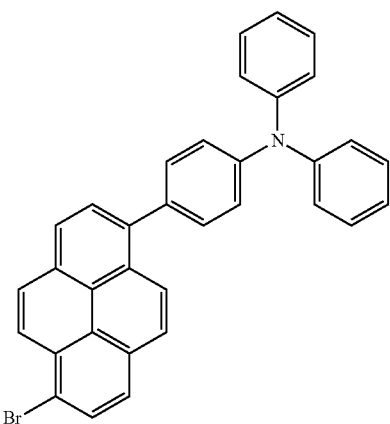
Intermediate 1-14
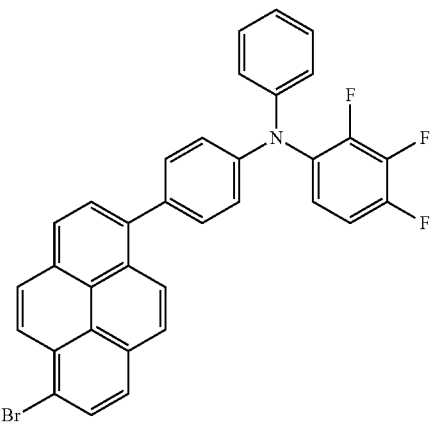
Intermediate 1-15
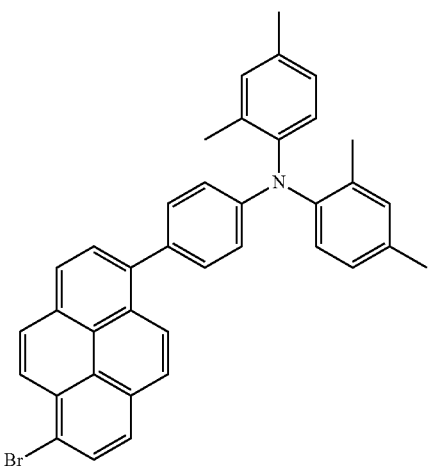
Intermediate 1-17
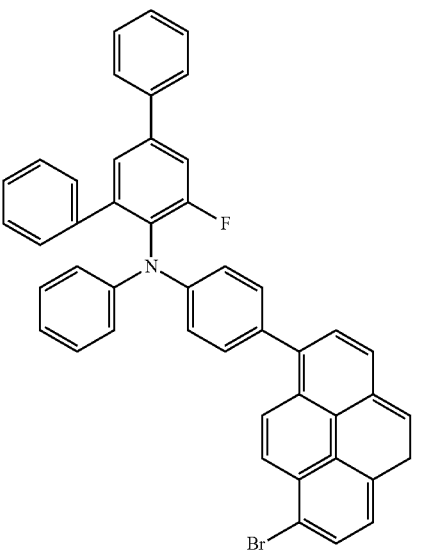

Intermediate 1-19
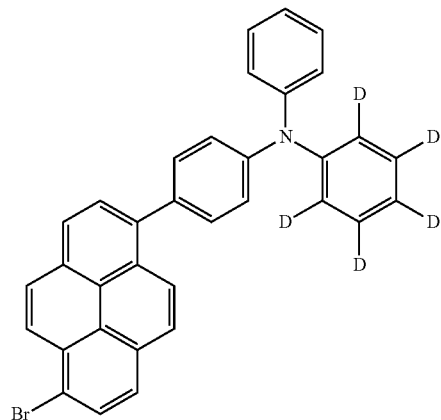
Intermediate 1-20
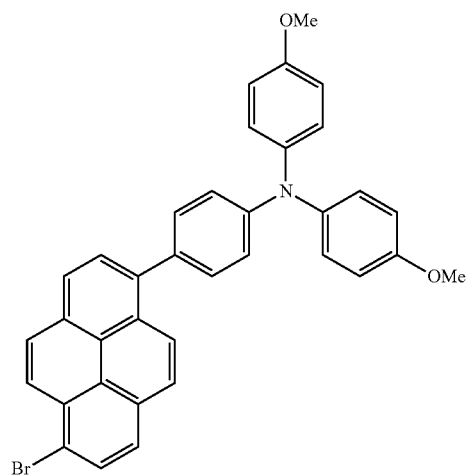
Intermediate 1-21
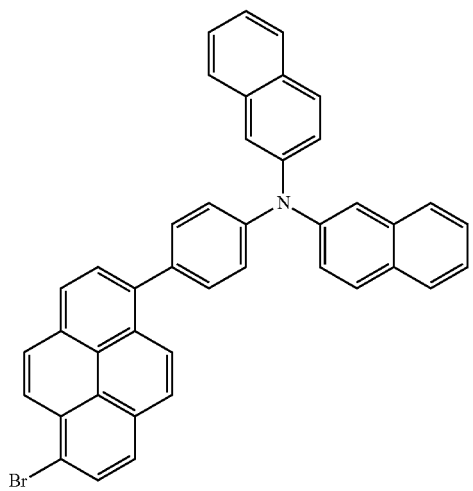
Intermediate 1-22
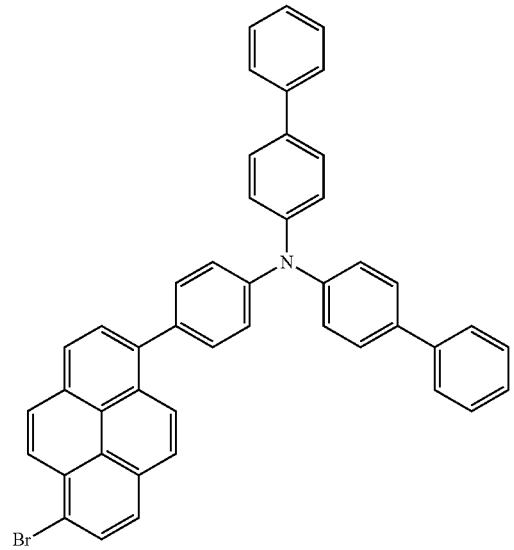
Intermediate 1-26
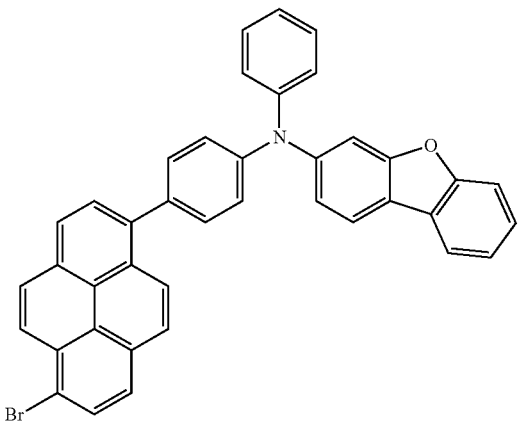
Intermediate 1-27
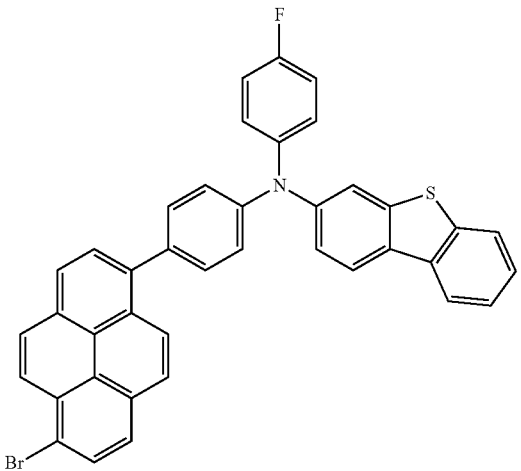

Intermediate 1-29
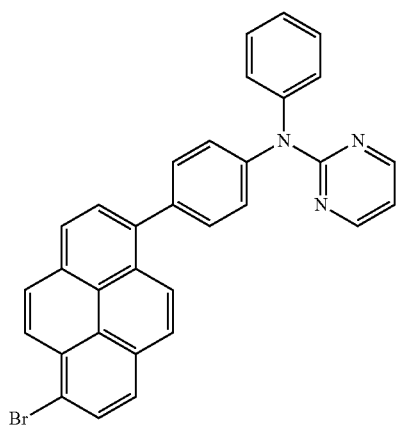
Intermediate 1-35
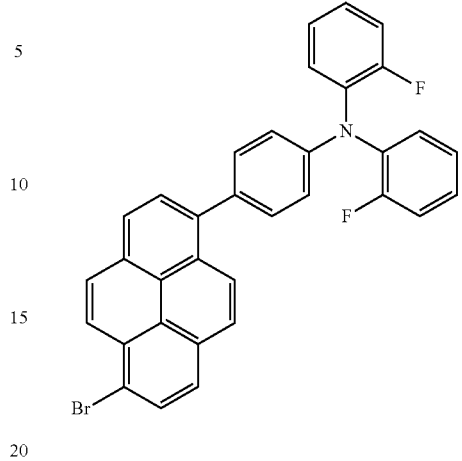
Intermediate 1-31
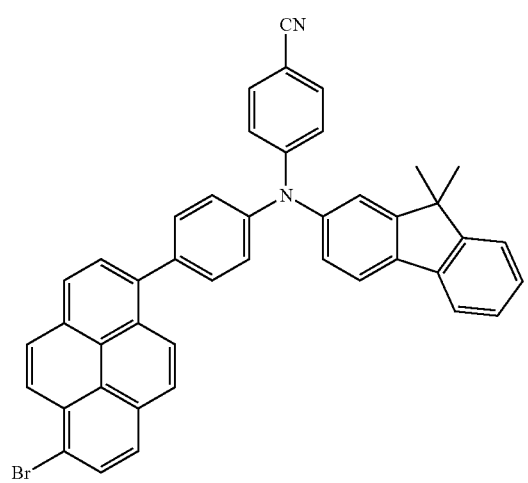
Intermediate 1-36
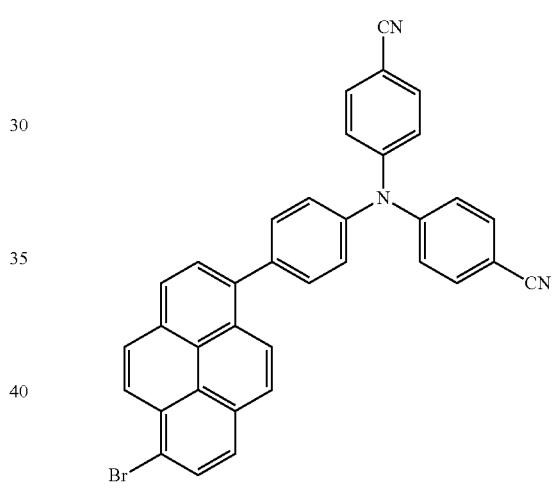
Intermediate 1-34
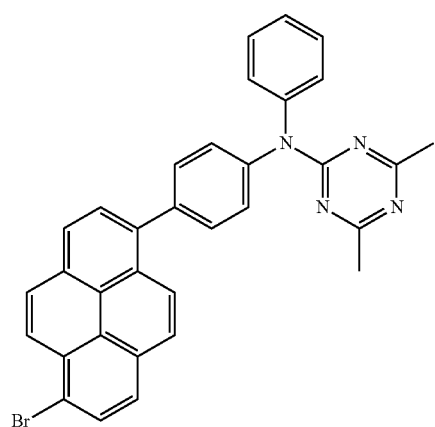
Intermediate 1-38
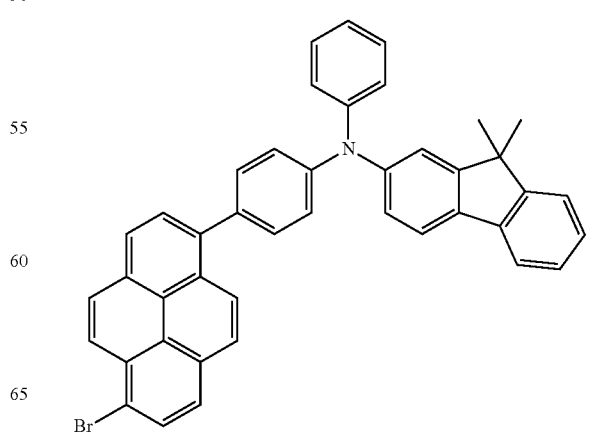

Intermediate 1-43
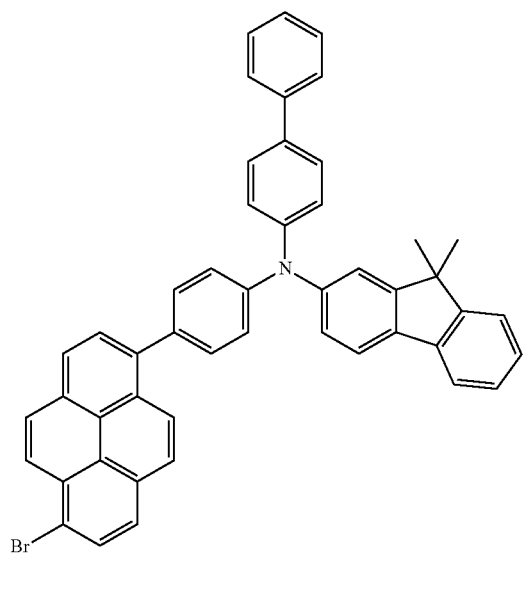
Intermediate 1-53
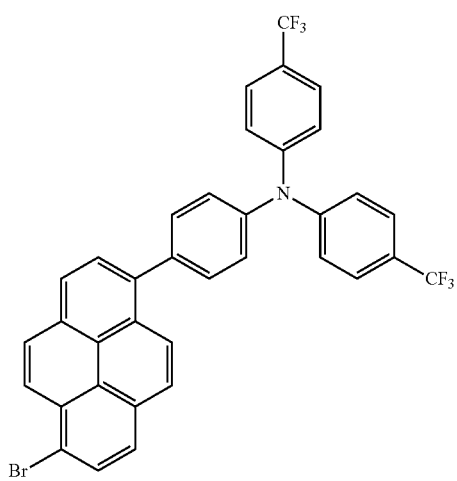
Intermediate 1-48
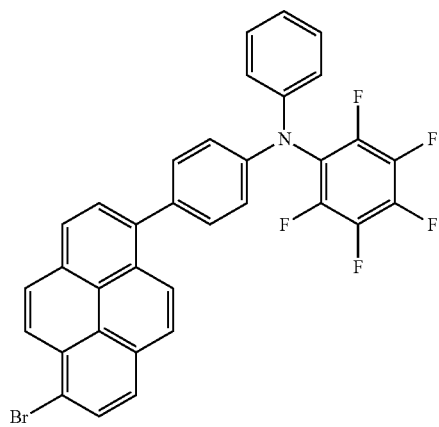
Intermediate 1-57
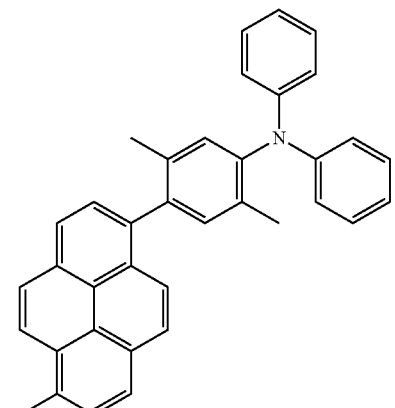
Intermediate 1-51
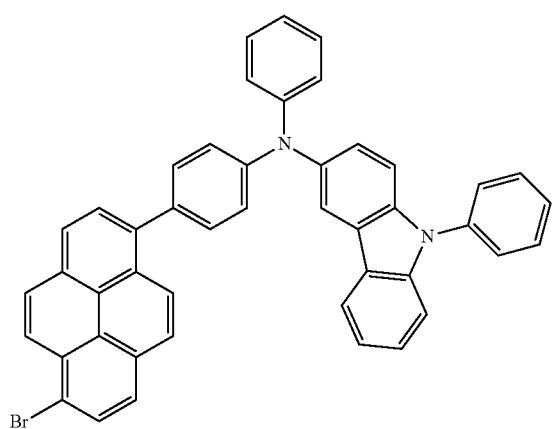
Intermediate 1-58
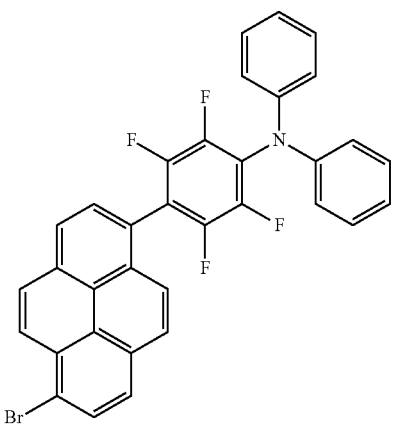

Intermediate 1-59
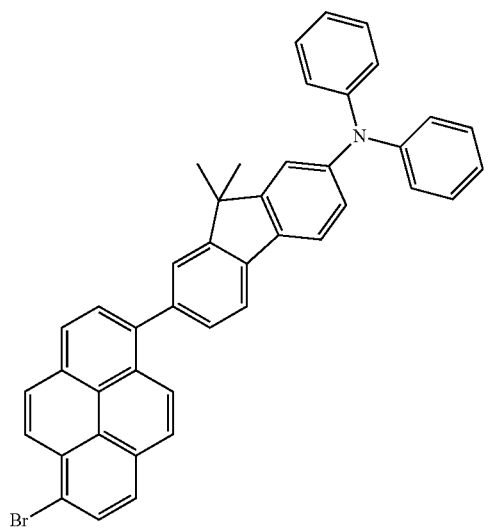
Intermediate 1-61
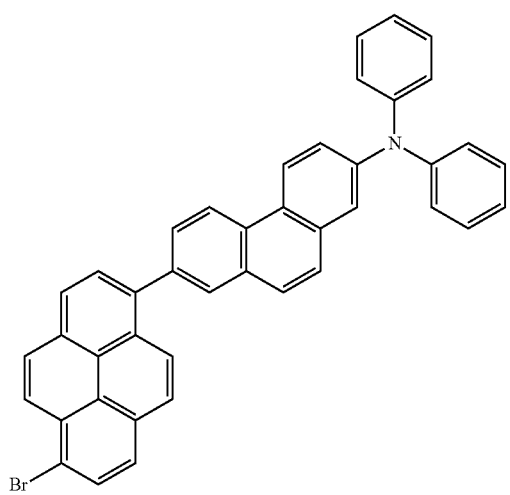
Intermediate 1-64
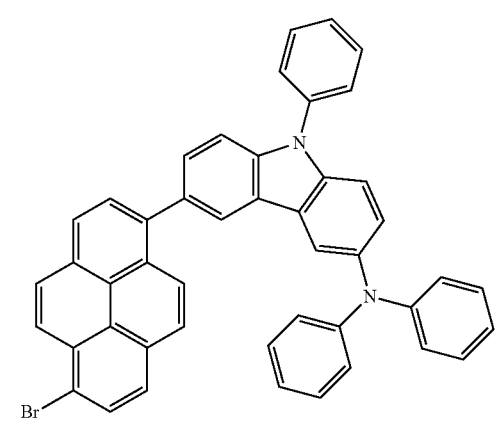
Intermediate 1-65
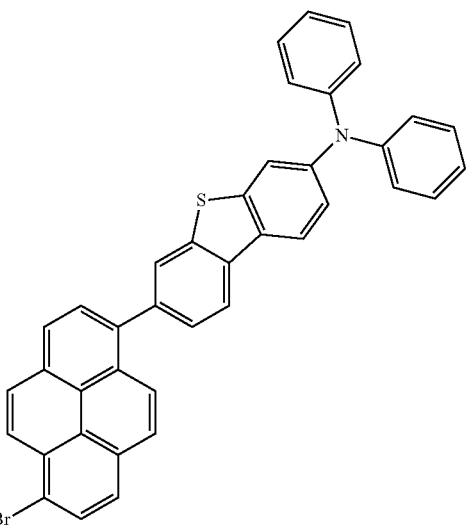
Intermediate 1-66
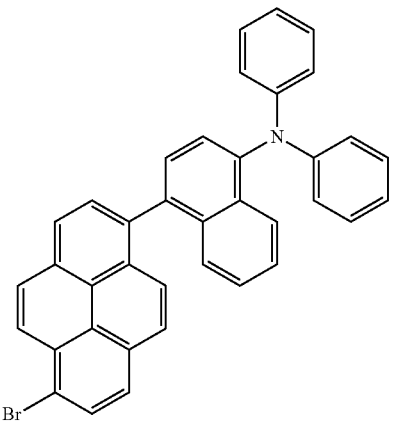
Compounds B-3 to B-71
B-3
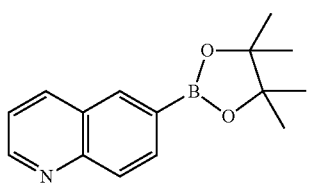
B-5
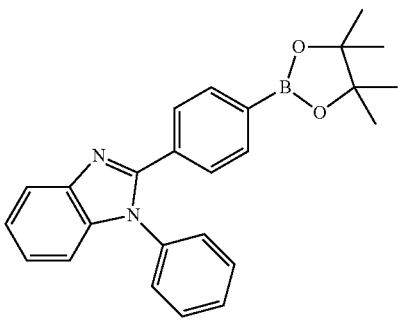

B-7
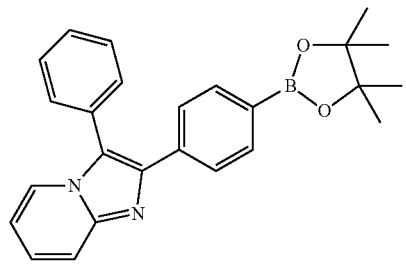
B-10
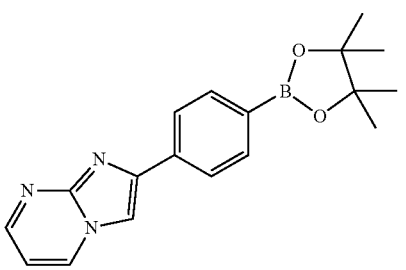
B-11
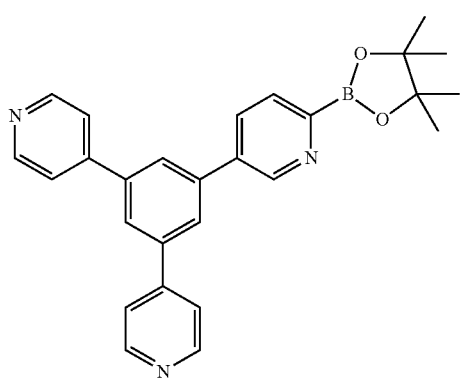
B-17
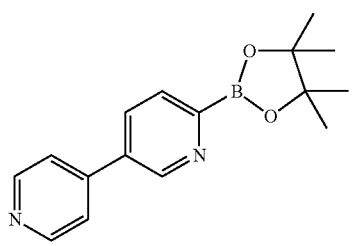
B-30
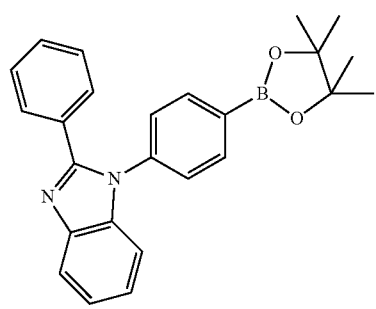
B-43
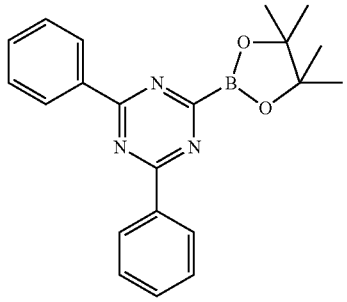
B-51
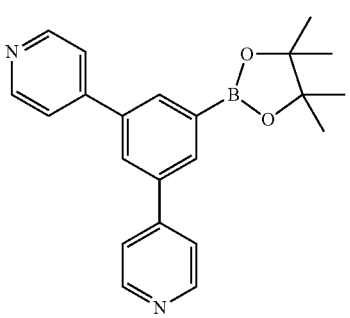
B-68
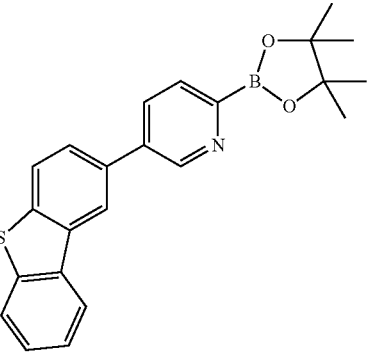
B-69
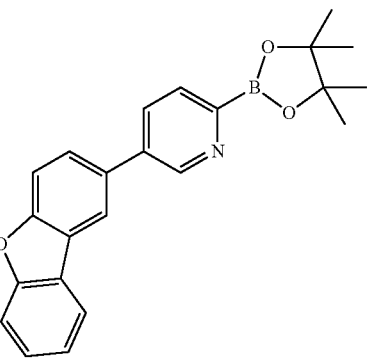

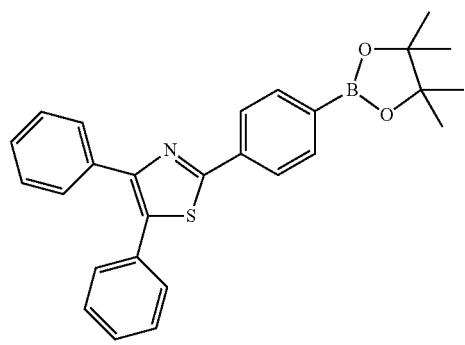
B-70
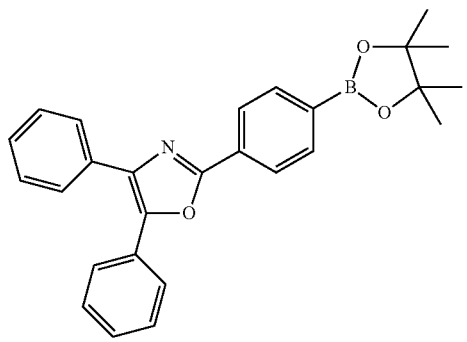
B-71
Synthesis Example 1: Synthesis of Compound 5
Compound 5 was synthesized according to Reaction Scheme 1 below:
Reaction Scheme 1
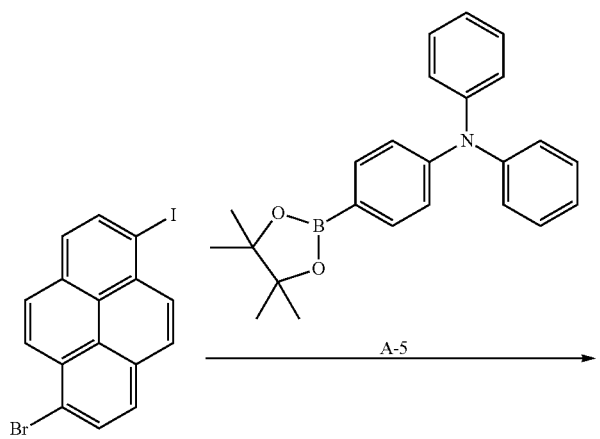
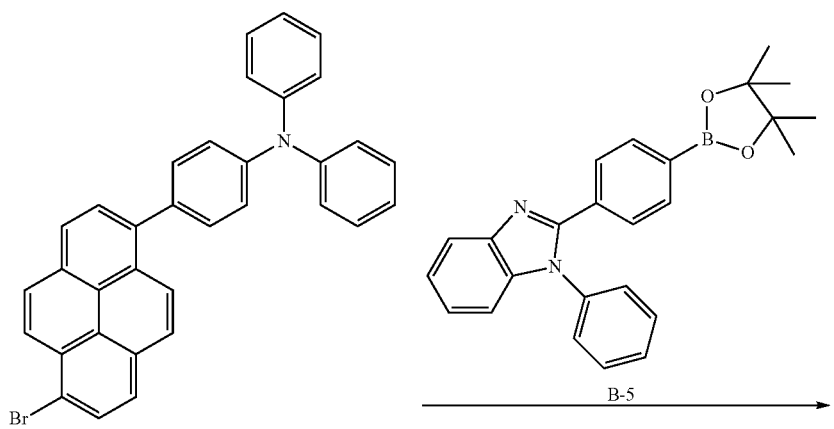
Intermediate 1-5

-continued

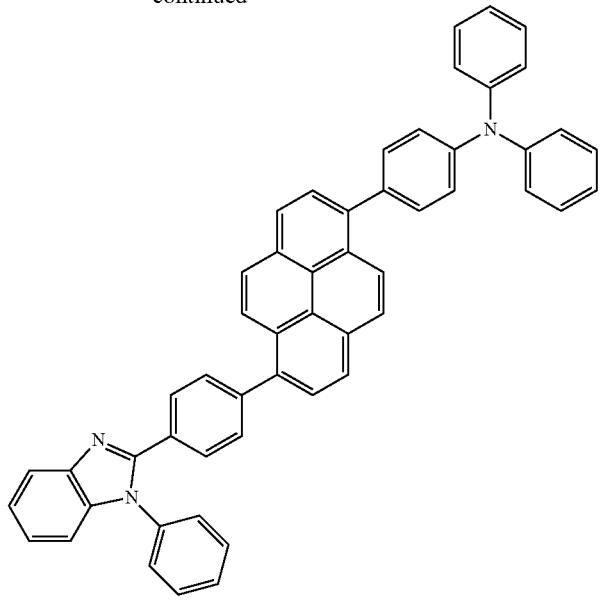

5

Synthesis of Intermediate 1-5

4.01 g (10 mmol) of 4-bromo-9-iodopyrene, 3.71 g (10 mmol) of Compound A-5, 0.29 g (0.25 mmol) of Pd(PPh$_3$)$_4$(tetrakis(triphenylphosphine)palladium), and 0.62 g (4.48 mmol) of K$_2$CO$_3$ were dissolved in 60 ml of THF/H$_2$O (2/1 in a volumetric ratio), and then stirred at a temperature of 70° C. for 5 hours. The reaction solution was cooled to room temperature, and then, was extracted three times with 40 ml of water and 50 ml of ethylether. An organic layer obtained therefrom was dried with magnesium sulfate and a solvent was evaporated and the residual was separation-purified by silica gel column chromatography to obtain 4.45 g (Yield: 85%) of Intermediate 1-5. The obtained compound was identified by MS/FAB.

C$_{34}$H$_{22}$BrN: calc. 524.44, found 524.68.

Synthesis of Compound 5

Compound 5 (550 mg, 90% of yield) was synthesized in the same manner as used to synthesize Intermediate 1-5, except that Intermediate 1-5 and Compound B-5 were used instead of 4-bromo-9-iodopyrene and Compound A-5, respectively. The obtained compound was identified by MS/FAB and 1H NMR.

C$_{53}$H$_{35}$N$_3$: calc. 713.86, found 714.00.

$^1$H NMR (CDCl$_3$, 400 MHz) δ(ppm) 8.20-8.10 (m, 4H), 7.99 (d, 2H), 7.82-7.78 (m, 5H), 7.66-7.55 (m, 5H), 7.52-7.49 (m, 2H), 7.45-7.36 (m, 3H), 7.32-7.28 (m, 1H), 7.24-7.20 (m, 1H), 7.08-7.03 (m, 4H), 6.97-6.93 (m, 2H), 6.66-6.63 (m, 2H), 6.16-6.10 (m, 4H).

Synthesis Example 2: Synthesis of Compound 17

Synthesis of Intermediate 1-17

Intermediate 1-17 was synthesized in the same manner as used to synthesize Intermediate 1-5 of Synthesis Example 1, except that Compound A-17 was used instead of Compound A-5.

Synthesis of Compound 17

Compound 17 (350 mg, 82% of yield) was synthesized in the same manner as used to synthesize Compound 5 of Synthesis Example 1, except that Intermediate 1-17 and Compound B-17 were used instead of Intermediate 1-5 and Compound B-5, respectively. The obtained compound was identified by MS/FAB and $^1$H NMR.

C$_{56}$H$_{36}$FN$_3$: calc. 769.90, found 770.02.

$^1$H NMR (CDCl$_3$, 400 MHz) δ(ppm) 8.90-8.88 (m, 1H), 8.79 (d, 1H), 8.68-8.65 (m, 2H), 8.17-8.11 (m, 2H), 8.06-7.97 (m, 3H), 7.91-7.89 (m, 2H), 7.72-7.61 (m, 7H), 7.56-7.48 (m, 7H), 7.43-7.40 (m, 3H), 7.13-7.06 (m, 3H), 7.00-6.95 (m, 2H), 6.63-6.60 (m, 1H), 6.14-6.11 (m, 2H).

Synthesis Example 3: Synthesis of Compound 21

Synthesis of Intermediate 1-21

Intermediate 1-21 was synthesized in the same manner as used to synthesize Intermediate 1-5 of Synthesis Example 1, except that Compound A-21 was used instead of Compound A-5.

Synthesis of Compound 21

Compound 21 (480 mg, 92% of yield) was prepared in the same manner as used to synthesize Compound 5 of Synthesis Example 1, except that Intermediate 1-21 was used instead of Intermediate 1-5. The obtained compound was identified by MS/FAB and $^1$H NMR.

C$_{61}$H$_{39}$N$_3$: calc. 813.98, found 814.03.

$^1$H NMR (CDCl$_3$, 400 MHz) δ(ppm) 8.20-8.10 (m, 4H), 8.01-7.98 (m, 2H), 7.82-7.70 (m, 8H), 7.67-7.64 (m, 3H), 7.60-7.49 (m, 12H), 7.45-7.36 (m, 4H), 7.32-7.28 (m, 1H), 7.25-7.18 (m, 3H), 6.49-6.45 (m, 2H).

Synthesis Example 4: Synthesis of Compound 30

Compound 30 (680 mg, 92% of yield) was synthesized in the same manner as used to synthesize Compound 17 of Synthesis Example 2, except that Compound B-30 was used instead of Compound B-17. The obtained compound was identified by MS/FAB and $^1$H NMR.

C$_{65}$H$_{42}$FN$_3$: calc. 884.04, found 884.20.

$^1$H NMR (CDCl$_3$, 400 MHz) δ (ppm) 8.18-8.15 (m, 2H), 8.06-8.04 (m, 2H), 8.01-7.98 (m, 2H), 7.82-7.76 (m, 4H), 7.72-7.58 (m, 10H), 7.56-7.49 (m, 7H), 7.41-7.28 (m, 7H), 7.14-7.08 (m, 2H), 6.83-6.80 (m, 2H), 6.71-6.68 (m, 1H), 6.64-6.60 (m, 3H).

Synthesis Example 5: Synthesis of Compound 43

Synthesis of Intermediate 1-43

Intermediate 1-43 was synthesized in the same manner as used to synthesize Intermediate 1-5 of Synthesis Example 1, except that Compound A-43 was used instead of Compound A-5.

Synthesis of Compound 43

Compound 43 (870 mg, 87% of yield) was synthesized in the same manner as used to synthesize Compound 5 of Synthesis Example 1, except that Intermediate 1-43 and Compound B-43 were used instead of Intermediate 1-5 and Compound B-5, respectively. The obtained compound was identified by MS/FAB and $^1$H NMR.

$C_{64}H_{44}N_4$: calc. 869.06, found 869.70.

$^1$H NMR (CDCl$_3$, 400 MHz) δ(ppm) 8.93-8.91 (m, 1H), 8.84-8.80 (m, 4H), 8.34-8.31 (m, 1H), 8.20-8.09 (m, 4H), 8.01-7.98 (m, 1H), 7.78-7.76 (m, 1H), 7.64-7.32 (m, 18H), 7.14-7.08 (m, 2H), 6.71-6.68 (m, 1H), 6.53-6.42 (m, 5H), 1.63 (s, 6H).

Synthesis Example 6: Synthesis of Compound 51

Synthesis of Intermediate 1-51

Intermediate 1-51 was synthesized in the same manner as used to synthesize Intermediate 1-5 of Synthesis Example 1, except that Compound A-51 was used instead of Compound A-5.

Synthesis of Compound 51

Compound 51 (890 mg, 88% of yield) was synthesized in the same manner as used to synthesize Compound 5 of Synthesis Example 1, except that Intermediate 1-51 and Compound B-51 were used instead of Intermediate 1-5 and Compound B-5, respectively. The obtained compound was identified by MS/FAB and $^1$H NMR.

$C_{62}H_{40}N_4$: calc. 841.00, found 841.22.

$^1$H NMR (CDCl$_3$, 400 MHz) δ(ppm) 8.80-8.76 (m, 4H), 8.22-8.15 (m, 2H), 8.04-7.96 (m, 6H), 7.90-7.88 (m, 2H), 7.82-7.80 (m, 1H), 7.61-7.55 (m, 5H), 7.52-7.47 (m, 6H), 7.42-7.23 (m, 6H), 7.09-7.04 (m, 2H), 6.96-6.93 (m, 2H), 6.87-6.84 (m, 1H), 6.66-6.63 (m, 1H), 6.31-6.29 (m, 2H).

Synthesis Example 7: Synthesis of Compound 59

Synthesis of Intermediate 1-59

Intermediate 1-59 was synthesized in the same manner as used to synthesize Intermediate 1-5 of Synthesis Example 1, except that Compound A-59 was used instead of Compound A-5.

Synthesis of Compound 59

Compound 59 (440 mg, 81% of yield) was synthesized in the same manner as used to synthesize Compound 5 of Synthesis Example 1, except that Intermediate 1-59 was used instead of Intermediate 1-5. The obtained compound was identified by MS/FAB and $^1$H NMR.

$C_{62}H_{43}N_3$: calc. 830.02, found 830.21.

$^1$H NMR (CDCl$_3$ 400 MHz) δ(ppm) 8.20-8.18 (m, 2H), 8.12-8.10 (m, 1H), 8.01-7.96 (m, 2H), 7.92-7.90 (m, 1H), 7.82-7.76 (m, 7H), 7.68-7.53 (m, 6H), 7.44-7.35 (m, 4H), 7.32-7.21 (m, 2H), 7.09-7.04 (m, 4H), 6.67-6.63 (m, 3H), 6.39-6.38 (m, 1H), 6.16-6.13 (m, 4H), 1.63 (s, 6H).

Synthesis Example 8: Synthesis of Compound 3

Compound 3 (750 mg, 80% of yield) was synthesized in the same manner as used to synthesize Compound 5 of Synthesis Example 1, except that Compound B-3 was used instead of Compound B-5. The obtained compound was identified by MS/FAB and $^1$H NMR.

$C_{43}H_{28}N_2$: calc. 572.69, found 572.75.

$^1$H NMR (CDCl$_3$, 400 MHz) δ(ppm) 8.75-8.72 (m, 2H), 8.21-8.14 (m, 4H), 8.07-8.05 (m, 1H), 8.01-7.97 (m, 2H), 7.86-7.74 (m, 4H), 7.60 (d, 1H), 7.51-7.48 (m, 2H), 7.35 (dd, 1H), 7.08-7.04 (m, 4H), 6.97-6.93 (m, 2H), 6.66-6.62 (m, 2H), 6.17-6.13 (m, 4H).

Synthesis Example 9: Synthesis of Compound 7

Compound 7 (850 mg, 83% of yield) was synthesized in the same manner as used to synthesize Compound 5 of Synthesis Example 1, except that Compound B-7 was used instead of Compound B-5. The obtained compound was identified by MS/FAB and $^1$H NMR.

$C_{52}H_{35}N_3$: calc. 713.86, found 713.90.

$^1$H NMR (CDCl$_3$, 400 MHz) δ(ppm) 8.62-8.60 (m, 1H), 8.17-8.07 (m, 4H), 8.01-7.98 (m, 2H), 7.91-7.88 (m, 2H), 7.82-7.79 (m, 2H), 7.76-7.63 (m, 2H), 7.66-7.59 (m, 3H), 7.52-7.45 (m, 5H), 7.28-7.24 (m, 1H), 7.08-6.97 (m, 4H), 6.97-6.87 (m, 3H), 6.66-6.63 (m, 2H), 6.16-6.10 (m, 4H).

Synthesis Example 10: Synthesis of Compound 10

Compound 10 (650 mg, 87% of yield) was synthesized in the same manner as used to synthesize Compound 5 of Synthesis Example 1, except that Compound B-10 was used instead of Compound B-5. The obtained compound was identified by MS/FAB and $^1$H NMR.

$C_{46}H_{30}N_4$: calc. 638.75, found 638.94.

$^1$H NMR (CDCl$_3$, 400 MHz) δ(ppm) 8.49 (dd, 1H), 8.43-8.41 (m, 1H), 8.21-8.10 (m, 4H), 8.01-7.94 (m, 4H), 7.89-7.87 (d, 1H), 7.81 (d, 2H), 7.60 (d, 2H), 7.52-7.48 (m, 2H), 7.08-7.03 (m, 4H), 6.97-6.93 (m, 2H), 6.80 (dd, 1H), 6.66-6.63 (m, 2H), 6.16-6.12 (m, 4H).

Synthesis Example 11: Synthesis of Compound 11

Compound 11 (720 mg, 90% of yield) was synthesized in the same manner as used to synthesize Compound 5 of Synthesis Example 1, except that Compound B-11 was used instead of Compound B-5. The obtained compound was identified by MS/FAB and $^1$H NMR.

$C_{55}H_{36}N_4$: calc. 752.90, found 752.95.

$^1$H NMR (CDCl$_3$, 400 MHz) δ(ppm) 9.02-8.99 (m, 1H), 8.94-8.91 (m, 1H), 8.80-8.77 (m, 3H), 8.68-8.66 (m, 1H), 8.16 (d, 1H), 8.07-7.85 (m, 10H), 7.67-7.61 (m, 2H), 7.54-7.45 (m, 5H), 7.08-7.04 (m, 4H), 6.96-6.93 (m, 2H), 6.66-6.63 (m, 2H), 6.46-6.43 (m, 4H).

Synthesis Example 12: Synthesis of Compound 14

Synthesis of Intermediate 1-14

Intermediate 1-14 was synthesized in the same manner as used to synthesize Intermediate 1-5 of Synthesis Example 1, except that Compound A-14 was used instead of Compound A-5.

Synthesis of Compound 14

Compound 14 (760 mg, 83% of yield) was synthesized in the same manner as used to synthesize Compound 5 of Synthesis Example 1, except that Intermediate 1-14 and Compound B-17 were used instead of Intermediate 1-5 and Compound B-5, respectively. The obtained compound was identified by MS/FAB and $^1$H NMR:

$C_{44}H_{26}N_3F_3$: calc. 653.69, found 653.77.

$^1$H NMR (CDCl$_3$, 400 MHz) δ(ppm) 8.90-8.88 (m, 1H), 8.79 (d, 1H), 8.68-8.65 (m, 2H), 8.17-8.11 (m, 2H), 8.05-7.98 (m, 3H), 7.92-7.88 (m, 2H), 7.67-7.61 (m, 2H), 7.53-7.49 (m, 2H), 7.43-7.40 (m, 2H), 7.10-7.06 (m, 2H), 6.81-6.73 (m, 2H), 6.65-6.56 (m, 3H), 6.37-6.34 (m, 2H).

Synthesis Example 13: Synthesis of Compound 15

Synthesis of Intermediate 1-15
Intermediate 1-15 was synthesized in the same manner as used to synthesize Intermediate 1-5 of Synthesis Example 1, except that Compound A-15 was used instead of Compound A-5.
Synthesis of Compound 15
Compound 15 (490 mg, 88% of yield) was synthesized in the same manner as used to synthesize Compound 5 of Synthesis Example 1, except that Intermediate 1-15 and Compound B-17 were used instead of Intermediate 1-5 and Compound B-5, respectively. The obtained compound was identified by MS/FAB and $^1$H NMR.
C$_{48}$H$_{37}$N$_3$: calc. 655.82, found 655.91.
$^1$H NMR (CDCl$_3$, 400 MHz) δ(ppm) 8.90-8.80 (m, 1H), 8.75 (d, 1H), 8.68-8.64 (m, 2H), 8.17-8.11 (m, 2H), 8.06-7.98 (m, 3H), 7.91-7.88 (m, 2H), 7.67-7.59 (m, 2H), 7.49-7.43 (m, 4H), 6.98-6.90 (m, 4H), 6.77-6.72 (m, 4H), 2.26 (s, 6H), 1.94 (s, 6H).

Synthesis Example 14: Synthesis of Compound 19

Synthesis of Intermediate 1-19
Intermediate 1-19 was synthesized in the same manner as used to synthesize Intermediate 1-5 of Synthesis Example 1, except that Compound A-19 was used instead of Compound A-5.
Synthesis of Compound 19
Compound 19 (720 mg, 85% of yield) was synthesized in the same manner as used to synthesize Compound 5 of Synthesis Example 1, except that Intermediate 1-19 was used instead of Intermediate 1-5. The obtained compound was identified by MS/FAB and $^1$H NMR.
C$_{53}$H$_{30}$N$_3$D$_5$: calc. 718.89, found 718.92.
$^1$H NMR (CDCl$_3$, 400 MHz) δ(ppm) 8.20-8.10 (m, 4H), 8.01-7.98 (m, 2H), 7.82-7.78 (m, 5H), 7.62-7.55 (m, 5H), 7.52-7.48 (m, 2H), 7.44-7.35 (m, 3H), 7.31-7.28 (m, 1H), 7.24-7.21 (m, 1H), 7.08-7.04 (m, 2H), 6.97-6.93 (m, 2H), 6.66-6.63 (m, 1H), 6.16-6.12 (m, 2H).

Synthesis Example 15: Synthesis of Compound 20

Synthesis of Intermediate 1-20
Intermediate 1-20 was synthesized in the same manner as used to synthesize Intermediate 1-5 of Synthesis Example 1, except that Compound A-20 was used instead of Compound A-5.
Synthesis of Compound 20
Compound 20 (720 mg, 84% of yield) was synthesized in the same manner as used to synthesize Compound 5 of Synthesis Example 1, except that Intermediate 1-20 was used instead of Intermediate 1-5. The obtained compound was identified by MS/FAB and $^1$H NMR.
C$_{55}$H$_{39}$N$_3$O$_2$: calc. 773.91, found 773.98.
$^1$H NMR (CDCl$_3$, 400 MHz) δ(ppm) 8.20-8.17 (m, 2H), 8.16-8.10 (m, 2H), 8.01-7.98 (m, 2H), 7.82-7.70 (m, 5H), 7.67-7.64 (m, 1H), 7.61-7.55 (m, 4H), 7.52-7.48 (m, 2H), 7.44-7.35 (m, 3H), 7.32-7.28 (m, 2H), 7.25-7.21 (m, 2H), 7.14-7.08 (m, 4H), 6.97-6.88 (m, 4H), 3.83 (s, 6H).

Synthesis Example 16: Synthesis of Compound 22

Synthesis of Intermediate 1-22
Intermediate 1-22 was synthesized in the same manner as used to synthesize Intermediate 1-5 of Synthesis Example 1, except that Compound A-22 was used instead of Compound A-5.
Synthesis of Compound 22
Compound 22 (680 mg, 91% of yield) was synthesized in the same manner as used to synthesize Compound 5 of Synthesis Example 1, except that Intermediate 1-22 was used instead of Intermediate 1-5. The obtained compound was identified by MS/FAB and $^1$H NMR.
C$_{65}$H$_{43}$N$_3$: calc. 866.05, found 866.12.
$^1$H NMR (CDCl$_3$, 400 MHz) δ(ppm) 820-8.10 (m, 4H), 8.01-7.98 (m, 2H), 7.82-7.78 (m, 5H), 7.67-7.60 (m, 6H), 7.59-7.55 (m, 3H), 7.52-7.49 (m, 6H), 7.45-7.35 (m, 9H), 7.30-7.28 (m, 1H), 7.25-7.21 (m, 4H), 6.86-6.82 (m, 3H).

Synthesis Example 17: Synthesis of Compound 26

Synthesis of Intermediate 1-26
Intermediate 1-26 was synthesized in the same manner as used to synthesize intermediate 1-5 of Synthesis Example 1, except that Compound A-26 was used instead of Compound A-5.
Synthesis of Compound 26
Compound 26 (650 mg, 87% of yield) was synthesized in the same manner as used to synthesize Compound 5 of Synthesis Example 1, except that Intermediate 1-26 was used instead of Intermediate 1-5. The obtained compound was identified by MS/FAB and $^1$H NMR.
C$_{59}$H$_{37}$N$_3$O: calc. 803.94, found 804.00.
$^1$H NMR (CDCl$_3$, 400 MHz) δ(ppm) 8.20-8.10 (m, 4H), 8.01-7.98 (m, 2H), 7.82-7.72 (m, 7H), 7.67-7.64 (m, 2H), 7.60-7.50 (m, 7H), 7.45-7.37 (m, 4H), 7.28-7.20 (m, 2H), 7.09-7.04 (m, 2H), 6.96-6.91 (m, 2H), 6.66-6.58 (m, 3H), 6.37-6.33 (m, 2H).

Synthesis Example 18: Synthesis of Compound 27

Synthesis of Intermediate 1-27
Intermediate 1-27 was synthesized in the same manner as used to synthesize Intermediate 1-5 of Synthesis Example 1, except that Compound A-27 was used instead of Compound A-5.
Synthesis of Compound 27
Compound 27 (620 mg, 83% of yield) was synthesized in the same manner as used to synthesize Compound 5 of Synthesis Example 1, except that Intermediate 1-27 was used instead of Intermediate 1-5. The obtained compound was identified by MS/FAB and $^1$H NMR.
C$_{59}$H$_{36}$N$_3$SF: calc. 838.00, found 838.04.
$^1$H NMR (CDCl$_3$, 400 MHz) δ(ppm) 8.20-8.10 (m, 6H), 8.01-7.98 (m, 2H), 7.82-7.75 (m, 6H), 7.67-7.64 (m, 1H), 7.61-7.56 (m, 4H), 7.52-7.50 (m, 2H), 7.45-7.34 (m, 5H), 7.30-7.28 (m, 1H), 7.25-7.22 (m, 1H), 7.12-7.10 (m, 1H), 7.01-6.89 (m, 3H), 6.73-6.68 (m, 2H), 6.66-6.63 (m, 2H).

Synthesis Example 19: Synthesis of Compound 29

Synthesis of Intermediate 1-29
Intermediate 1-29 was synthesized in the same manner as used to synthesize Intermediate 1-5 of Synthesis Example 1, except that Compound A-29 was used instead of Compound A-5.
Synthesis of Compound 29
Compound 29 (740 mg, 86% of yield) was synthesized in the same manner as used to synthesize Compound 5 of Synthesis Example 1, except that Intermediate 1-29 was used instead of Intermediate 1-5. The obtained compound was identified by MS/FAB and $^1$H NMR.

$C_{51}H_{33}N_5$: calc. 715.84, found 715.92.

$^1$H NMR (CDCl$_3$, 400 MHz) δ(ppm) 8.61-8.59 (m, 2H), 8.20-8.10 (m, 4H), 8.01-7.98 (m, 2H), 7.85-7.78 (m, 3H), 7.73-7.59 (m, 3H), 7.55-7.49 (m, 7H), 7.44-7.30 (m, 5H), 7.24-7.21 (m, 3H), 7.13-7.03 (m, 2H), 6.99-6.97 (m, 2H).

Synthesis Example 20: Synthesis of Compound 31

Synthesis of Intermediate 1-31
Intermediate 1-31 was synthesized in the same manner as used to synthesize Intermediate 1-5 of Synthesis Example 1, except that Compound A-31 was used instead of Compound A-5.
Synthesis of Compound 31
Compound 31 (690 mg, 89% of yield) was synthesized in the same manner as used to synthesize Compound 5 of Synthesis Example 1, except that Intermediate 1-31 and Compound B-30 were used instead of Intermediate 1-5 and Compound B-5, respectively. The obtained compound was identified by MS/FAB and $^1$H NMR.

$C_{62}H_{42}N_4$: calc. 885.03, found 885.03.

$^1$H NMR (CDCl$_3$, 400 MHz) δ(ppm) 8.18-8.15 (m, 2H), 8.06-8.04 (m, 2H), 8.01-7.98 (m, 2H), 7.82-7.76 (m, 4H), 7.72-7.58 (m, 5H), 7.56-7.49 (m, 3H), 7.41-7.28 (m, 7H), 7.24-7.20 (m, 3H), 7.14-7.08 (m, 2H), 6.83-6.80 (m, 2H), 6.71-6.68 (m, 1H), 6.48-6.41 (m, 3H), 1.61 (s, 6H).

Synthesis Example 21: Synthesis of Compound 34

Synthesis of Intermediate 1-34
Intermediate 1-34 was synthesized in the same manner as used to synthesize Intermediate 1-5 of Synthesis Example 1, except that Compound A-34 was used instead of Compound A-5.
Synthesis of Compound 34
Compound 34 (720 mg, 83% of yield) was synthesized in the same manner as used to synthesize Compound 5 of Synthesis Example 1, except that Intermediate 1-34 and Compound B-30 were used instead of Intermediate 1-5 and Compound B-5, respectively. The obtained compound was identified by MS/FAB and $^1$H NMR.

$C_{52}H_{36}N_6$: calc. 744.88, found 744.91.

$^1$H NMR (CDCl$_3$, 400 MHz) δ(ppm) 8.18-8.15 (m, 2H), 8.08-8.04 (m, 2H), 8.01-7.98 (m, 2H), 7.82-7.76 (m, 3H), 7.75-7.64 (m, 5H), 7.61-7.59 (m, 2H), 7.41-7.28 (m, 8H), 7.25-7.20 (m, 3H), 7.08-7.02 (m, 1H), 6.99-6.96 (m, 2H), 2.44 (s, 6H).

Synthesis Example 22: Synthesis of Compound 35

Synthesis of Intermediate 1-35
Intermediate 1-35 was synthesized in the same manner as used to synthesize Intermediate 1-5 of Synthesis Example 1, except that Compound A-35 was used instead of Compound A-5.
Synthesis of Compound 35
Compound 35 (730 mg, 88% of yield) was synthesized in the same manner as used to synthesize Compound 5 of Synthesis Example 1, except that Intermediate 1-35 and Compound B-7 were used instead of Intermediate 1-5 and Compound B-5, respectively. The obtained compound was identified by MS/FAB and $^1$H NMR.

$C_{52}H_{33}N_3F_2$: calc. 749.83, found 749.91.

$^1$H NMR (CDCl$_3$, 400 MHz) δ(ppm) 8.62-8.60 (m, 1H), 8.17-8.07 (m, 4H), 8.01-7.98 (m, 2H), 7.91-7.87 (m, 2H), 7.82-7.60 (m, 2H), 7.76-7.72 (m, 2H), 7.66-7.59 (m, 3H), 7.53-7.45 (m, 5H), 7.28-7.24 (m, 1H), 7.14-7.08 (m, 2H), 7.03-6.95 (m, 6H), 6.91-6.87 (m, 1H), 6.70-6.65 (m, 2H).

Synthesis Example 23: Synthesis of Compound 36

Synthesis of Intermediate 1-36
Intermediate 1-36 was synthesized in the same manner as used to synthesize Intermediate 1-5 of Synthesis Example 1, except that Compound A-36 was used instead of Compound A-5.
Synthesis of Compound 36
Compound 36 (740 mg, 83% of yield) was synthesized in the same manner as used to synthesize Compound 5 of Synthesis Example 1, except that Intermediate 1-36 and Compound B-7 were used instead of Intermediate 1-5 and Compound B-5, respectively. The obtained compound was identified by MS/FAB and $^1$H NMR.

$C_{54}H_{33}N_5$: calc. 763.88, found 763.95.

$^1$H NMR (CDCl$_3$, 400 MHz) δ(ppm) 8.62-8.60 (m, 1H), 8.17-8.07 (m, 4H), 8.01-7.98 (m, 2H), 7.91-7.88 (m, 2H), 7.82-7.76 (m, 2H), 7.76-7.72 (m, 2H), 7.66-7.59 (m, 3H), 7.52-7.44 (m, 5H), 7.38-7.35 (m, 4H), 7.28-7.26 (m, 1H), 6.97-6.87 (m, 3H), 6.82-6.78 (m, 4H).

Synthesis Example 24: Synthesis of Compound 38

Synthesis of Intermediate 1-38
Intermediate 1-38 was synthesized in the same manner as used to synthesize Intermediate 1-5 of Synthesis Example 1, except that Compound A-38 was used instead of Compound A-5.
Synthesis of Compound 38
Compound 38 (950 mg, 86% of yield) was synthesized in the same manner as used to synthesize Compound 5 of Synthesis Example 1, except that Intermediate 1-38 and Compound B-7 were used instead of Intermediate 1-5 and Compound B-5, respectively. The obtained compound was identified by MS/FAB and $^1$H NMR.

$C_{30}H_{43}N_3$: calc. 830.02, found 830.11.

$^1$H NMR (CDCl$_3$, 400 MHz) δ(ppm) 8.62-8.60 (m, 1H), 8.17-8.07 (m, 4H), 8.01-7.98 (m, 2H), 7.91-7.89 (m, 2H), 7.82-7.73 (m, 5H), 7.68-7.45 (m, 9H), 7.35-7.24 (m, 2H), 7.14-7.04 (m, 4H), 6.91-6.87 (m, 1H), 6.69-6.63 (m, 2H), 6.42-6.38 (m, 3H), 6.24-6.21 (m, 2H), 1.61 (s, 6H).

Synthesis Example 25: Synthesis of Compound 44

Synthesis of Intermediate 1-44
Intermediate 1-44 was synthesized in the same manner as used to synthesize Intermediate 1-5 of Synthesis Example 1, except that Compound A-44 was used instead of Compound A-5.
Synthesis of Compound 44
Compound 44 (860 mg, 93% of yield) was synthesized in the same manner as used to synthesize Compound 5 of Synthesis Example 1, except that Intermediate 1-44 and Compound B-43 were used instead of Intermediate 1-5 and Compound B-5, respectively. The obtained compound was identified by MS/FAB and $^1$H NMR.

$C_{61}H_{39}N_5$: calc. 841.99, found 842.05.

$^1$H NMR (CDCl$_3$, 400 MHz) δ(ppm) 8.93-8.91 (m, 1H), 8.84-8.80 (m, 4H), 8.34-8.31 (m, 1H), 8.23-8.09 (m, 5H), 8.01-7.98 (m, 1H), 7.63-7.59 (m, 5H), 7.53-7.47 (m, 6H), 7.42-7.23 (m, 8H), 7.09-7.04 (m, 2H), 6.98-6.94 (m, 2H), 6.87-6.84 (m, 1H), 6.68-6.63 (m, 1H), 6.32-6.29 (m, 2H).

Synthesis Example 26: Synthesis of Compound 48

Synthesis of Intermediate 1-48
Intermediate 1-48 was synthesized in the same manner as used to synthesize Intermediate 1-5 of Synthesis Example 1, except that Compound A-48 was used instead of Compound A-5.
Synthesis of Compound 48
Compound 48 (820 mg, 83% of yield) was synthesized in the same manner as used to synthesize Compound 5 of Synthesis Example 1, except that Intermediate 1-48 and Compound B-51 were used instead of Intermediate 1-5 and Compound B-5, respectively. The obtained compound was identified by MS/FAB and $^1$H NMR.
$C_{45}H_{28}N_2F_5$: calc. 765.76, found 765.80.
$^1$H NMR (CDCl$_3$, 400 MHz) δ(ppm) 8.80-8.72 (m, 4H), 8.17-8.15 (m, 1H), 8.04-7.90 (m, 8H), 7.82-7.80 (m, 1H), 7.61-7.52 (m, 7H), 7.12-7.07 (m, 2H), 5.63-6.58 (m, 3H), 6.43-6.39 (m, 2H).

Synthesis Example 27: Synthesis of Compound 53

Synthesis of Intermediate 1-53
Intermediate 1-53 was synthesized in the same manner as used to synthesize Intermediate 1-5 of Synthesis Example 1, except that Compound A-53 was used instead of Compound A-5.
Synthesis of Compound 53
Compound 53 (490 mg, 78% of yield) was synthesized in the same manner as used to synthesize Compound 5 of Synthesis Example 1, except that Intermediate 1-53 and Compound B-10 were used instead of Intermediate 1-5 and Compound B-5, respectively. The obtained compound was identified by MS/FAB and $^1$H NMR.
$C_{47}H_{28}N_4F_6$: calc. 774.75, found 774.81.
$^1$H NMR (CDCl$_3$, 400 MHz) δ(ppm) 8.50-8.48 (m, 1H), 8.43-8.41 (m, 1H), 8.21-8.10 (m, 5H), 8.01-7.95 (m, 4H), 7.89-7.87 (m, 1H), 7.81 (d, 2H), 7.60 (d, 2H), 7.50-7.46 (m, 6H), 6.97-6.93 (m, 2H), 6.82-6.77 (m, 4H).

Synthesis Example 28: Synthesis of Compound 57

Synthesis of Intermediate 1-57
Intermediate 1-57 was synthesized in the same manner as used to synthesize Intermediate 1-5 of Synthesis Example 1, except that Compound A-57 was used instead of Compound A-5.
Synthesis of Compound 57
Compound 57 (620 mg, 87% of yield) was synthesized in the same manner as used to synthesize Compound 5 of Synthesis Example 1, except that Intermediate 1-57 was used instead of Intermediate 1-5. The obtained compound was identified by MS/FAB and $^1$H NMR.
$C_{43}H_{39}N_3$: calc. 741.91, found 741.99.
$^1$H NMR (CDCl$_3$, 400 MHz) δ(ppm) 8.20-8.18 (m, 2H), 8.12-8.10 (m, 1H), 8.01-7.96 (m, 2H), 7.90-7.75 (m, 6H), 7.66-7.55 (m, 4H), 7.50-7.37 (m, 5H), 7.32-7.21 (m, 2H), 7.08-7.03 (m, 4H), 6.79-6.77 (m, 1H), 6.65-6.61 (m, 2H), 6.06-6.04 (m, 4H), 2.24 (s, 3H), 2.20 (s, 3H).

Synthesis Example 29: Synthesis of Compound 58

Synthesis of Intermediate 1-58
Intermediate 1-58 was synthesized in the same manner as used to synthesize Intermediate 1-5 of Synthesis Example 1, except that Compound A-58 was used instead of Compound A-5.
Synthesis of Compound 58
Compound 58 (650 mg, 84% of yield) was synthesized in the same manner as used to synthesize Compound 5 of Synthesis Example 1, except that Intermediate 1-58 was used instead of Intermediate 1-5. The obtained compound was identified by MS/FAB and $^1$H NMR.
$C_{53}H_{31}N_3F_4$: calc. 785.82, found 785.91.
$^1$H NMR (CDCl$_3$, 400 MHz) δ(ppm) 8.40-8.38 (m, 2H), 8.31-8.28 (m, 1H), 8.22-8.17 (m, 3H), 8.12-8.10 (m, 1H), 8.01-7.98 (m, 1H), 7.81-7.78 (m, 3H), 7.66-7.52 (m, 4H), 7.44-7.37 (m, 3H), 7.32-7.20 (m, 2H), 7.12-7.07 (m, 4H), 6.63-6.60 (m, 3H), 6.36-6.34 (m, 4H).

Synthesis Example 30: Synthesis of Compound 61

Synthesis of Intermediate 1-61
Intermediate 1-61 was synthesized in the same manner as used to synthesize Intermediate 1-5 of Synthesis Example 1, except that Compound A-61 was used instead of Compound A-5.
Synthesis of Compound 61
Compound 61 (640 mg, 86% of yield) was synthesized in the same manner as used to synthesize Compound 5 of Synthesis Example 1, except that Intermediate 1-61 was used instead of Intermediate 1-5. The obtained compound was identified by MS/FAB and $^1$H NMR.
$C_{61}H_{39}N_3$: calc. 813.98, found 814.02.
$^1$H NMR (CDCl$_3$, 400 MHz) δ(ppm) 8.29-8.17 (m, 5H), 8.12-8.06 (m, 2H), 8.01-7.94 (m, 3H), 7.86-7.74 (m, 6H), 7.68-7.52 (m, 7H), 7.44-7.35 (m, 3H), 7.32-7.21 (m, 2H), 7.09-7.04 (m, 4H), 6.89-6.86 (m, 1H), 6.66-6.63 (m, 2H), 6.20-6.16 (m, 4H).

Synthesis Example 31: Synthesis of Compound 64

Synthesis of Intermediate 1-64
Intermediate 1-64 was synthesized in the same manner as used to synthesize Intermediate 1-5 of Synthesis Example 1, except that Compound A-64 was used instead of Compound A-5.
Synthesis of Compound 64
Compound 64 (820 mg, 81% of yield) was synthesized in the same manner as used to synthesize Compound 5 of Synthesis Example 1, except that Intermediate 1-61 and Compound B-43 were used instead of Intermediate 1-5 and Compound B-5, respectively. The obtained compound was identified by MS/FAB and $^1$H NMR.
$C_{61}H_{39}N_5$: calc. 841.99, found 842.01.
$^1$H NMR (CDCl$_3$, 400 MHz) δ(ppm) 8.93-8.91 (m, 1H), 8.85-8.80 (m, 4H), 8.34-8.30 (m, 2H), 8.23-8.12 (m, 4H), 7.77-7.75 (m, 1H), 7.69-7.59 (m, 6H), 7.52-7.45 (m, 5H), 7.42-7.22 (m, 5H), 7.09-7.05 (m, 4H), 6.86-6.84 (m, 1H), 6.66-6.63 (m, 2H), 6.24-6.20 (m, 4H).

Synthesis Example 32: Synthesis of Compound 65

Synthesis of Intermediate 1-65
Intermediate 1-65 was synthesized in the same manner as used to synthesize Intermediate 1-5 of Synthesis Example 1, except that Compound A-65 was used instead of Compound A-5.
Synthesis of Compound 65
Compound 65 (770 mg, 79% of yield) was synthesized in the same manner as used to synthesize Compound 5 of Synthesis Example 1, except that Intermediate 1-65 and Compound B-43 were used instead of Intermediate 1-5 and Compound B-5, respectively. The obtained compound was identified by MS/FAB and $^1$H NMR.

$C_{55}H_{34}N_4S$: calc. 782.95, found 783.00.

$^1$H NMR (CDCl$_3$, 400 MHz) δ(ppm) 8.93-8.91 (m, 1H), 8.83-8.75 (m, 4H), 8.50-8.48 (m, 1H), 8.34-8.32 (m, 1H), 8.23-8.18 (m, 2H), 8.12-8.08 (m, 3H), 7.98-7.96 (m, 1H), 7.86-7.84 (m, 1H), 7.78-7.76 (m, 1H), 7.70-7.59 (m, 5H), 7.42-7.38 (m, 2H), 7.12-7.04 (m, 5H), 6.93-6.91 (m, 1H), 6.66-6.63 (m, 2H), 6.36-6.30 (m, 4H).

Synthesis Example 33: Synthesis of Compound 66

Synthesis of Intermediate 1-66

Intermediate 1-66 was synthesized in the same manner as used to synthesize Intermediate 1-5 of Synthesis Example 1, except that Compound A-66 was used instead of Compound A-5.

Synthesis of Compound 66

Compound 66 (810 mg, 88% of yield) was synthesized in the same manner as used to synthesize Compound 5 of Synthesis Example 1, except that Intermediate 1-66 and Compound B-10 were used instead of Intermediate 1-5 and Compound B-5, respectively. The obtained compound was identified by MS/FAB and $^1$H NMR.

$C_{50}H_{32}N_4$: calc. 688.81, found 688.89.

$^1$H NMR (CDCl$_3$, 400 MHz) δ(ppm) 8.50-8.48 (m, 1H), 8.43-8.41 (m, 1H), 8.21-8.18 (m, 2H), 8.12-8.10 (m, 1H), 8.03-7.85 (m, 8H), 7.71-7.69 (m, 1H), 7.61-7.59 (m, 1H), 7.51-7.46 (m, 3H), 7.18-7.16 (m, 1H), 7.10-7.01 (m, 6H), 6.82-6.80 (m, 1H), 6.65-6.61 (m, 2H), 6.08-6.05 (m, 4H).

Synthesis Example 34: Synthesis of Compound 68

Compound 68 (590 mg, 75% of yield) was synthesized in the same manner as used to synthesize Compound 5 of Synthesis Example 1, except that Compound B-68 was used instead of Compound B-5. The obtained compound was identified by MS/FAB and $^1$H NMR.

$C_{51}H_{32}N_2S$: calc. 704.87, found 704.92.

$^1$H NMR (CDCl$_3$, 400 MHz) δ(ppm) 8.88-8.86 (m, 1H), 8.80-8.78 (m, 1H), 8.48-8.46 (m, 1H), 8.17-7.87 (m, 10H), 7.80-7.78 (m, 1H), 7.67-7.42 (m, 6H), 7.08-7.04 (m, 4H), 6.97-6.93 (m, 2H), 6.66-6.63 (m, 2H), 6.16-6.00 (m, 4H).

Synthesis Example 35: Synthesis of Compound 69

Compound 69 (690 mg, 81% of yield) was synthesized in the same manner as used to synthesize Compound 5 of Synthesis Example 1, except that Compound B-69 was used instead of Compound B-5. The obtained compound was identified by MS/FAB and $^1$H NMR.

$C_{51}H_{32}N_2O$: calc. 688.81, found 688.89.

$^1$H NMR (CDCl$_3$, 400 MHz) δ(ppm) 8.88-8.86 (m, 1H), 8.80-8.78 (m, 1H), 8.34-8.31 (m, 1H), 8.17-8.15 (m, 1H), 8.06-7.89 (m, 7H), 7.79-7.46 (m, 8H), 7.35-7.32 (m, 1H), 7.08-7.04 (m, 4H), 6.97-6.93 (m, 2H), 6.66-6.63 (m, 2H), 6.16-6.10 (m, 4H).

Synthesis Example 36: Synthesis of Compound 70

Compound 70 (770 mg, 86% of yield) was synthesized in the same manner as used to synthesize Compound 5 of Synthesis Example 1, except that Compound B-70 was used instead of Compound B-5. The obtained compound was identified by MS/FAB and $^1$H NMR.

$C_{55}H_{36}N_2S$: calc. 756.95, found 760.02.

$^1$H NMR (CDCl$_3$, 400 MHz) δ(ppm) 8.33-8.29 (m, 2H), 8.17-8.10 (m, 2H), 8.01-7.94 (m, 4H), 7.85-7.76 (m, 6H), 7.61-7.43 (m, 9H), 7.36-7.32 (m, 1H), 7.08-7.03 (m, 4H), 6.96-6.93 (m, 2H), 6.66-6.63 (m, 2H), 6.16-6.10 (m, 4H).

Synthesis Example 37: Synthesis of Compound 71

Compound 71 (740 mg, 89% of yield) was synthesized in the same manner as used to synthesize Compound 5 of Synthesis Example 1, except that Compound B-71 was used instead of Compound B-5. The obtained compound was identified by MS/FAB and $^1$H NMR.

$C_{55}H_{36}N_2O$: calc. 740.88, found 740.95.

$^1$H NMR (CDCl$_3$, 400 MHz) δ(ppm) 8.27-8.24 (m, 2H), 8.17-8.10 (m, 2H), 8.01-7.98 (m, 2H), 7.91-7.88 (m, 2H), 7.82-7.67 (m, 6H), 7.61-7.45 (m, 7H), 7.38-7.32 (m, 3H), 7.08-7.03 (m, 4H), 6.97-6.93 (m, 2H), 6.66-6.63 (m, 2H), 6.16-6.10 (m, 4H).

Example 1

An anode was prepared by cutting a Corning 15 Ωcm$^2$ (1200 Å) ITO glass substrate to a size of 50 mm×50 m×0.7 mm, ultrasonically cleaning the glass substrate using isopropyl alcohol and pure water for 5 minutes each, and then irradiating UV light for 30 minutes and exposing to ozone to clean. Then, the anode was loaded into a vacuum deposition apparatus.

2-TNATA was deposited on the ITO layer to form an HIL having a thickness of 600 Å, and then, NPB was deposited on the HIL to form an HTL having a thickness of 300 Å.

Subsequently, 9,10-di-naphthalen-2-yl-anthracene (DNA, host) and Compound 5 (dopant) were co-deposited on the HTL at a weight ratio of 98:2 to form an EML having a thickness of 300 Å.

Thereafter, Alq$_3$ was deposited on the EML to form an ETL having a thickness of 300 Å, and LIF was deposited on the ETL to form an EIL having a thickness of 10 Å, and then, Al was deposited on the EIL to form a second electrode (cathode) having a thickness of 3000 Å, thereby manufacturing of an organic light-emitting diode.

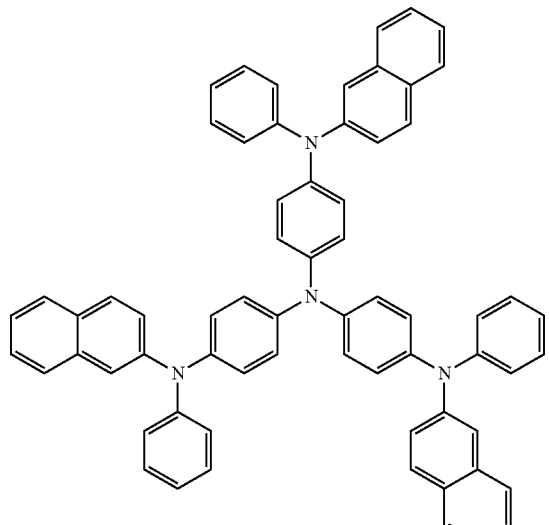

2-TNATA

-continued

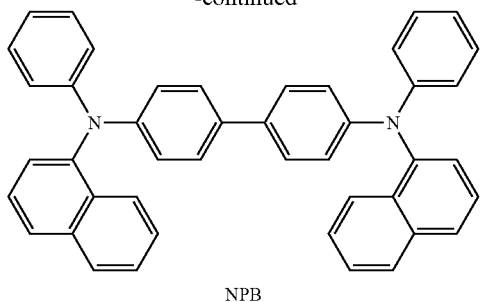

NPB

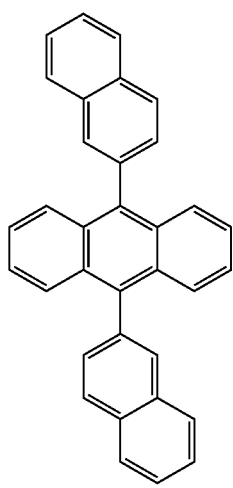

DNA

Example 2

An organic light-emitting diode was manufactured in the same manner as in Example 1, except that Compound 17 was used instead of Compound 5 in forming the EML.

Example 3

An organic light-emitting diode was manufactured in the same manner as in Example 1, except that Compound 21 was used instead of Compound 5 in forming the EML.

Example 4

An organic light-emitting diode was manufactured in the same manner as in Example 1, except that Compound 30 was used instead of Compound 5 in forming the EML.

Example 5

An organic light-emitting diode was manufactured in the same manner as in Example 1, except that Compound 43 was used instead of Compound 5 in forming the EML.

Example 6

An organic light-emitting diode was manufactured in the same manner as in Example 1, except that Compound 51 was used instead of Compound 5 in forming the EML.

Example 7

An organic light-emitting diode was manufactured in the same manner as in Example 1, except that Compound 59 was used instead of Compound 5 in forming the EML.

Comparative Example 1

An organic light-emitting diode was manufactured in the same manner as in Example 1, except that DPVBi was used instead of Compound 5 in forming the EML.

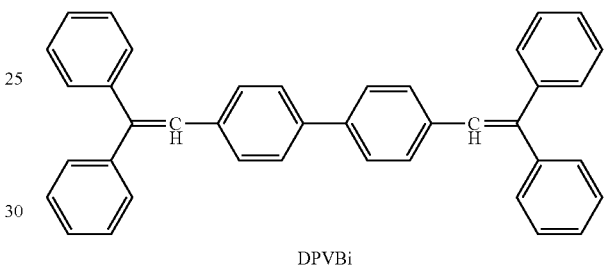

DPVBi

Comparative Example 2

An organic light-emitting diode was manufactured in the same manner as in Example 1, except that Compound A below was used instead of Compound 5 in forming the EML:

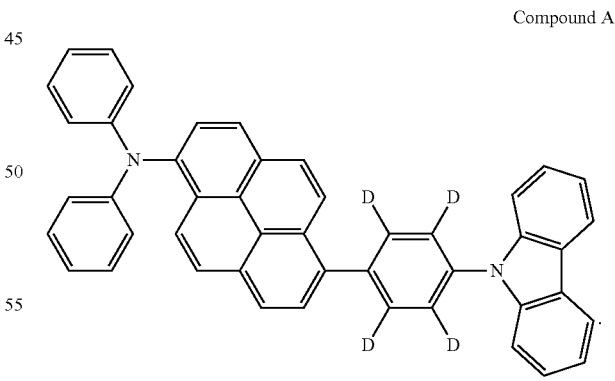

Compound A

Comparative Example 3

An organic light-emitting diode was manufactured in the same manner as in Example 1, except that Compound B below was used instead of Compound 5 in forming the EML:

Compound B

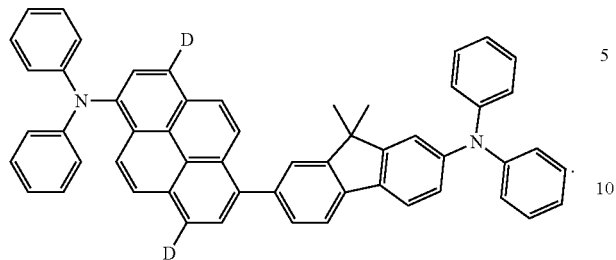

Comparative Example 4

An organic light-emitting diode was manufactured in the same manner as in Example 1, except that Compound C below was used instead of Compound 5 in forming the EML:

Compound C

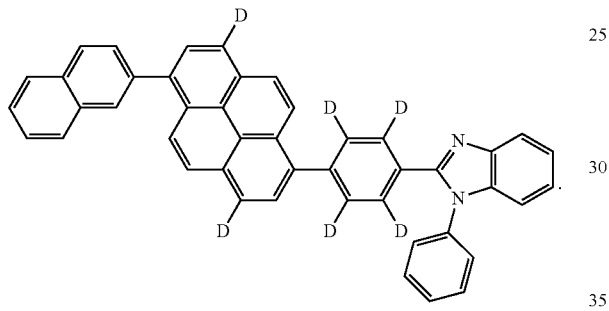

Comparative Example 5

An organic light-emitting diode was manufactured in the same manner as in Example 1, except that Compound D below was used instead of Compound 5 in forming the EML:

Compound D

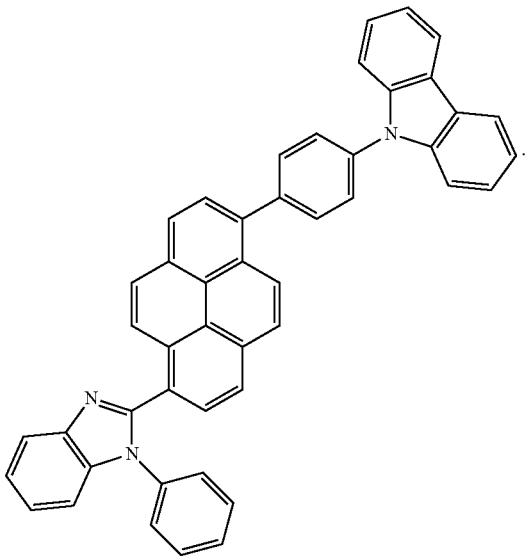

Evaluation Example 1

Driving voltage, current density, brightness, luminescence color, efficiency, and half-life lifetime (@50 mA/cm$^2$) of the organic light-emitting diodes of Examples 1 to 7 and Comparative Examples 1 and 5 were evaluated by using PR650 Spectroscan Source Measurement Unit (a product of PhotoResearch Company). Results thereof are shown in Table 1 below.

TABLE 1

| | Dopant | Driving voltage (V) | Current density (mA/cm$^2$) | Brightness (cd/m$^2$) | Efficiency (cd/A) | Luminescence color | Half-life lifetime (hr) |
|---|---|---|---|---|---|---|---|
| Example 1 | Compound 5 | 6.52 | 50 | 2,850 | 5.70 | Blue | 273 |
| Example 2 | Compound 17 | 6.58 | 50 | 2,810 | 5.62 | Blue | 245 |
| Example 3 | Compound 21 | 6.35 | 50 | 2,780 | 5.56 | Blue | 221 |
| Example 4 | Compound 30 | 6.40 | 50 | 2,915 | 5.83 | Blue | 278 |
| Example 5 | Compound 43 | 6.48 | 50 | 2,571 | 5.14 | Blue | 235 |
| Example 6 | Compound 51 | 6.59 | 50 | 2,350 | 4.70 | Blue | 189 |
| Example 7 | Compound 59 | 6.48 | 50 | 2,847 | 5.69 | Blue | 268 |
| Comparative Example 1 | DPAVBi | 7.85 | 50 | 1,560 | 3.12 | Blue | 113 |
| Comparative Example 2 | Compound A | 6.85 | 50 | 1,900 | 3.90 | Blue | 100 |
| Comparative Example 3 | Compound B | 6.80 | 50 | 2,000 | 4.00 | Blue | 122 |
| Comparative Example 4 | Compound C | 6.85 | 50 | 2,152 | 4.30 | Blue | 108 |
| Comparative Example 5 | Compound D | 6.90 | 50 | 2,180 | 4.36 | Blue | 103 |

From Table 1, it is confirmed that the organic light-emitting diodes of Examples 1 to 7 had better driving voltage, brightness, efficiency, color purity, and/or lifetime characteristics than the organic light-emitting diodes of Comparative Examples 1 to 5.

An organic light-emitting device including the pyrene-based compound may have a low driving voltage, high brightness, high efficiency, and/or a long lifespan.

While the present invention has been particularly shown and described with reference to exemplary embodiments thereof, it will be understood by those of ordinary skill in the art that various changes in form and details may be made therein. The present invention is not limited to the disclosed embodiments, but, on the contrary, is intended to cover various modifications and equivalent arrangements included within the spirit and scope of the appended claims, and equivalents thereof.

What is claimed is:

1. A pyrene-based compound represented by Formula 1 below:

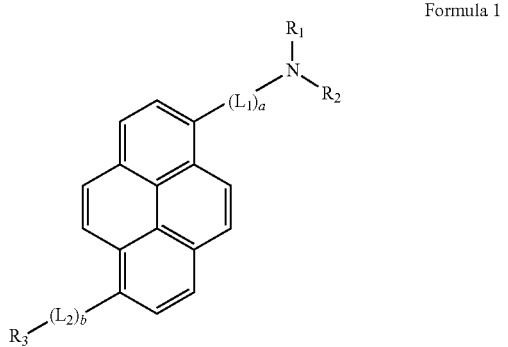

Formula 1 wherein in Formula 1:
$L_1$ and $L_2$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, and a substituted or unsubstituted $C_2$-$C_{60}$ heteroarylene group;
a is an integer from 1 to 3;
b is an integer from 0 to 3;
$R_1$ and $R_2$ are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, and a substituted or unsubstituted $C_2$-$C_{60}$ heteroaryl group; and
$R_3$ is an electron transporting group selected from
i) a pyrrolyl group, an imidazolyl group, a pyrazolyl group, a triazolyl group, a oxazolyl group, an isoxazolyl group, an oxadiazolyl group, an oxatriazolyl group, a thiazolyl group, an isothiazolyl group, a thiadiazolyl group, a thioatriazolyl group, a benzoimidazolyl group, an imidazopyrimidinyl group, an imidazopyridinyl group, a benzoxazolyl group, a benzothiazolyl group, a pyridinyl group, a pyrimidinyl group, a pyrazinyl group, a triazinyl group, a quinolinyl group, an isoquinolinyl group, an indolyl group, a phthalazinyl group, a quinoxalinyl group, and a quinazolinyl group; and
ii) a pyrrolyl group, an imidazolyl group, a pyrazolyl group, a triazolyl group, a oxazolyl group, an isoxazolyl group, an oxadiazolyl group, an oxatriazolyl group, a thiazolyl group, an isothiazolyl group, a thiadiazolyl group, a thioatriazolyl group, benzoimidazolyl group, an imidazopyrimidinyl group, an imidazopyridinyl group, a benzoxazolyl group, benzothiazolyl group, a pyridinyl group, a pyrimidinyl group, a pyrazinyl group, a triazinyl group, a quinolinyl group, an isoquinolinyl group, an indolyl group, a phthalazinyl group, a quinoxalinyl group and a quinazolinyl group, each substituted with at least one substituent selected from
a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;
a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;
a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and
—Si($Q_{13}$)($Q_{14}$)($Q_{15}$) wherein $Q_{13}$ to $Q_{15}$ are each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

2. The pyrene-based compound of claim 1, wherein $L_1$ and $L_2$ are each independently selected from
i) phenylene, pentalenylene, indenylene, naphtylene, azulenylene, heptalenylene, indacenylene, acenaphtylene, fluorenylene, spiro-fluorenylene, phenalenylene, phenanthrenylene, anthrylene, fluoranthenylene, triphenylenylene, pyrenylene, chrysenylene, naphthacenylene, picenylene, perylenylene, pentaphenylene, hexacenylene, pyrrolylene, imidazolylene, pyrazolylene, pyridinylene, pyrazinylene, pyrimidinylene, pyridazinylene, isoindolylene, indolylene, indazolylene, purinylene, quinolinylene, benzoquinolinylene, phthalazinylene, naphthyridinylene, quinoxalinylene, quinazolinylene, cinnolinylene, carbazolylene, phenanthridinylene, acridinylene, phenanthrolinylene, phenazinylene, benzooxazolylene, benzoimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazolylene, triazinylene, benzooxazolylene, dibenzofuranylene, dibenzothiophenylene, and benzocarbazolylene; and ii) phenylene, pentalenylene, indenylene, naphtylene, azulenylene, heptalenylene, indacenylene, acenaphtylene, fluorenylene, spiro-fluorenylene, phenalenylene, phenanthrenylene, anthrylene, fluoranthenylene, triphenylenylene, pyrenylene, chrysenylene, naphthacenylene, picenylene, perylenylene, pentaphenylene, hexacenylene, pyrrolylene, imidazolylene, pyrazolylene, pyridinylene, pyrazinylene, pyrimidinylene, pyridazinylene, isoindolylene, indolylene, indazolylene, purinylene, quinolinylene, benzoquinolinylene, phthalazinylene, naphthyridinylene, quinoxalinylene, quinazolinylene, cinnolinylene, carbazolylene, phenanthridinylene, acridinylene, phenanthrolinylene, phenazinylene, benzooxazolylene, benzoimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazolylene, triazinylene, benzooxazolylene, dibenzofuranylene, dibenzothiophenylene, and benzocarbazolylene, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{20}$ aryl group and a $C_2$-$C_{20}$ heteroaryl group; and a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

3. The pyrene-based compound of claim 1, wherein $L_1$ and $L_2$ are each independently represented by one of Formulae 2-1 to 2-27 below:

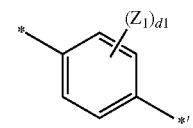

Formula 2-1

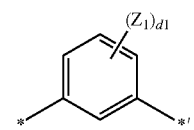

Formula 2-2

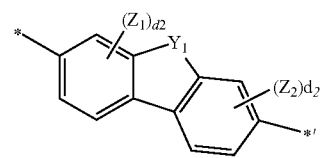

Formula 2-3

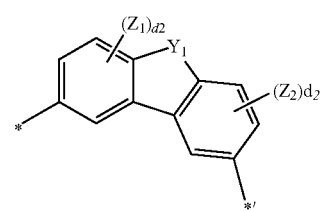

Formula 2-4

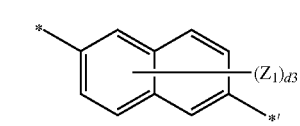

Formula 2-5

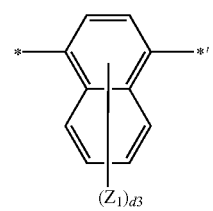

Formula 2-6

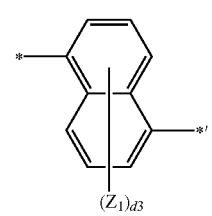

Formula 2-7

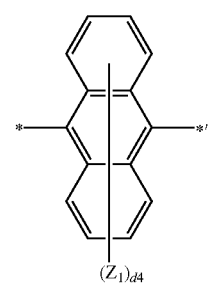

Formula 2-8

-continued

Formula 2-9
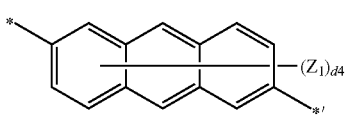

Formula 2-10
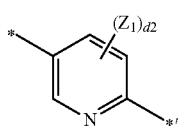

Formula 2-11
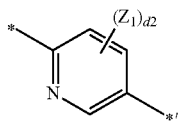

Formula 2-12
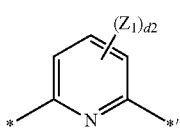

Formula 2-13
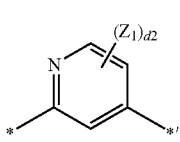

Formula 2-14

Formula 2-15
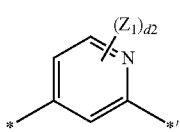

Formula 2-16
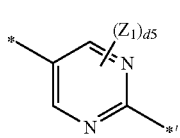

Formula 2-17
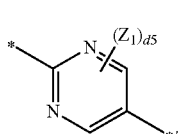

Formula 2-18
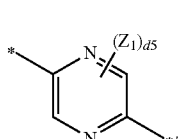

Formula 2-19
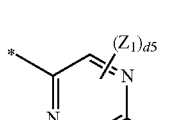

Formula 2-20
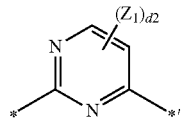

Formula 2-21

Formula 2-22
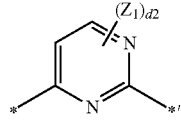

Formula 2-23
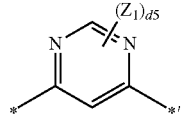

Formula 2-24
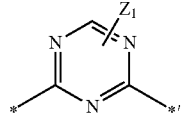

Formula 2-25
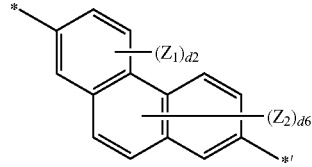

Formula 2-26
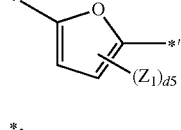

Formula 2-27
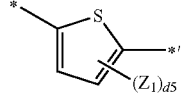

in Formulae 2-1 to 2-27,
$Y_1$ is O, S, $C(Z_3)(Z_4)$, or $N(Z_5)$;
$Z_1$ to $Z_5$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;
a $C_6$-$C_{20}$ aryl group and a $C_2$-$C_{20}$ heteroaryl group; and
a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group;

d1 is an integer from 1 to 4;
d2 is an integer from 1 to 3;
d3 is an integer from 1 to 6;
d4 is an integer from 1 to 8;
d5 is 1 or 2;
d6 is an integer from 1 to 5;
* is a binding site with the pyrene core in Formula 1 or a binding site with a neighboring $L_1$ or $L_2$; and
*' is a binding site with a neighboring $L_1$ or $L_2$ in Formula 1, or a binding site with $R_3$ or N.

4. The pyrene-based compound of claim 3, wherein
$Z_1$ to $Z_5$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —Si($Q_{13}$)($Q_{14}$)($Q_{15}$) wherein $Q_{13}$ to $Q_{15}$ are each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

5. The pyrene-based compound of claim 1, wherein
$L_1$ and $L_2$ are each independently represented by one of Formulae 3-1 to 3-15 below:

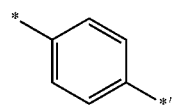

Formula 3-1

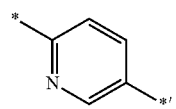

Formula 3-2

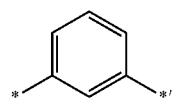

Formula 3-3

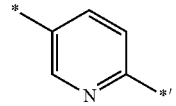

Formula 3-4

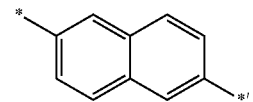

Formula 3-5

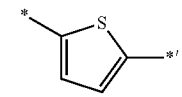

Formula 3-6

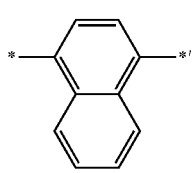

Formula 3-7

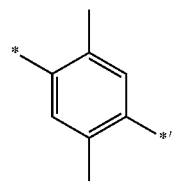

Formula 3-8

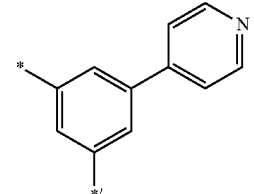

Formula 3-9

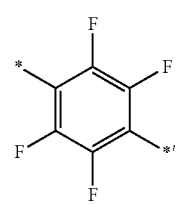

Formula 3-10

-continued

Formula 3-11

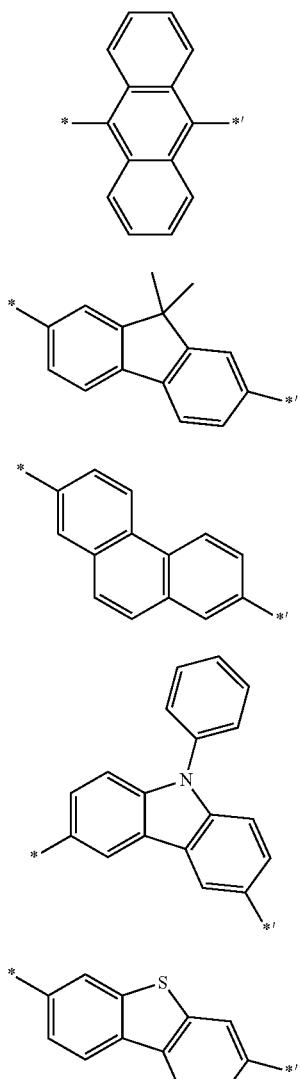

Formula 3-12

Formula 3-13

Formula 3-14

Formula 3-15

* is a binding site with the pyrene core in Formula 1 or a binding site with a neighboring L₁ or L₂; and
*' is a binding site with a neighboring L₁ or L₂ in Formula 1 or a binding site with R₃ or N.

6. The pyrene-based compound of claim 1, wherein a is 1 or 2.

7. The pyrene-based compound of claim 1, wherein R₃ is represented by one of Formulae 4-1 to 4-14 below:

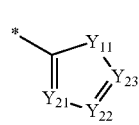

Formula 4-1

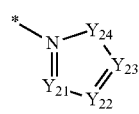

Formula 4-2

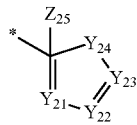

Formula 4-3

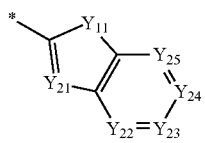

Formula 4-4

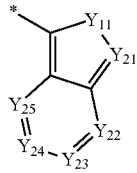

Formula 4-5

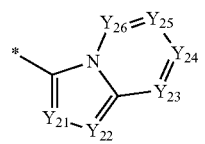

Formula 4-6

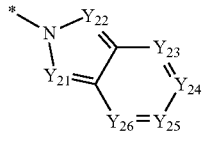

Formula 4-7

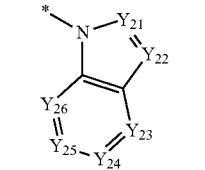

Formula 4-8

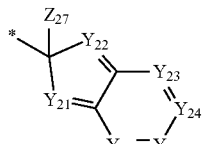

Formula 4-9

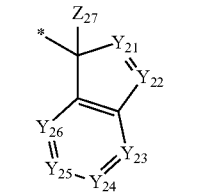

Formula 4-10

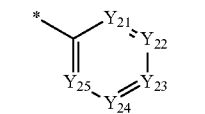

Formula 4-11

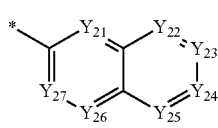

Formula 4-12

Formula 4-13

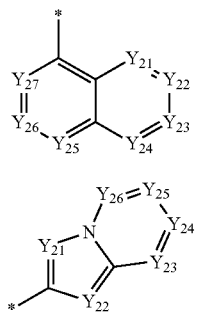

Formula 4-14 in Formulae 4-1 to 4-14, $Y_{11}$ is O, S, N($Z_{11}$), or C($Z_{12}$)($Z_{13}$);
$Y_{21}$ is N, or C($Z_{21}$);
$Y_{22}$ is N, or C($Z_{22}$);
$Y_{23}$ is N, or C($Z_{23}$);
$Y_{24}$ is N, or C($Z_{24}$);
$Y_{25}$ is N, or C($Z_{25}$);
$Y_{26}$ is N, or C($Z_{26}$);
$Y_{27}$ is N, or C($Z_{27}$);
$Z_{11}$ to $Z_{13}$ and $Z_{21}$ to $Z_{27}$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{20}$ aryl group and a $C_2$-$C_{20}$ heteroaryl group;

a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —Si($Q_{13}$)($Q_{14}$)($Q_{15}$) wherein $Q_{13}$ to $Q_{15}$ are each independently selected from a $C_1$-$C_{20}$ alkyl group, a $C_1$-$C_{20}$ alkoxy group, a $C_6$-$C_{20}$ aryl group, and a $C_2$-$C_{20}$ heteroaryl group; and

* is a binding site with $L_1$ in Formula 1.

8. The pyrene-based compound of claim 7, wherein
$Z_{11}$ to $Z_{13}$ and $Z_{21}$ to $Z_{27}$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —Si($Q_{13}$)($Q_{14}$)($Q_{15}$) wherein $Q_{13}$ to $Q_{15}$ are each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

9. The pyrene-based compound of claim 1, wherein
$R_3$ is selected from Formulae 4-1(1), 4-1(2), 4-1(3), 4-4(1), 4-4(2), 4-4(3), 4-6(1), 4-6(2), 4-8(1), 4-11(1), 4-11(2), 4-11(3), 4-11(4), 4-12(1), 4-14(1), and 4-14(2) below:

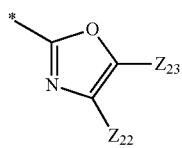

Formula 4-1(1)

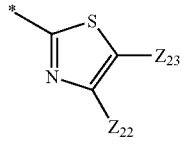

Formula 4-1(2)

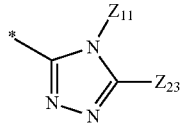

Formula 4-1(3)

Formula 4-4(1)
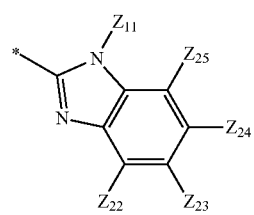

Formula 4-4(2)
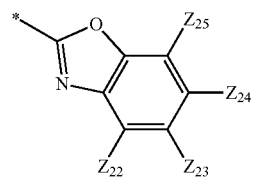

Formula 4-4(3)
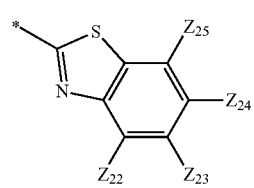

Formula 4-6(1)
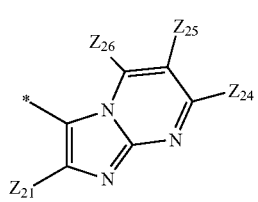

Formula 4-6(2)
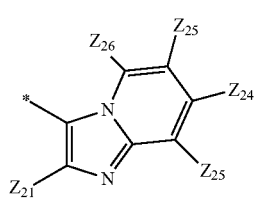

Formula 4-8(1)
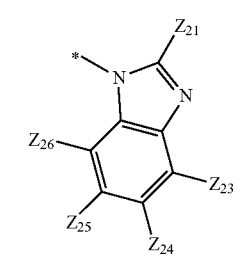

Formula 4-11(1)
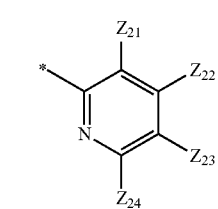

Formula 4-11(2)
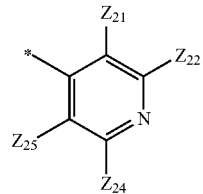

Formula 4-11(3)
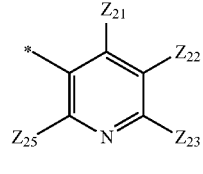

Formula 4-11(4)
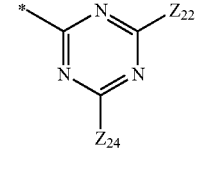

Formula 4-12(1)
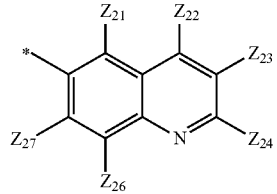

Formula 4-14(1)
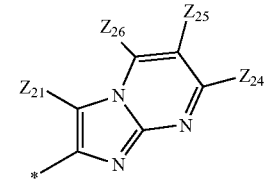

Formula 4-14(2)
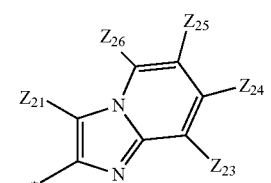

in Formulae 4-1(1), 4-1(2), 4-1(3), 4-4(1), 4-4(2), 4-4(3), 4-6(1), 4-6(2), 4-8(1), 4-11(1), 4-11(2), 4-11(3), 4-11(4), 4-12(1), 4-14(1) and 4-14(2), $Z_{11}$ and $Z_{21}$ and $Z_{21}$ to $Z_{26}$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —Si($Q_{13}$)($Q_{14}$)($Q_{15}$) wherein $Q_{13}$ to $Q_{15}$ are each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, or an isoquinolyl group, and

* is a binding site with $L_2$ or a pyrene core in Formula 1.

10. The pyrene-based compound of claim 1, wherein $R_1$ and $R_2$ are each independently selected from i) phenyl, pentalenyl, indenyl, naphtyl, azulenyl, heptalenyl, indacenyl, acenaphtyl, fluorenyl, spiro-a fluorenyl, phenalenyl, phenanthrenyl, anthryl, fluoranthenyl, triphenylenylene, pyrenyl, chrysenyl, naphthacenyl, picenyl, perylenyl, pentaphenyl, hexacenyl, pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazolyl, oxadiazolylene, triazinylene, benzooxazolyl, dibenzofuranyl, dibenzothiophenyl, and benzocarbazolyl; and ii) phenyl, pentalenyl, indenyl, naphtyl, azulenyl, heptalenyl, indacenyl, acenaphtyl, fluorenyl, spiro-a fluorenyl, phenalenyl, phenanthrenyl, anthryl, fluoranthenyl, triphenylenylene, pyrenyl, chrysenyl, naphthacenyl, picenyl, perylenyl, pentaphenyl, hexacenyl, pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazolyl, oxadiazolylene, triazinylene, benzooxazolyl, dibenzofuranyl, dibenzothiophenyl, and benzocarbazolyl, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{20}$ aryl group and a $C_2$-$C_{20}$ heteroaryl group; and a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

11. The pyrene-based compound of claim 1, wherein $R_1$ and $R_2$ are each independently selected from Formulae 5-1 to 5-13 below:

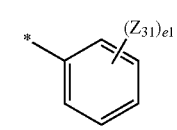

Formula 5-1

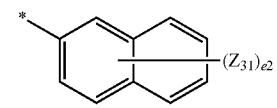

Formula 5-2

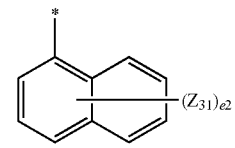

Formula 5-3

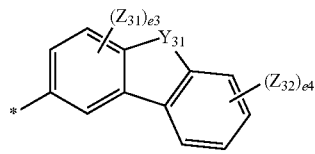

Formula 5-4

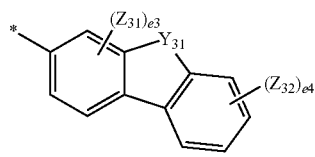

Formula 5-5

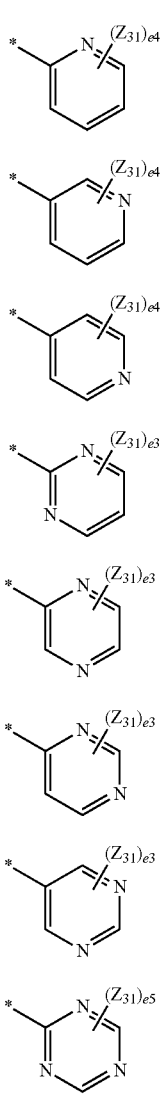

in Formulae 5-1 to 5-13,
$Y_{31}$ is O, S, $C(Z_{33})(Z_{34})$, or $N(Z_{35})$;
$Z_{31}$ to $Z_{35}$ are each independently selected from
a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;
a $C_6$-$C_{20}$ aryl group and a $C_2$-$C_{20}$ heteroaryl group; and
a $C_6$-$C_{20}$ aryl group and a $C_2$-$C_{20}$ heteroaryl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and e1 is an integer from 1 to 5;

e2 is an integer from 1 to 7;

e3 is an integer from 1 to 3;

e4 is an integer from 1 to 4;

e5 is 1 or 2; and

* is a binding site with N in Formula 1.

12. The pyrene-based compound of claim 11, wherein $Z_{31}$ to $Z_{35}$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group; and —Si($Q_{13}$)($Q_{14}$)($Q_{15}$) wherein $Q_{13}$ to $Q_{15}$ are each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

13. The pyrene-based compound of claim 1, wherein the pyrene-based compound is selected from one of Compounds 1 to 71 below:

153
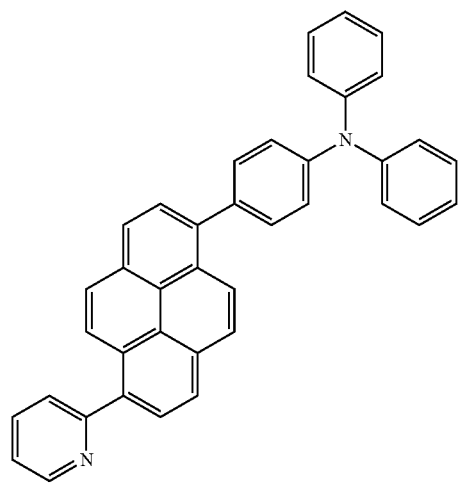
154
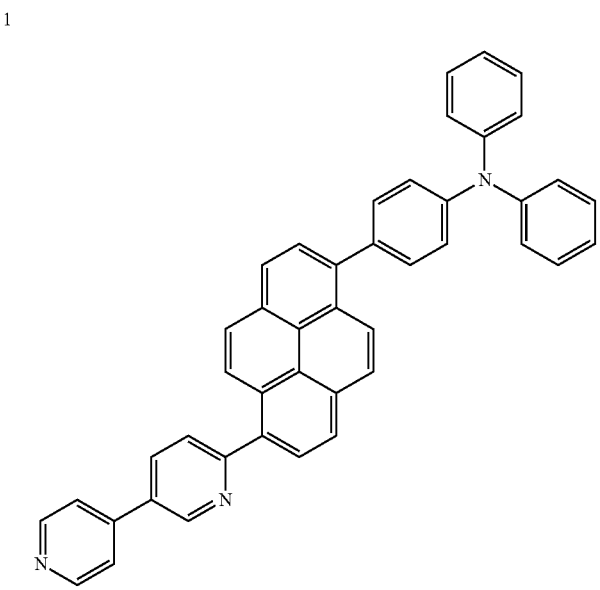
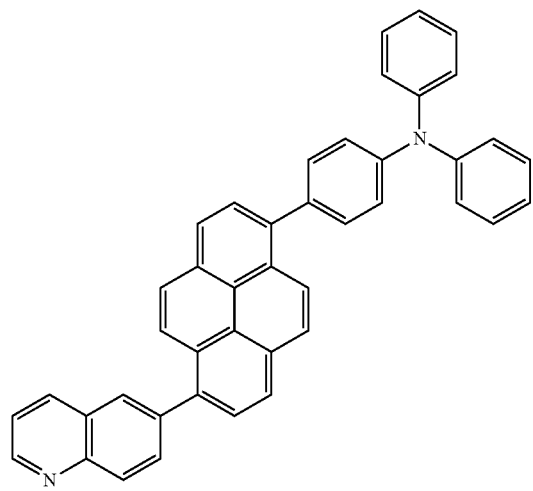
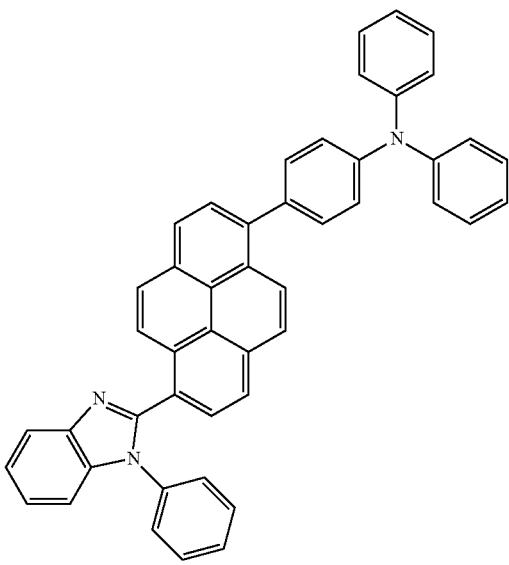

5
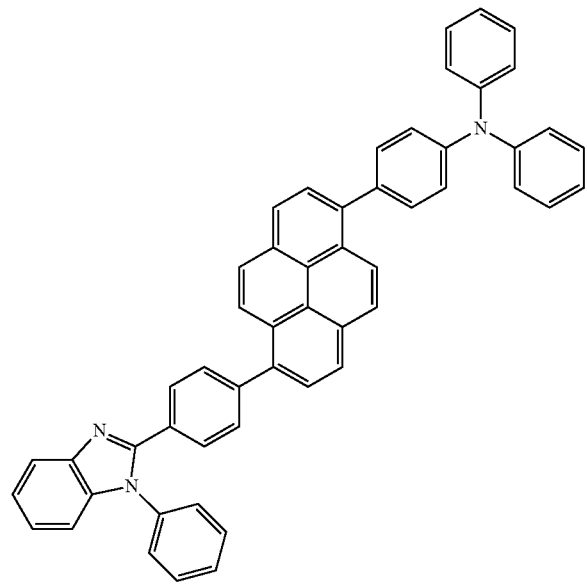
6
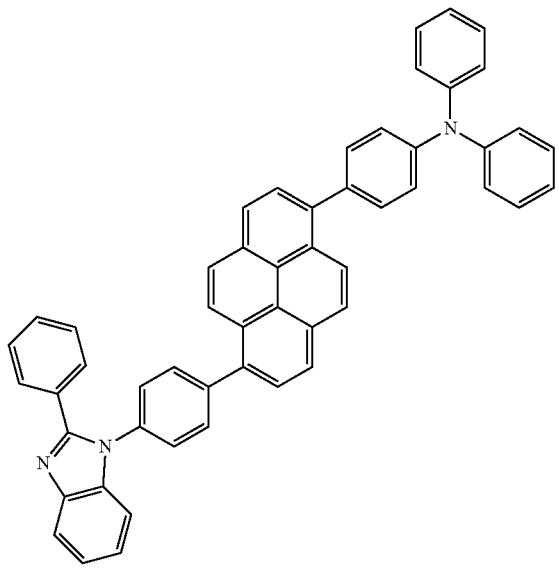
7
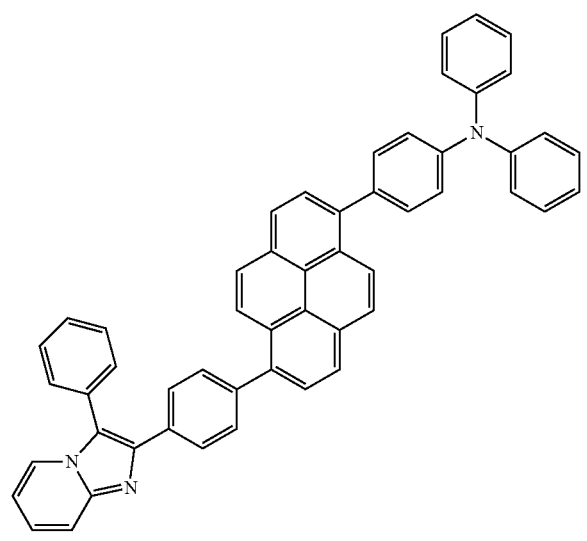
8
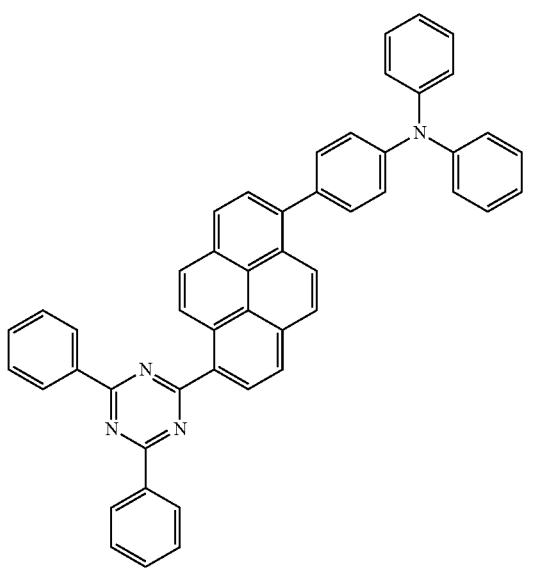

-continued
9
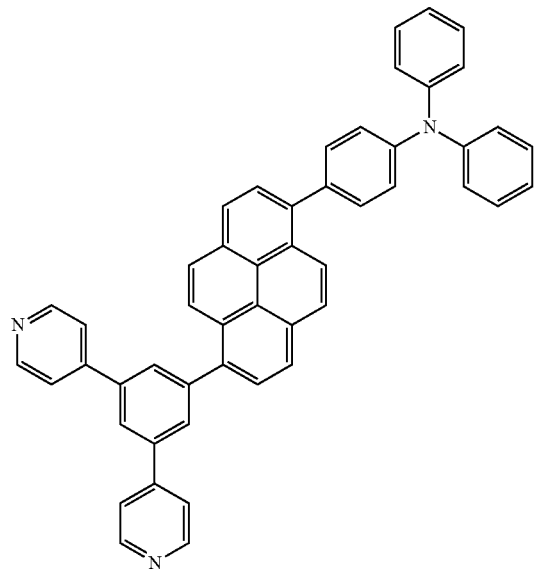
10
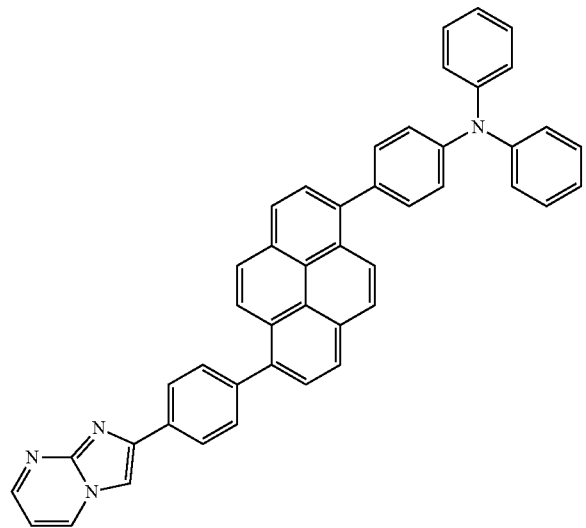
11
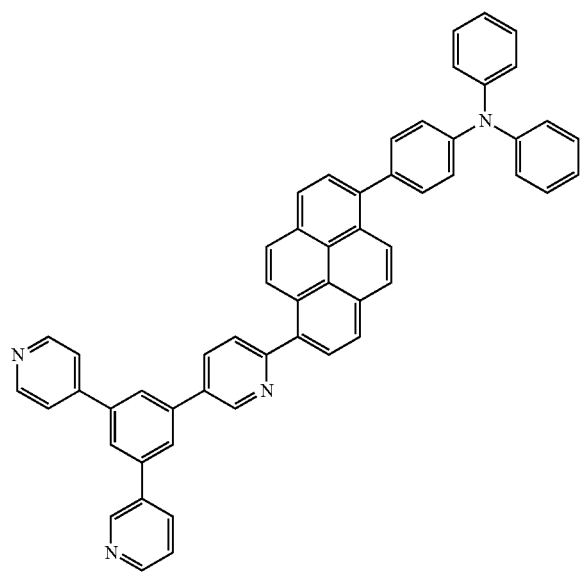
12
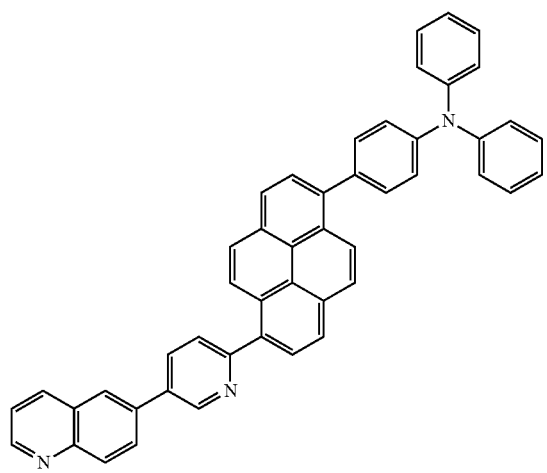

-continued
13
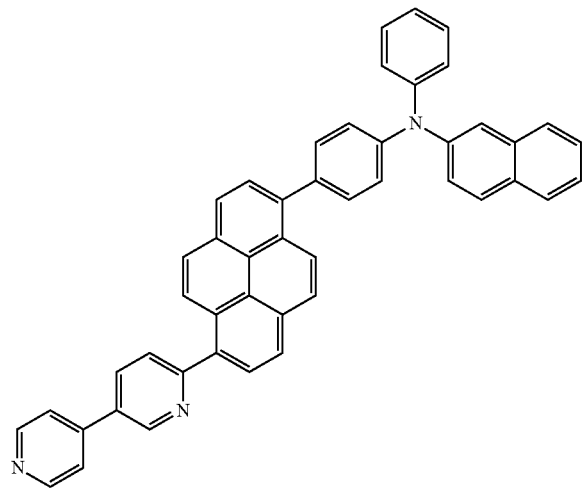
14
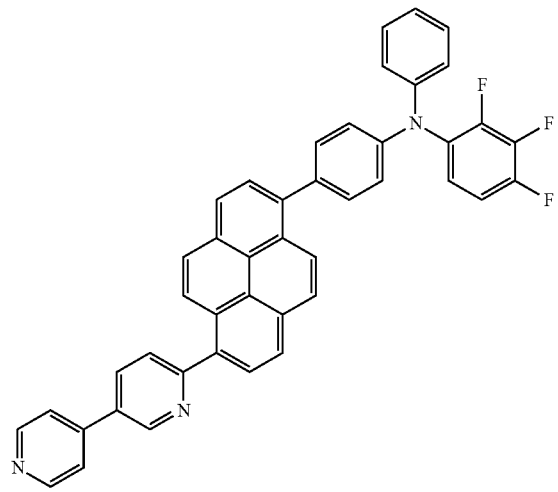
15
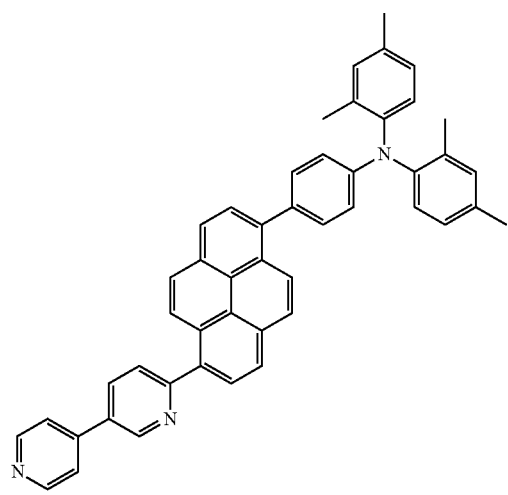
16
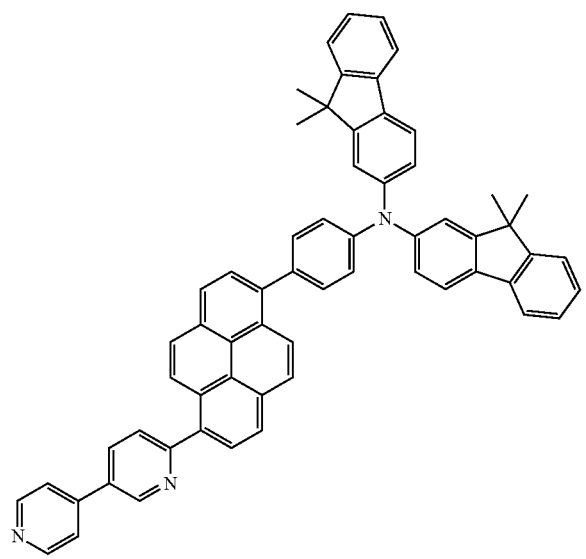

17
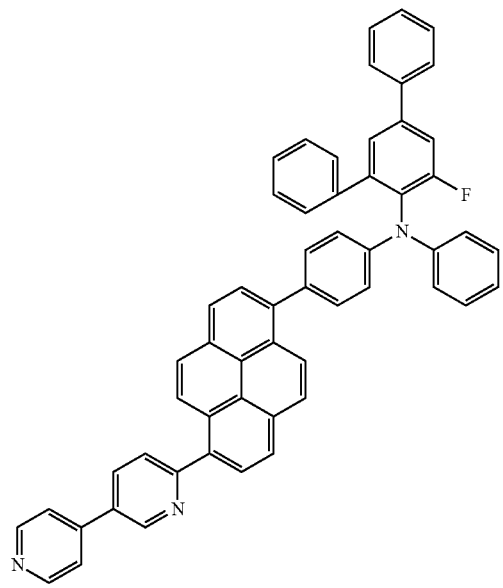
18
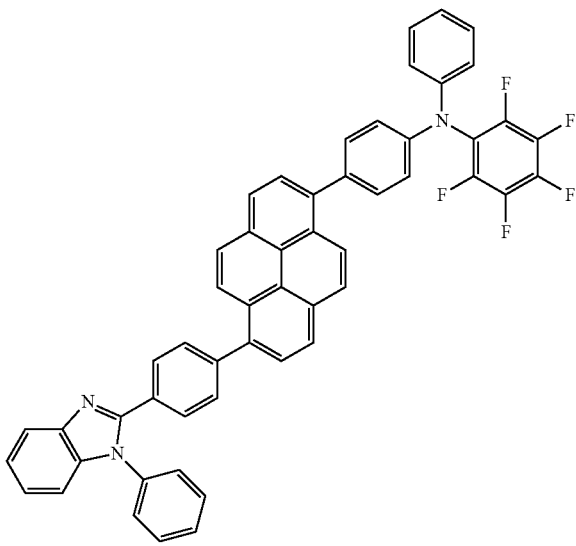
19
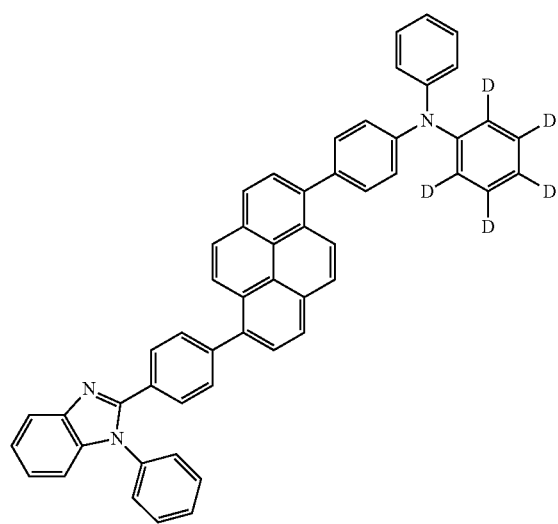
20
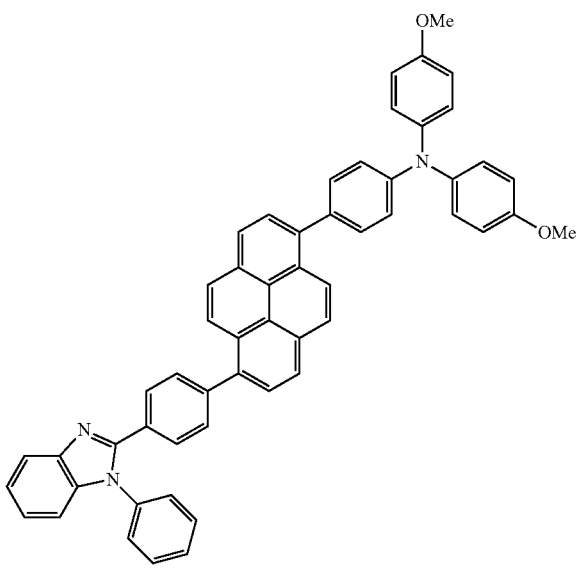

-continued
21
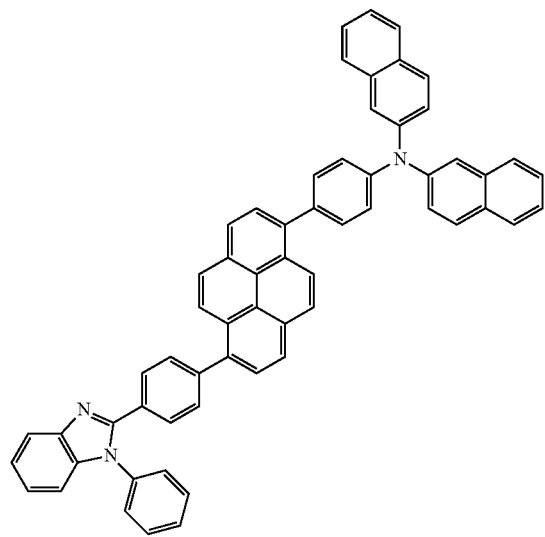
22
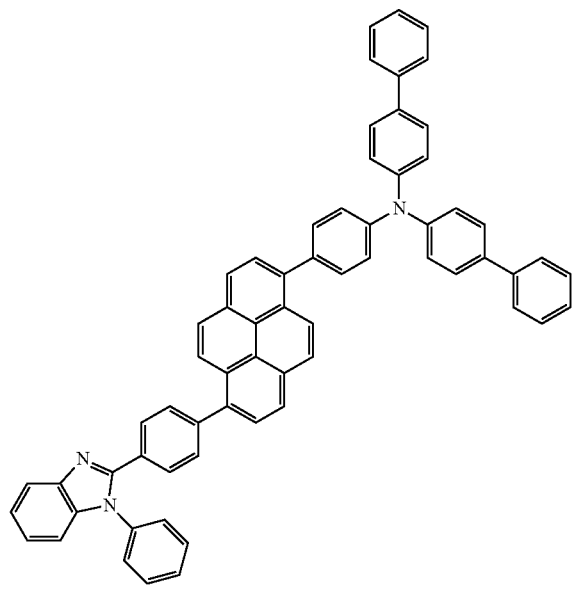
23
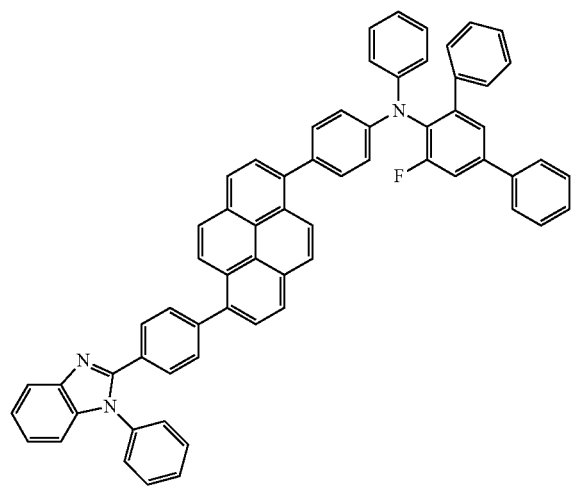
24
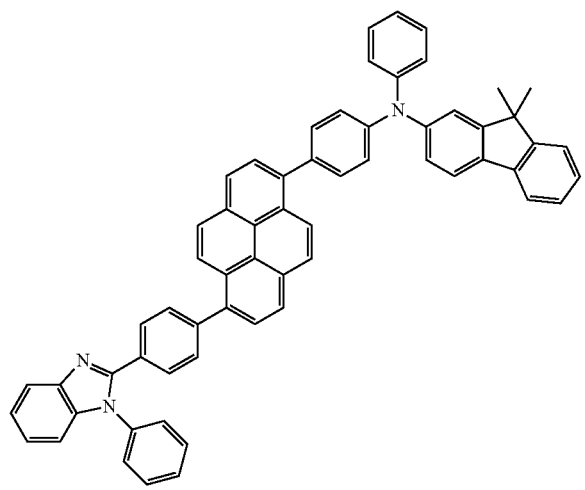

25
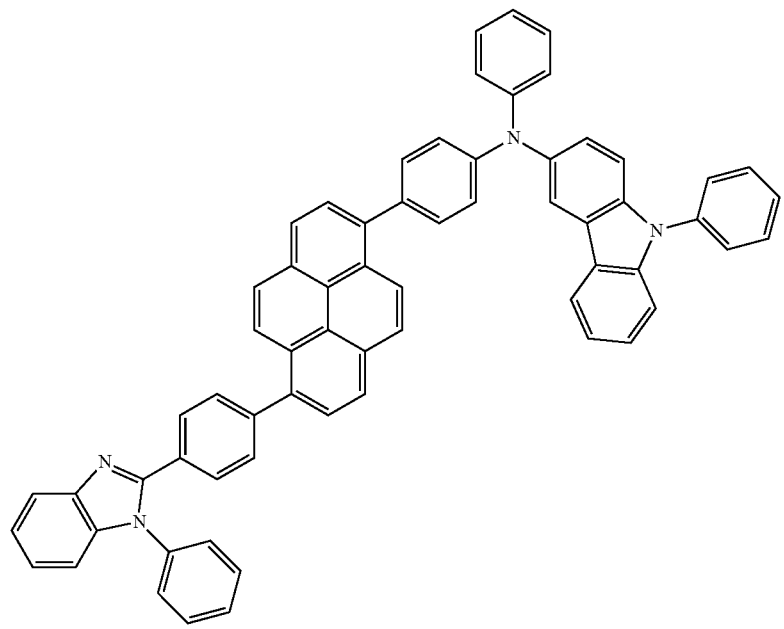
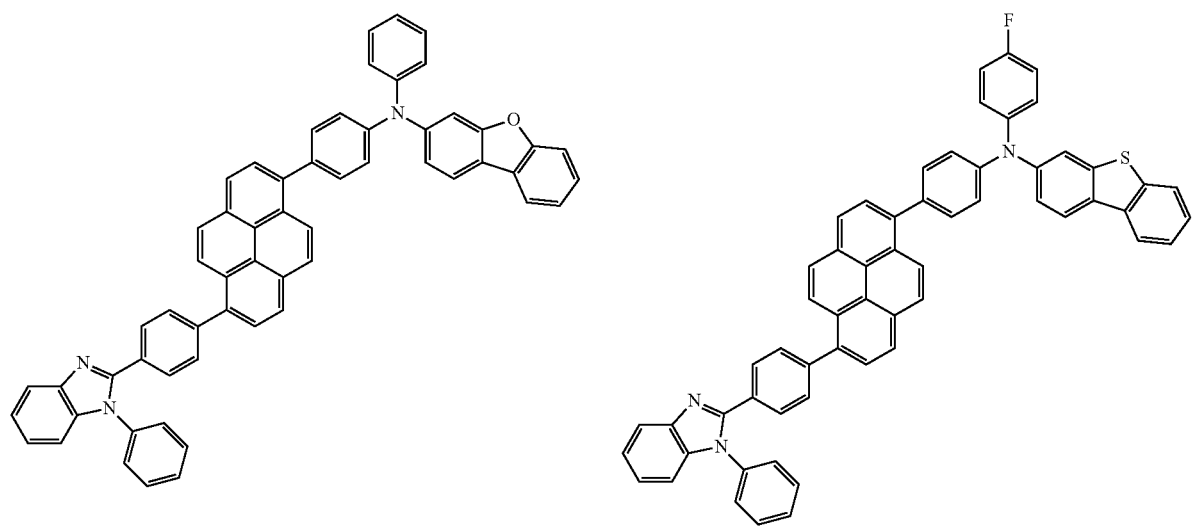

-continued
28
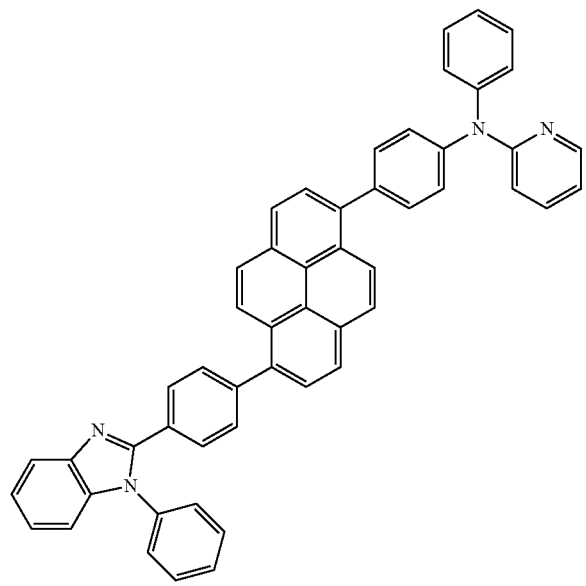
29
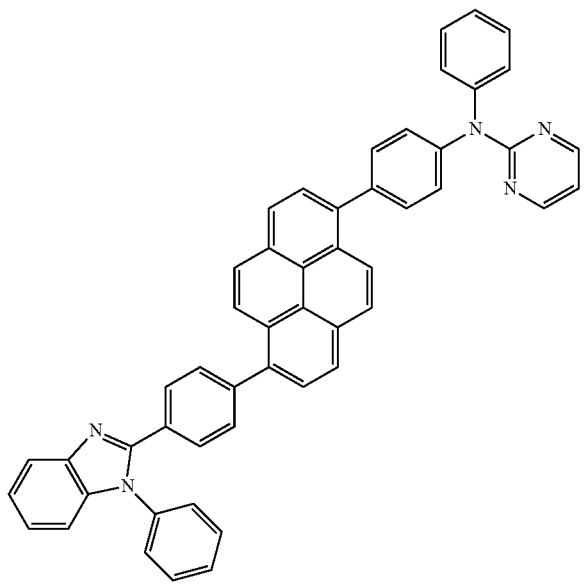
30
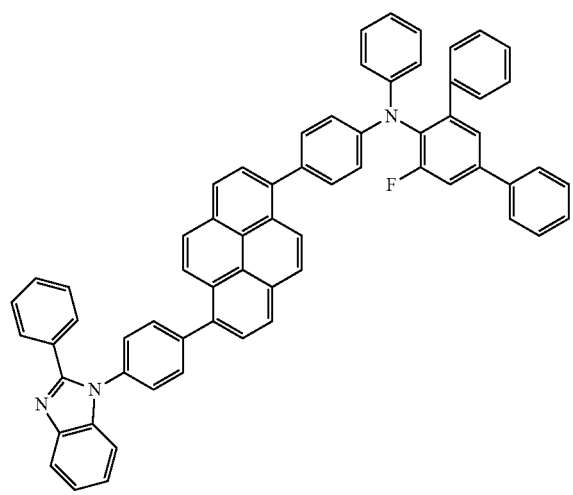
31
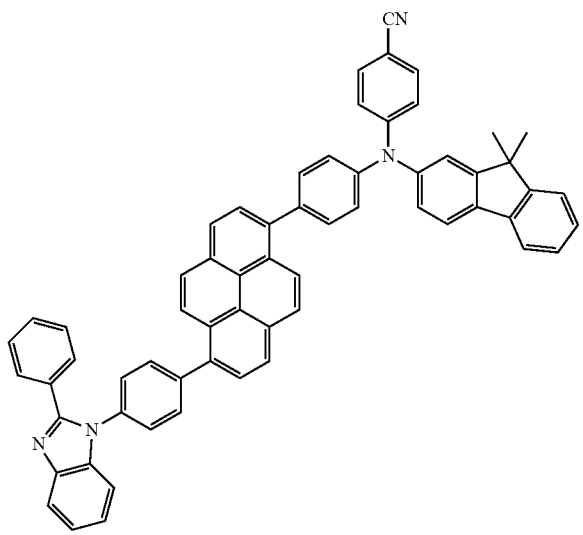
32
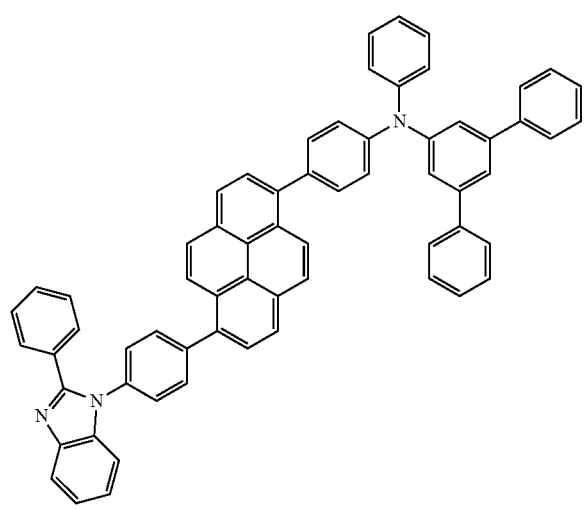
33
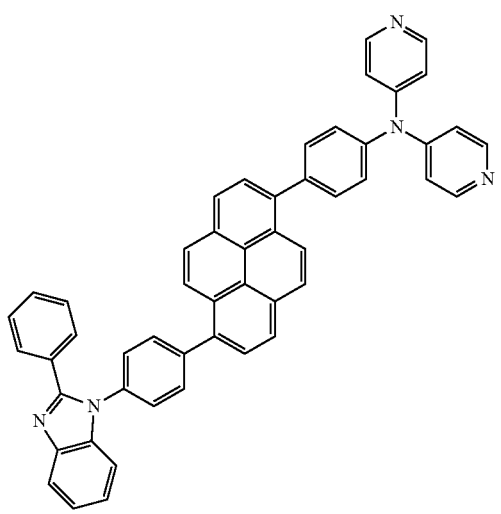

-continued
34
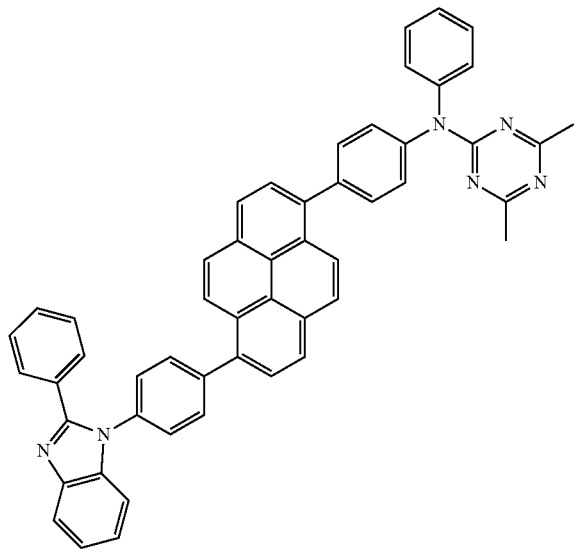
35
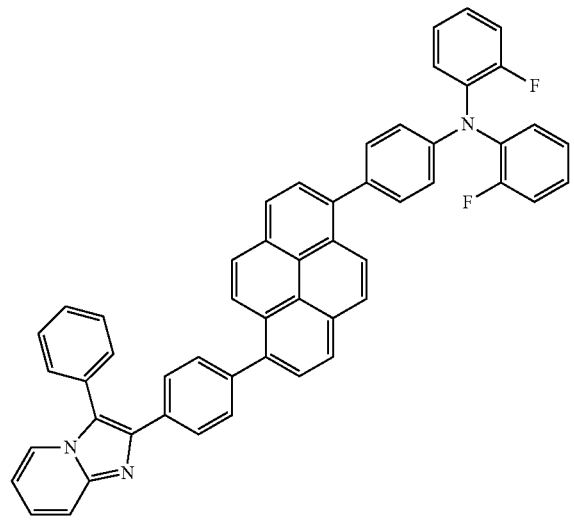
36
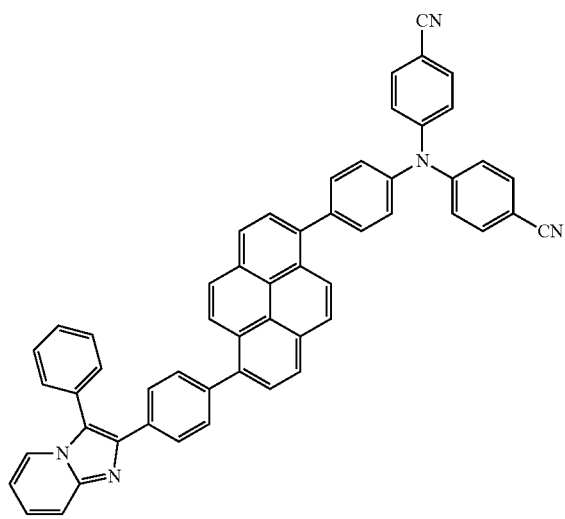
37
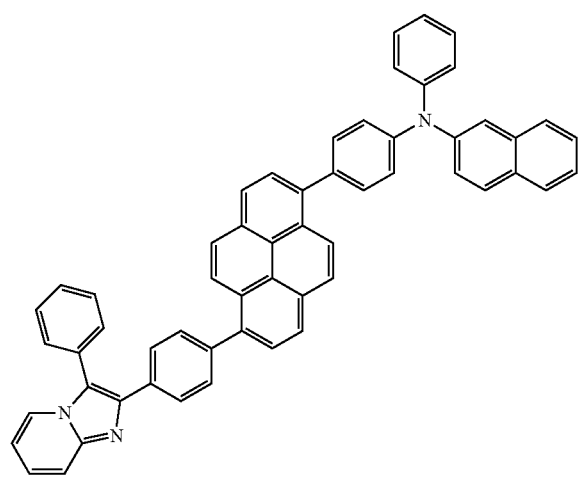
38
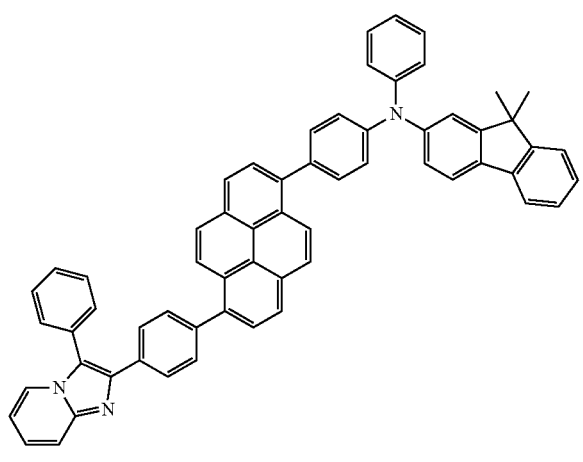
39
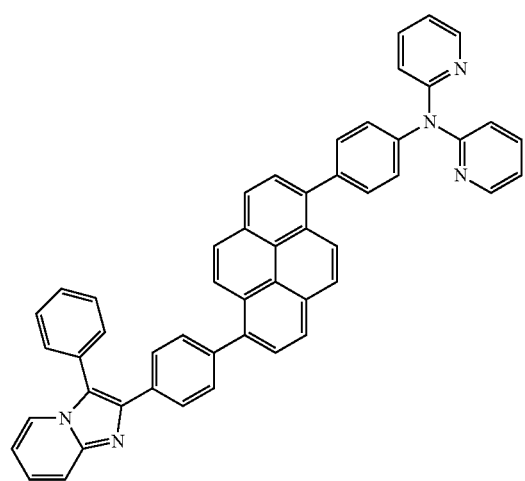

40
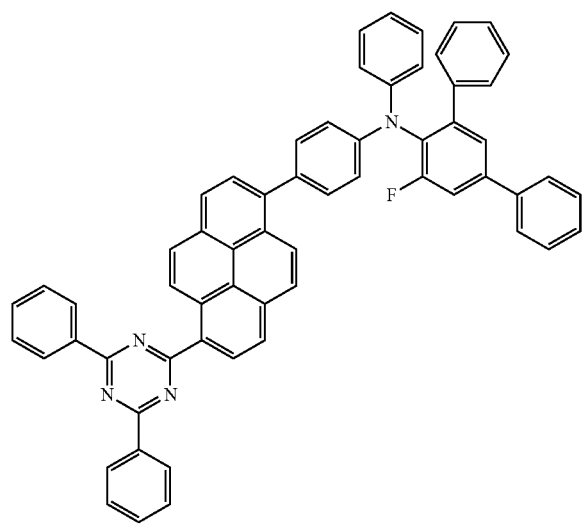
41
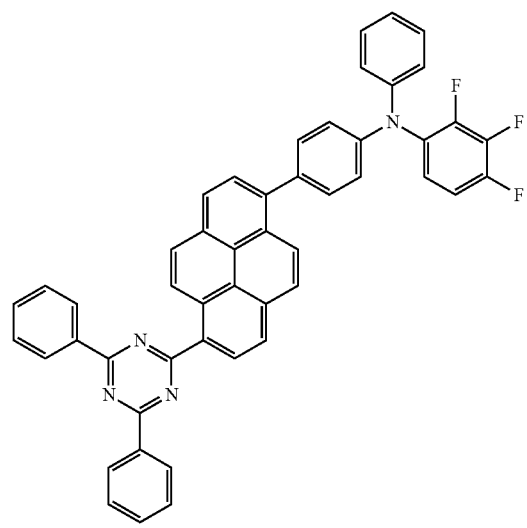
42
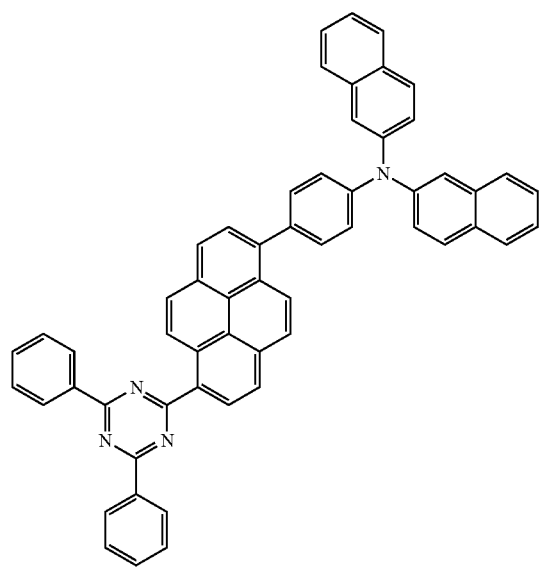
43
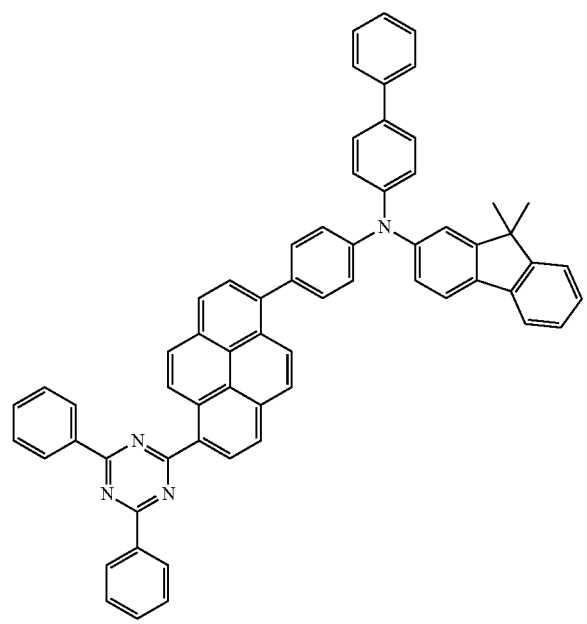

-continued
44
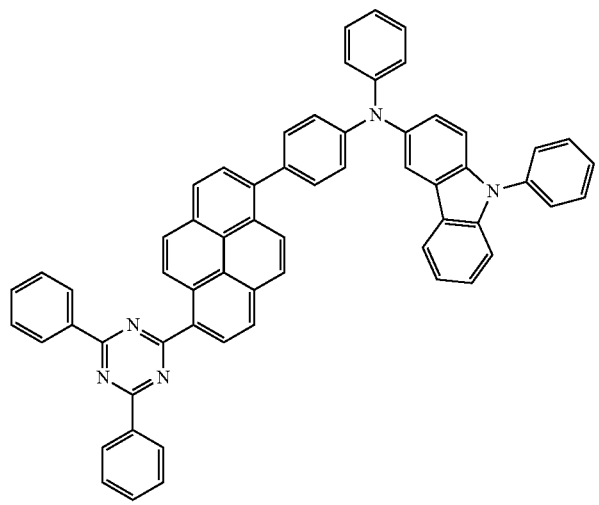
45
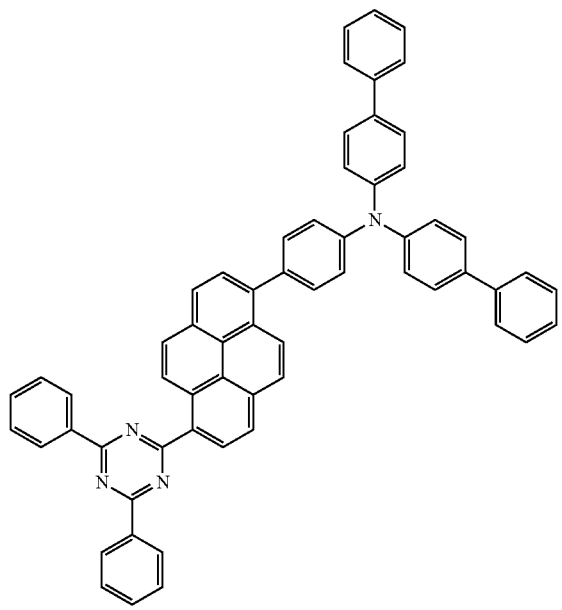
46
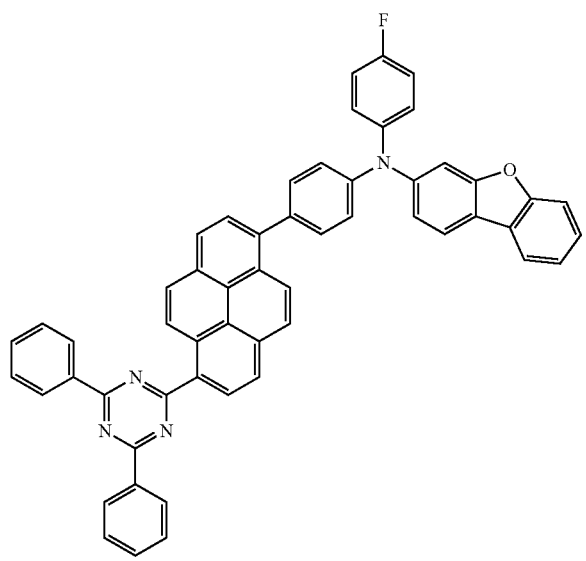
47
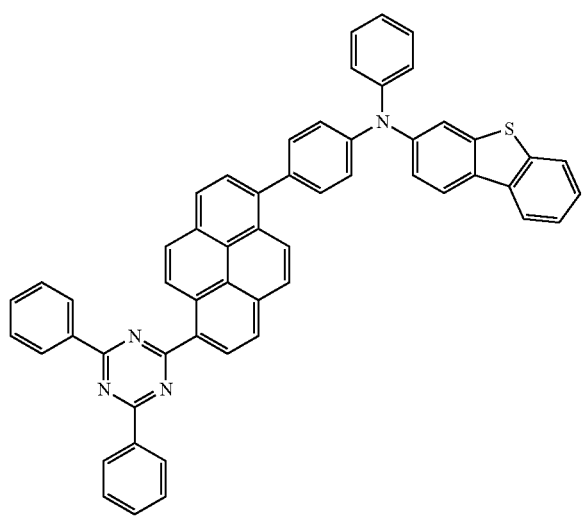

-continued
48
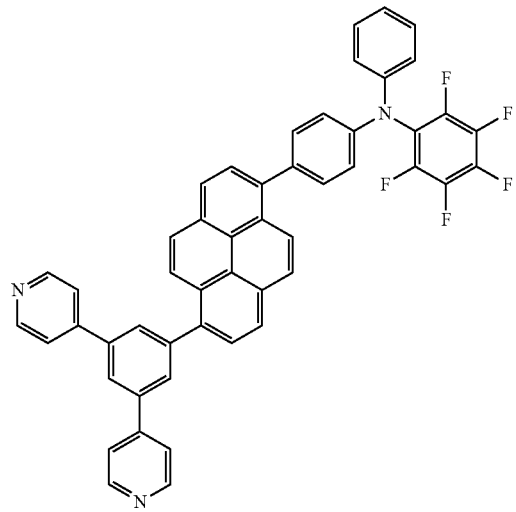
49
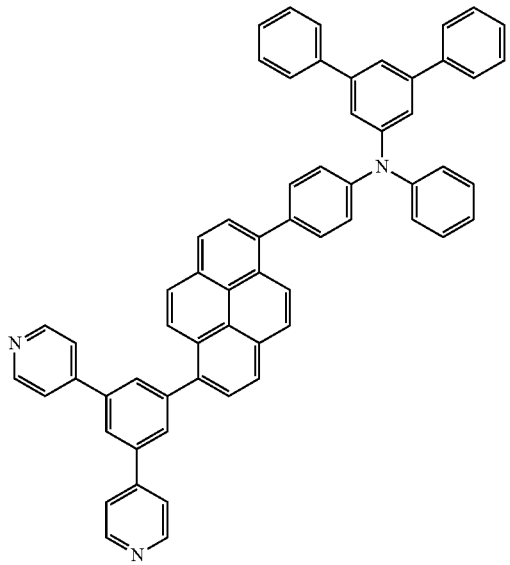
50
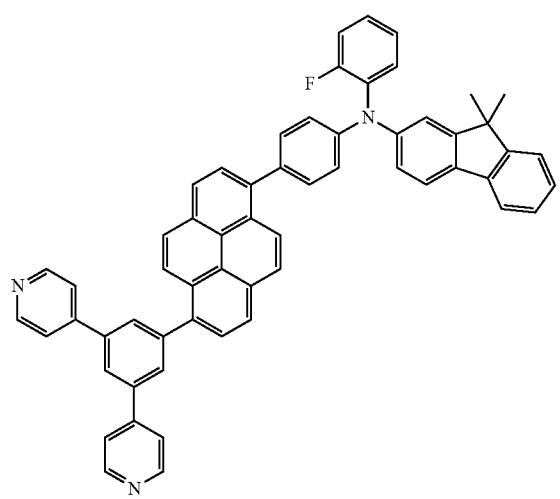
51
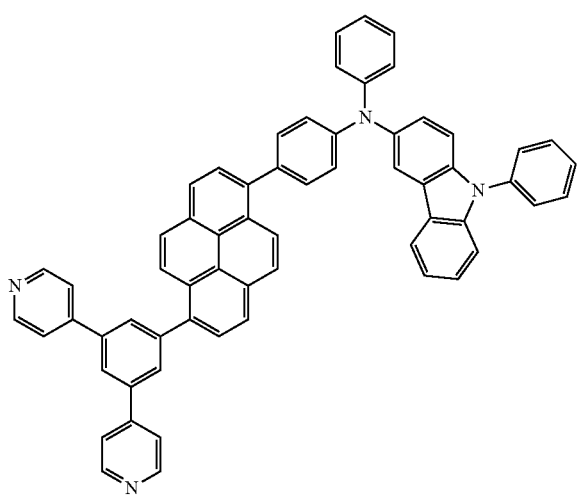
52
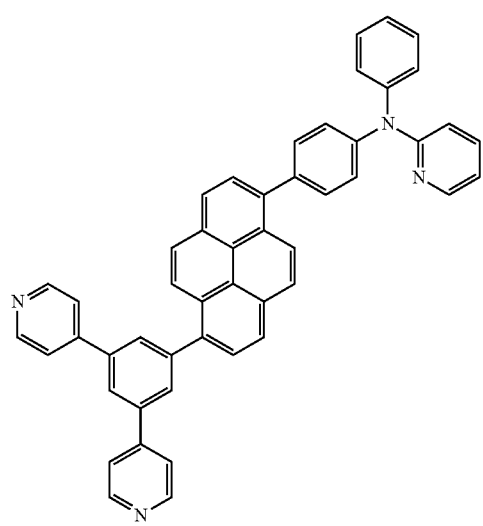
53
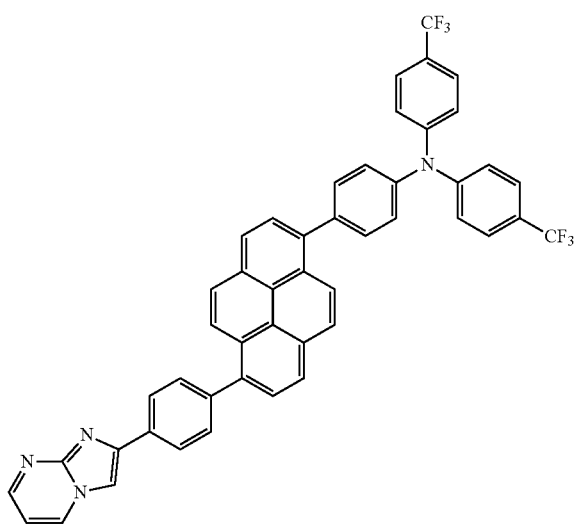

-continued
54
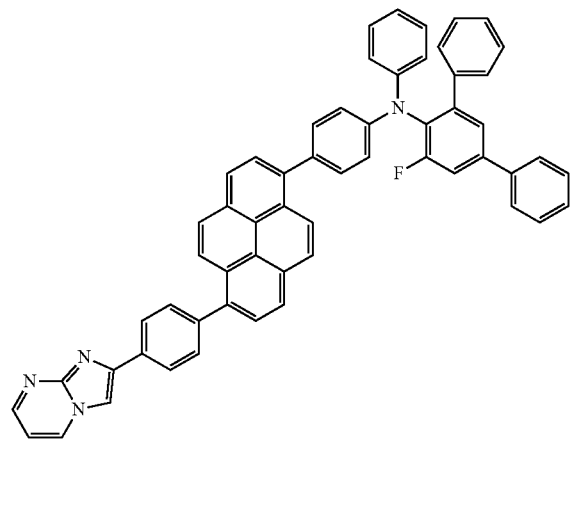
55
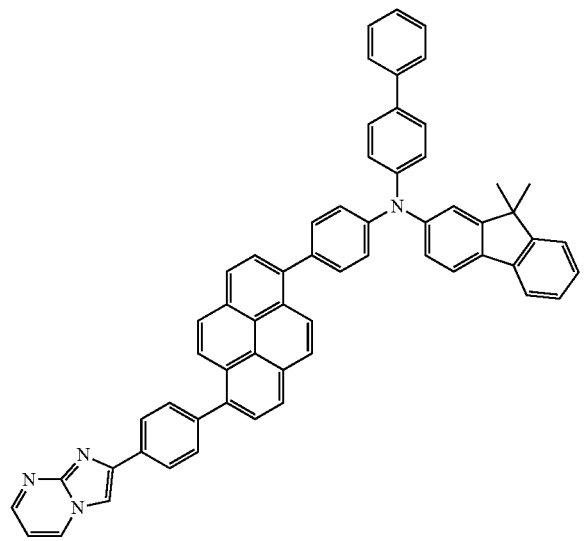
56
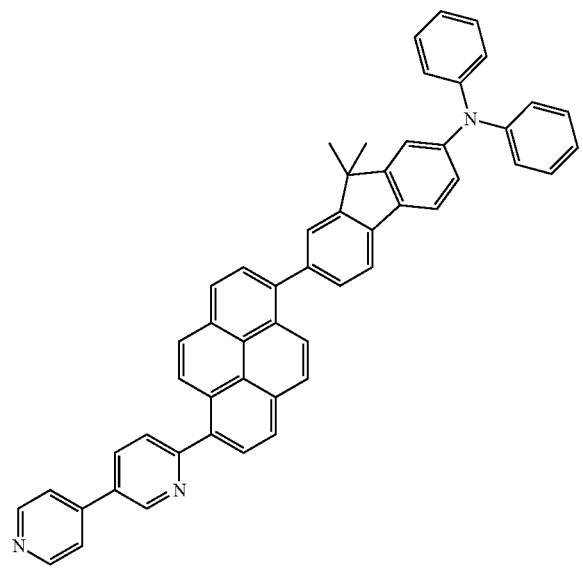
57
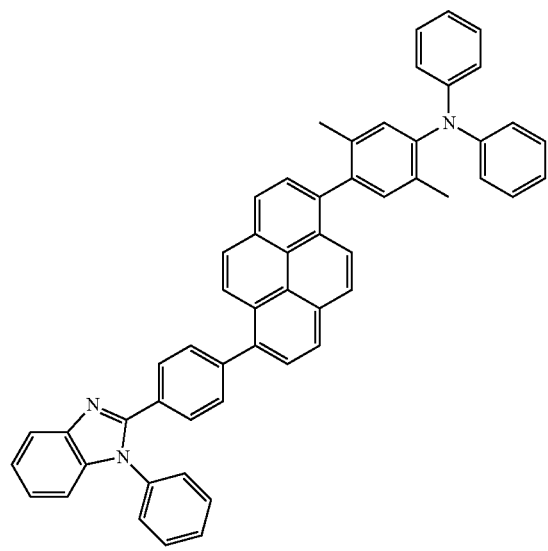

58
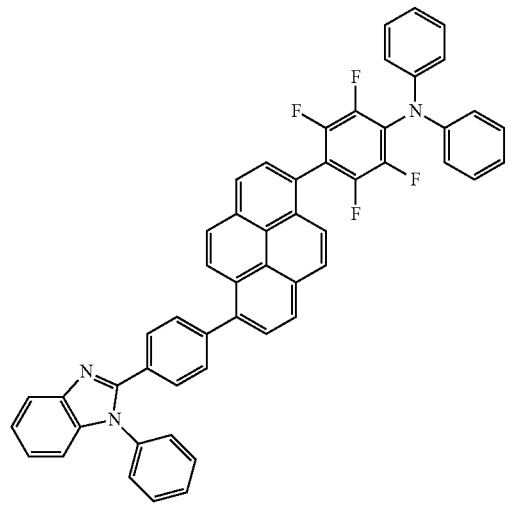
59
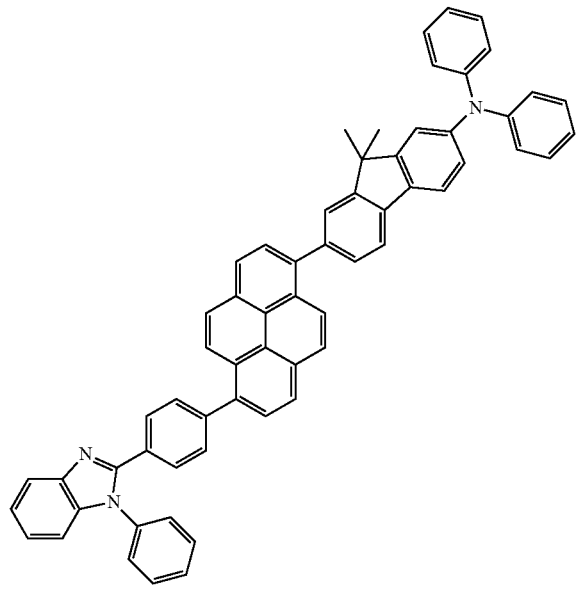
60
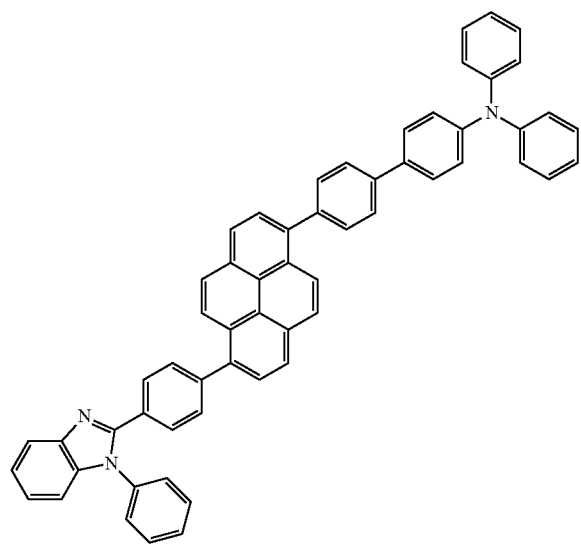
61
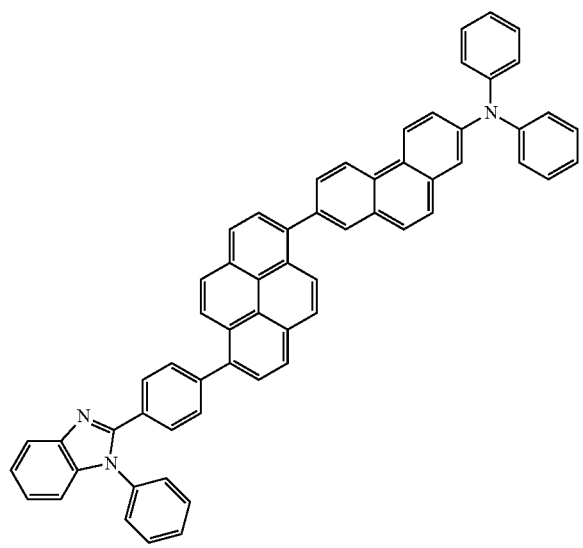

-continued
62
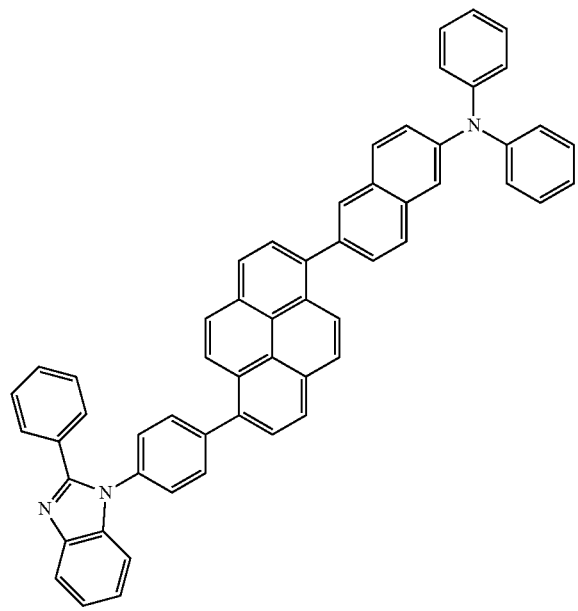
63
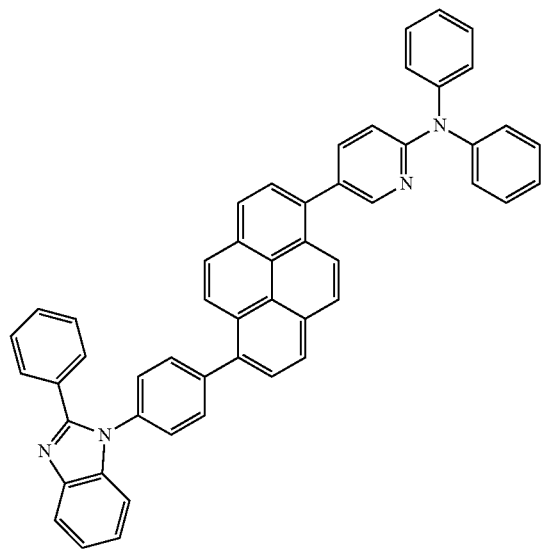
64
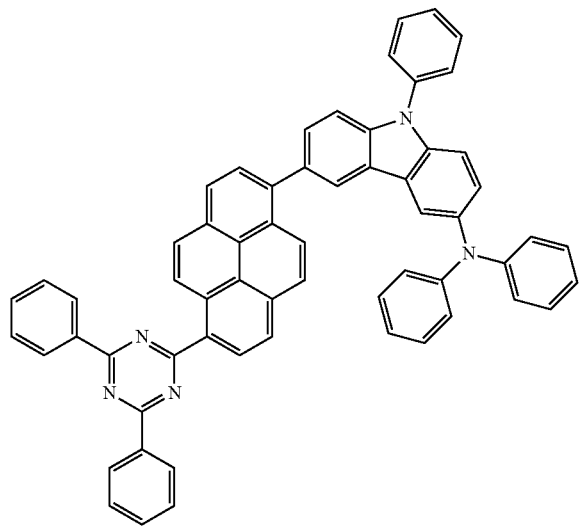
65
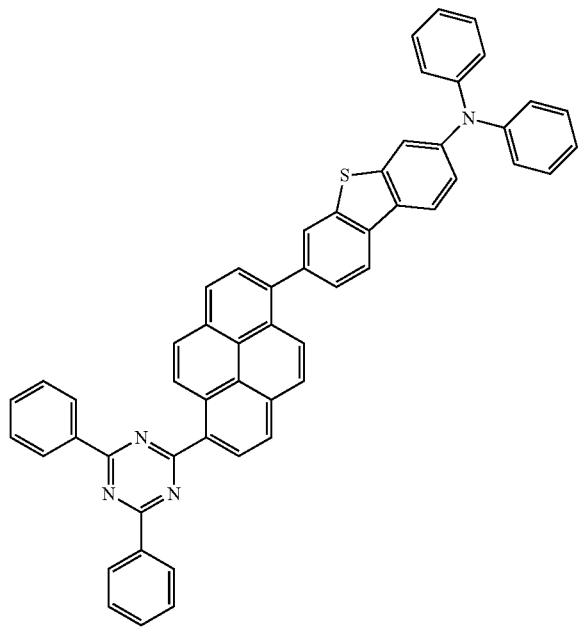

66
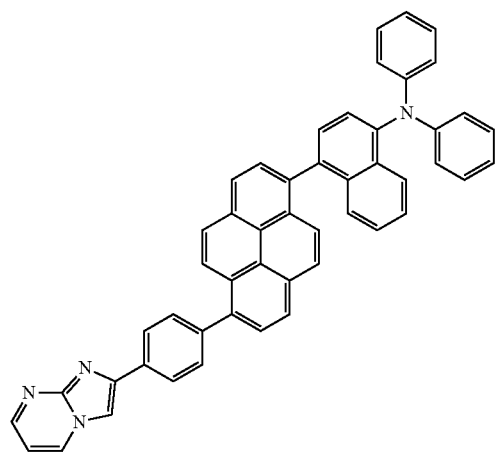
67
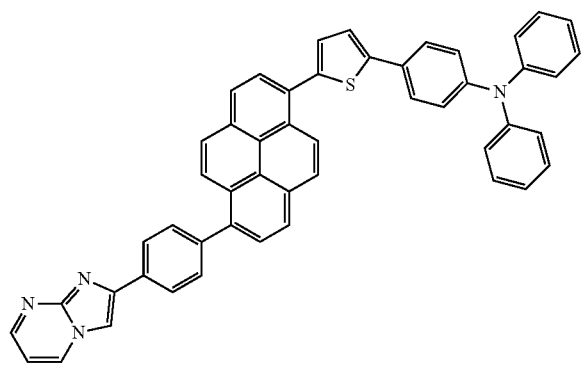
68
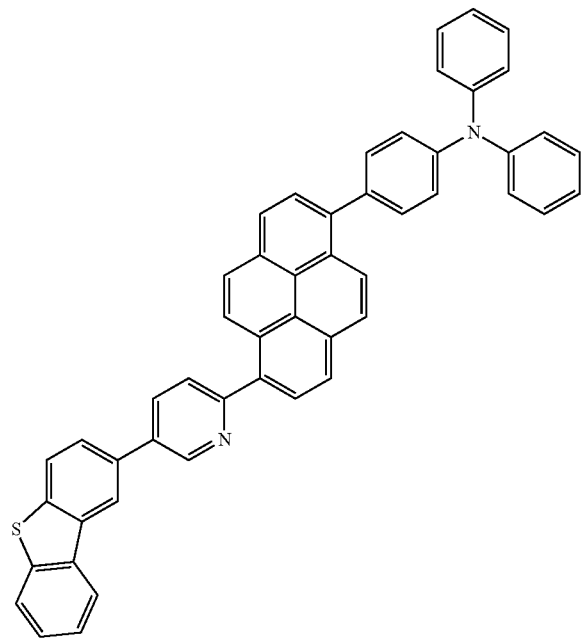
69
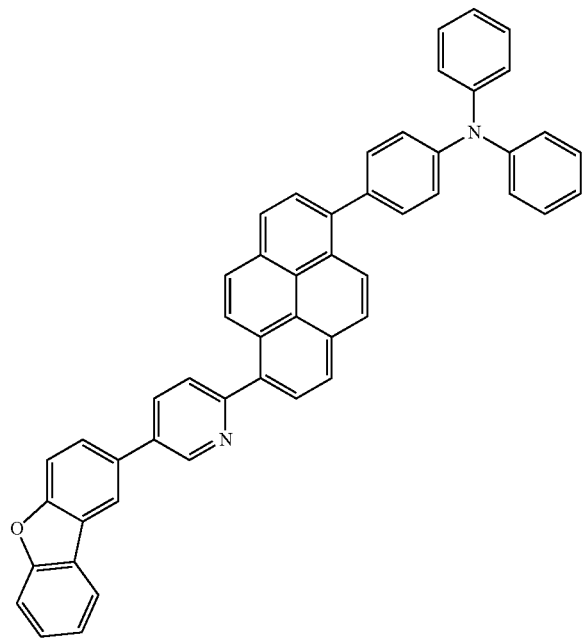

-continued

70

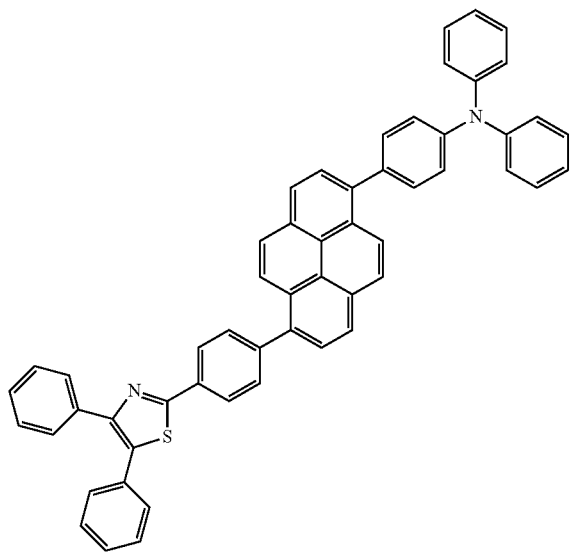

71

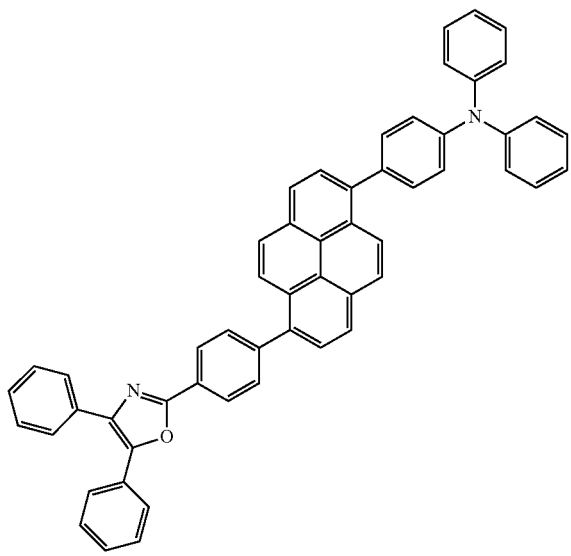

14. An organic light-emitting diode comprising:
a first electrode;
an organic layer on the first electrode; and
a second electrode on the organic layer, wherein the organic layer comprises:
an emission layer,
a hole transport area between the first electrode and the emission layer,
an electron transport area between the emission layer and the second electrode, and
at least one of the pyrene-based compound of claim 1.

15. The organic light-emitting diode of claim 14, wherein:
the hole transport area comprises at least one layer selected from a hole injection layer, a hole transport layer, a functional layer having a hole injection function and a hole transport function, a buffer layer, and an electron blocking layer, and
the electron transport area comprises at least one of a hole blocking layer, an electron transport layer, and an electron injection layer.

16. The organic light-emitting diode of claim 14, wherein:
the pyrene-based compound is in the emission layer,
the pyrene-based compound in the emission layer acts as a dopant, and
the emission layer further comprises a host.

17. The organic light-emitting diode of claim 14, wherein the pyrene-based compound is in the electron transport area.

18. The organic light-emitting diode of claim 14, wherein the electron transport area comprises an electron transport layer comprising the pyrene-based compound.

19. A pyrene-based compound represented by Formula 1 below:

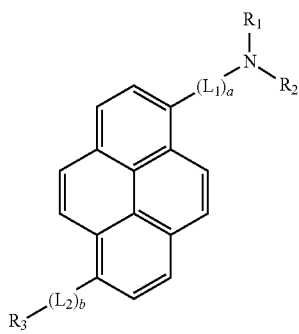

Formula 1 wherein in Formula 1:
$L_1$ and $L_2$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, and a substituted or unsubstituted $C_2$-$C_{60}$ heteroarylene group;
a is an integer from 1 to 3;
b is an integer from 0 to 3;
$R_1$ and $R_2$ are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, and a substituted or unsubstituted $C_2$-$C_{60}$ heteroaryl group; and
$R_3$ is selected from
i) an imidazolyl group, a triazolyl group, an isoxazolyl group, an oxatriazolyl group, a thiazolyl group, an isothiazolyl group, a thiadiazolyl group, a thioatriazolyl group, a benzoimidazolyl group, an imidazopyrimidinyl group, a benzoxazolyl group, a benzothiazolyl group, a pyrimidinyl group, a pyrazinyl group, a triazinyl group, a quinolinyl group, an isoquinolinyl group, a phthalazinyl group, and a quinazolinyl group; and ii) an imidazolyl group, a triazolyl group, an isoxazolyl group, an oxatriazolyl group, a thiazolyl group, an isothiazolyl group, a thiadiazolyl group, a thioatriazolyl group, benzoimidazolyl group, an imidazopyrimidinyl group, a benzoxazolyl group, benzothiazolyl group, a pyrimidinyl group, a pyrazinyl group, a triazinyl group, a quinolinyl group, an isoquinolinyl group, a phthalazinyl group, and a quinazolinyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group;

a phenyl group, a naphthyl group, an anthryl group, a fluorenyl group, a carbazolyl group, a pyridinyl group, a pyrimidinyl group, a pyrazinyl group, a pyridazinyl group, a triazinyl group, a quinolyl group, an isoquinolyl group, dibenzothio phenyl group, and a dibenzofuranyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group; and —Si($Q_{13}$)($Q_{14}$)($Q_{15}$) wherein $Q_{13}$ to $Q_{15}$ are each independently selected from a $C_1$-$C_{20}$ alkyl group, a $C_1$-$C_{20}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridinyl group, a pyrimidinyl group, a pyrazinyl group, a pyridazinyl group, a triazinyl group, a quinolyl group, and an isoquinolyl group.

* * * * *